(12) United States Patent
Oliverius et al.

(10) Patent No.: US 11,540,876 B2
(45) Date of Patent: Jan. 3, 2023

(54) IRRIGATED HIGH DENSITY ELECTRODE CATHETER

(71) Applicant: St. Jude Medical, Cardiology Division, Inc., St. Paul, MN (US)

(72) Inventors: Andrew R. Oliverius, Eagan, MN (US); Ryan Kenneth Buesseler, Delano, MN (US); John Hong, Prior Lake, MN (US); Jodee Wakefield, Minneapolis, MN (US); Brent Ford, Minneapolis, MN (US)

(73) Assignee: St. Jude Medical Cardiology Division, Inc., St. Paul, MN (US)

( * ) Notice: Subject to any disclaimer, the term of this patent is extended or adjusted under 35 U.S.C. 154(b) by 580 days.

(21) Appl. No.: 15/585,859

(22) Filed: May 3, 2017

(65) Prior Publication Data
US 2017/0319269 A1   Nov. 9, 2017

Related U.S. Application Data

(60) Provisional application No. 62/331,292, filed on May 3, 2016.

(51) Int. Cl.
*A61B 18/14* (2006.01)
*A61B 34/20* (2016.01)
(Continued)

(52) U.S. Cl.
CPC .......... *A61B 18/1492* (2013.01); *A61B 34/20* (2016.02); *A61M 25/0043* (2013.01); *A61M 25/0068* (2013.01); *A61M 39/12* (2013.01); *A61B 2018/0016* (2013.01); *A61B 2018/00214* (2013.01); *A61B 2018/00351* (2013.01);
(Continued)

(58) Field of Classification Search
CPC .. A61B 2018/0016; A61B 2018/00577; A61B 2018/00351; A61B 2217/007; A61B 2218/002; A61B 2018/00029; A61B 2018/00214; A61B 2018/00839; A61B 2018/1407; A61B 2018/1467; A61B 18/1492; A61B 34/20; A61B 2034/2051; A61M 25/0071; A61M 25/0127;
(Continued)

(56) References Cited

U.S. PATENT DOCUMENTS

| 4,522,212 A | 6/1985 | Gelinas et al. |
| 5,702,438 A | 12/1997 | Avitall |

(Continued)

FOREIGN PATENT DOCUMENTS

| AU | 2015202258 A1 | 5/2015 |
| AU | 2016204351 A1 | 1/2017 |

(Continued)

*Primary Examiner* — Eun Hwa Kim
*Assistant Examiner* — Adam Z Minchella
(74) *Attorney, Agent, or Firm* — Kilpatrick Townsend & Stockton LLP

(57) ABSTRACT

An irrigated high density electrode catheter can comprise a catheter shaft. The catheter shaft can include a proximal end and a distal end and can define a catheter shaft longitudinal axis. A flexible tip portion can be located adjacent to the distal end of the catheter shaft. An irrigated coupler can be disposed on the distal end of the catheter shaft and can be configured to discharge fluid over the flexible tip portion.

19 Claims, 49 Drawing Sheets

(51) Int. Cl.
    *A61M 25/00*     (2006.01)
    *A61M 39/12*     (2006.01)
    *A61B 18/00*     (2006.01)
    *A61M 5/14*     (2006.01)

(52) U.S. Cl.
    CPC ............... *A61B 2018/00577* (2013.01); *A61B 2018/00839* (2013.01); *A61B 2018/1407* (2013.01); *A61B 2018/1467* (2013.01); *A61B 2034/2051* (2016.02); *A61B 2217/007* (2013.01); *A61B 2218/002* (2013.01); *A61M 5/14* (2013.01); *A61M 2205/3317* (2013.01)

(58) Field of Classification Search
    CPC .... A61M 25/0068; A61M 39/12; A61M 5/14; A61M 25/0043; A61M 2205/3317
    See application file for complete search history.

(56) References Cited

U.S. PATENT DOCUMENTS

| | | | |
|---|---|---|---|
| 5,893,847 A | 4/1999 | Kordis | |
| 5,964,757 A | 10/1999 | Ponzi | |
| 5,992,418 A * | 11/1999 | de la Rama | A61B 18/1492 606/41 |
| 6,029,091 A | 2/2000 | de la Rama et al. | |
| 6,071,282 A | 6/2000 | Fleischman | |
| 6,123,699 A | 9/2000 | Webster, Jr. | |
| 6,171,277 B1 | 1/2001 | Ponzi | |
| 6,183,463 B1 | 2/2001 | Webster, Jr. | |
| 6,198,974 B1 | 3/2001 | Webster, Jr. | |
| 6,210,407 B1 | 4/2001 | Webster | |
| 6,267,746 B1 | 7/2001 | Bumbalough | |
| 6,415,187 B1 | 7/2002 | Kuzma et al. | |
| 6,522,932 B1 | 2/2003 | Kuzma et al. | |
| 6,652,515 B1 | 11/2003 | Maguire et al. | |
| 6,658,302 B1 | 12/2003 | Kuzma et al. | |
| 6,961,602 B2 | 11/2005 | Fuimaono et al. | |
| 7,027,851 B2 | 4/2006 | Mejia | |
| 7,089,045 B2 | 8/2006 | Fuimaono et al. | |
| 7,099,712 B2 | 8/2006 | Fuimaono et al. | |
| 7,228,164 B2 | 6/2007 | Fuimaono et al. | |
| 7,257,435 B2 | 8/2007 | Plaza | |
| 7,412,274 B2 | 8/2008 | Mejia | |
| 7,429,261 B2 | 9/2008 | Kunis et al. | |
| 7,561,907 B2 | 7/2009 | Fuimaono et al. | |
| 8,103,327 B2 | 1/2012 | Harlev et al. | |
| 8,157,848 B2 | 4/2012 | Zhang et al. | |
| 8,271,099 B1 | 9/2012 | Swanson | |
| 8,391,947 B2 | 3/2013 | Urman et al. | |
| 8,486,063 B2 | 7/2013 | Werneth et al. | |
| 8,560,086 B2 | 10/2013 | Just | |
| 8,565,894 B2 | 10/2013 | Vetter et al. | |
| 8,603,069 B2 | 12/2013 | Selkee | |
| 8,706,193 B2 | 4/2014 | Govari et al. | |
| 8,744,599 B2 | 6/2014 | Tegg | |
| 9,044,245 B2 | 6/2015 | Condie et al. | |
| 9,066,725 B2 | 6/2015 | Christian | |
| 9,474,894 B2 | 10/2016 | Mercanzini et al. | |
| 9,820,664 B2 | 11/2017 | Hotlink et al. | |
| 9,833,608 B2 | 12/2017 | Masson | |
| 9,907,480 B2 | 3/2018 | Basu et al. | |
| 9,949,656 B2 | 4/2018 | Wu et al. | |
| 2003/0004508 A1 | 1/2003 | Morgan et al. | |
| 2003/0093103 A1* | 5/2003 | Malackowski | A61B 34/20 606/170 |
| 2005/0159741 A1 | 7/2005 | Paul et al. | |
| 2007/0066878 A1 | 3/2007 | Worley et al. | |
| 2008/0140152 A1 | 6/2008 | Imran et al. | |
| 2008/0312521 A1 | 12/2008 | Solomon | |
| 2009/0149848 A1 | 6/2009 | Werneth et al. | |
| 2009/0198300 A1 | 8/2009 | Zhang et al. | |
| 2011/0118726 A1 | 5/2011 | de la Rama et al. | |
| 2011/0160720 A1 | 6/2011 | Johnson | |
| 2012/0046655 A1* | 2/2012 | Besch | A61M 39/10 16/421 |
| 2012/0197108 A1 | 8/2012 | Hartmann et al. | |
| 2012/0271302 A1 | 10/2012 | Behl et al. | |
| 2012/0296232 A1 | 11/2012 | Ng | |
| 2013/0012938 A1 | 1/2013 | Asirvatham et al. | |
| 2013/0096572 A1* | 4/2013 | Donhowe | A61B 34/10 606/130 |
| 2013/0231659 A1 | 9/2013 | Hill et al. | |
| 2013/0253504 A1 | 9/2013 | Fang | |
| 2013/0274582 A1 | 10/2013 | Afonso et al. | |
| 2014/0163548 A1* | 6/2014 | Christian | A61B 18/1492 606/41 |
| 2014/0200639 A1 | 7/2014 | de la Rama | |
| 2014/0206985 A1* | 7/2014 | Kariv | A61B 5/065 600/424 |
| 2014/0296849 A1 | 10/2014 | Coe et al. | |
| 2014/0296902 A1 | 10/2014 | Huszar et al. | |
| 2014/0316496 A1 | 10/2014 | Masson et al. | |
| 2014/0336636 A1 | 11/2014 | Huszar et al. | |
| 2014/0350564 A1 | 11/2014 | Huszar et al. | |
| 2015/0105645 A1 | 4/2015 | Subramaniam et al. | |
| 2015/0133760 A1 | 5/2015 | Kordis et al. | |
| 2015/0141785 A1 | 5/2015 | Hayam et al. | |
| 2015/0159741 A1 | 6/2015 | Versteyhe et al. | |
| 2015/0351652 A1 | 12/2015 | Marecki et al. | |
| 2016/0113582 A1 | 4/2016 | Altmann et al. | |
| 2016/0143588 A1 | 5/2016 | Hoitink et al. | |
| 2016/0213916 A1 | 7/2016 | de la Rama | |
| 2016/0317094 A1 | 11/2016 | Byrd et al. | |
| 2016/0331471 A1 | 11/2016 | Deno et al. | |
| 2016/0374582 A1 | 12/2016 | Wu et al. | |
| 2016/0374753 A1 | 12/2016 | Wu et al. | |
| 2017/0000365 A1 | 1/2017 | Wu et al. | |
| 2017/0000980 A1* | 1/2017 | Potosky | A61K 9/0053 |
| 2017/0042449 A1 | 2/2017 | Deno et al. | |
| 2017/0049348 A1 | 2/2017 | Deno et al. | |
| 2017/0112404 A1 | 4/2017 | de la Rama et al. | |
| 2017/0112405 A1 | 4/2017 | Sterrett et al. | |
| 2017/0319269 A1 | 11/2017 | Oliverius et al. | |
| 2017/0367756 A1 | 12/2017 | Sliwa et al. | |
| 2018/0050190 A1 | 2/2018 | Masson | |
| 2018/0056038 A1 | 3/2018 | Aujla | |
| 2018/0070845 A1 | 3/2018 | Hoitink et al. | |
| 2018/0116539 A1 | 5/2018 | Olson et al. | |
| 2018/0193089 A1 | 7/2018 | Wu | |
| 2018/0335519 A1 | 11/2018 | Gliner et al. | |
| 2018/0374582 A1 | 12/2018 | Holmes et al. | |

FOREIGN PATENT DOCUMENTS

| | | |
|---|---|---|
| AU | 2016204353 A1 | 1/2017 |
| AU | 2016204355 A1 | 1/2017 |
| CA | 2934209 A1 | 12/2016 |
| CA | 2934211 A1 | 12/2016 |
| CA | 2934214 A1 | 12/2016 |
| CN | 1985757 A | 6/2007 |
| CN | 101797181 A | 8/2010 |
| CN | 104159536 A | 11/2014 |
| CN | 104968261 A | 10/2015 |
| CN | 105960201 A | 9/2016 |
| CN | 106264715 A | 1/2017 |
| CN | 106264716 A | 1/2017 |
| CN | 106308790 A | 1/2017 |
| EP | 2664295 A1 | 11/2013 |
| EP | 2732843 A1 | 5/2014 |
| EP | 2747680 A2 | 7/2014 |
| EP | 2752153 A1 | 7/2014 |
| EP | 2792322 A1 | 10/2014 |
| EP | 2792323 A1 | 10/2014 |
| EP | 2796103 A1 | 10/2014 |
| EP | 2907462 A1 | 8/2015 |
| EP | 3023052 A | 5/2016 |
| EP | 3111871 A1 | 1/2017 |
| EP | 3111872 A1 | 1/2017 |
| EP | 3114987 A1 | 1/2017 |
| EP | 3363397 A1 | 8/2018 |
| EP | 3527125 A1 | 8/2019 |
| IL | 246415 A | 12/2019 |
| JP | 2017012750 A | 1/2017 |
| JP | 2017012755 A | 1/2017 |

(56) References Cited

FOREIGN PATENT DOCUMENTS

| | | | |
|---|---|---|---|
| JP | 2017038919 A | 2/2017 | |
| RU | 2016124794 A | 12/2017 | |
| RU | 2016124801 A | 12/2017 | |
| RU | 2016125763 A | 1/2018 | |
| WO | 2004112629 A1 | 12/2004 | |
| WO | 2005114720 A2 | 12/2005 | |
| WO | 2006008481 A1 | 1/2006 | |
| WO | 2008157399 A1 | 12/2008 | |
| WO | 2014089380 A2 | 6/2014 | |
| WO | 2014/116961 A1 | 7/2014 | |
| WO | 2014113612 A1 | 7/2014 | |
| WO | WO-2014113612 A1 * | 7/2014 | ......... A61B 18/1492 |
| WO | 2015057521 A1 | 4/2015 | |
| WO | 2015095577 A1 | 6/2015 | |
| WO | 2015130824 A1 | 9/2015 | |
| WO | 2016001015 A1 | 1/2016 | |
| WO | 2016090175 A1 | 6/2016 | |
| WO | 2017017659 A1 | 2/2017 | |

\* cited by examiner

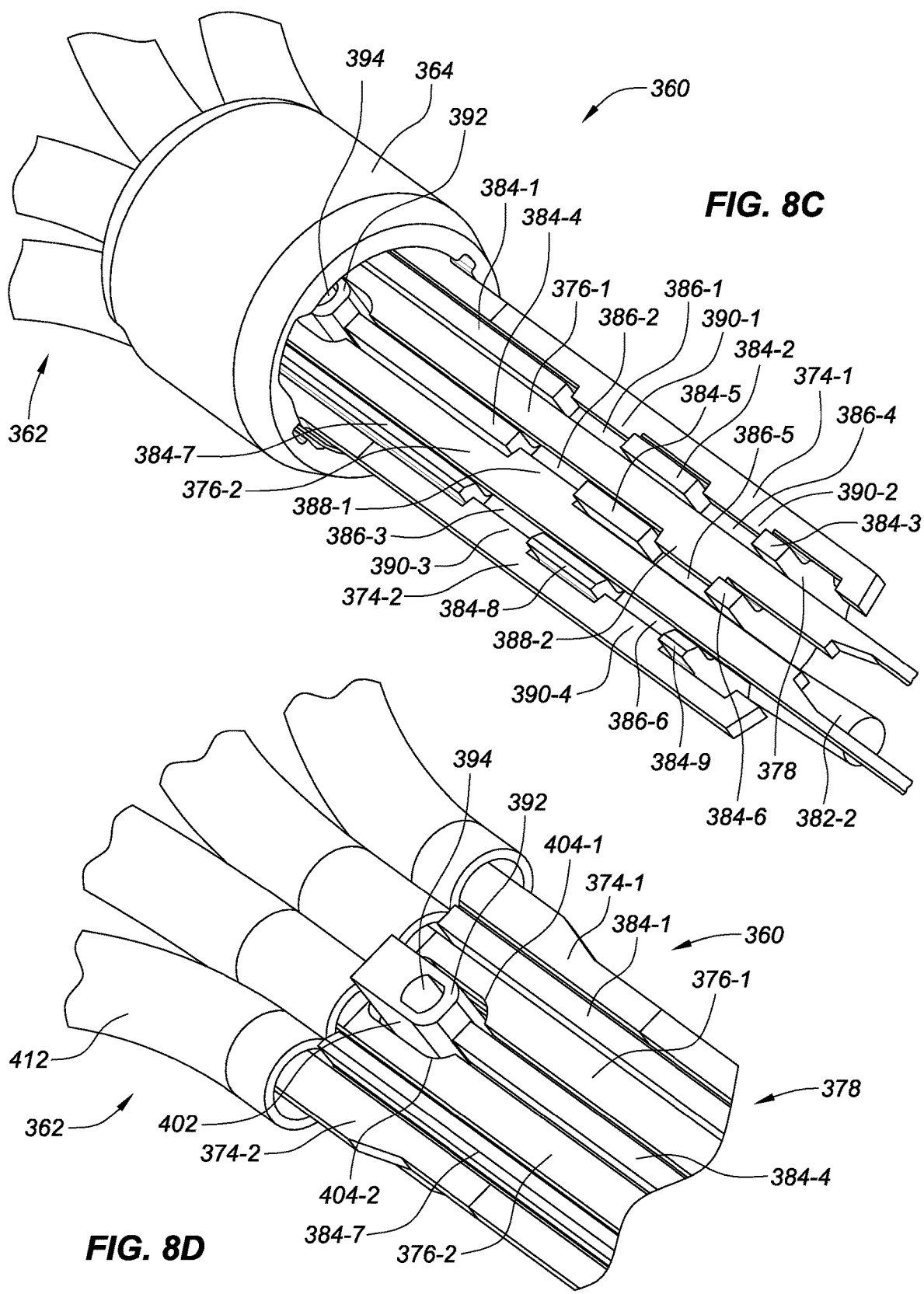

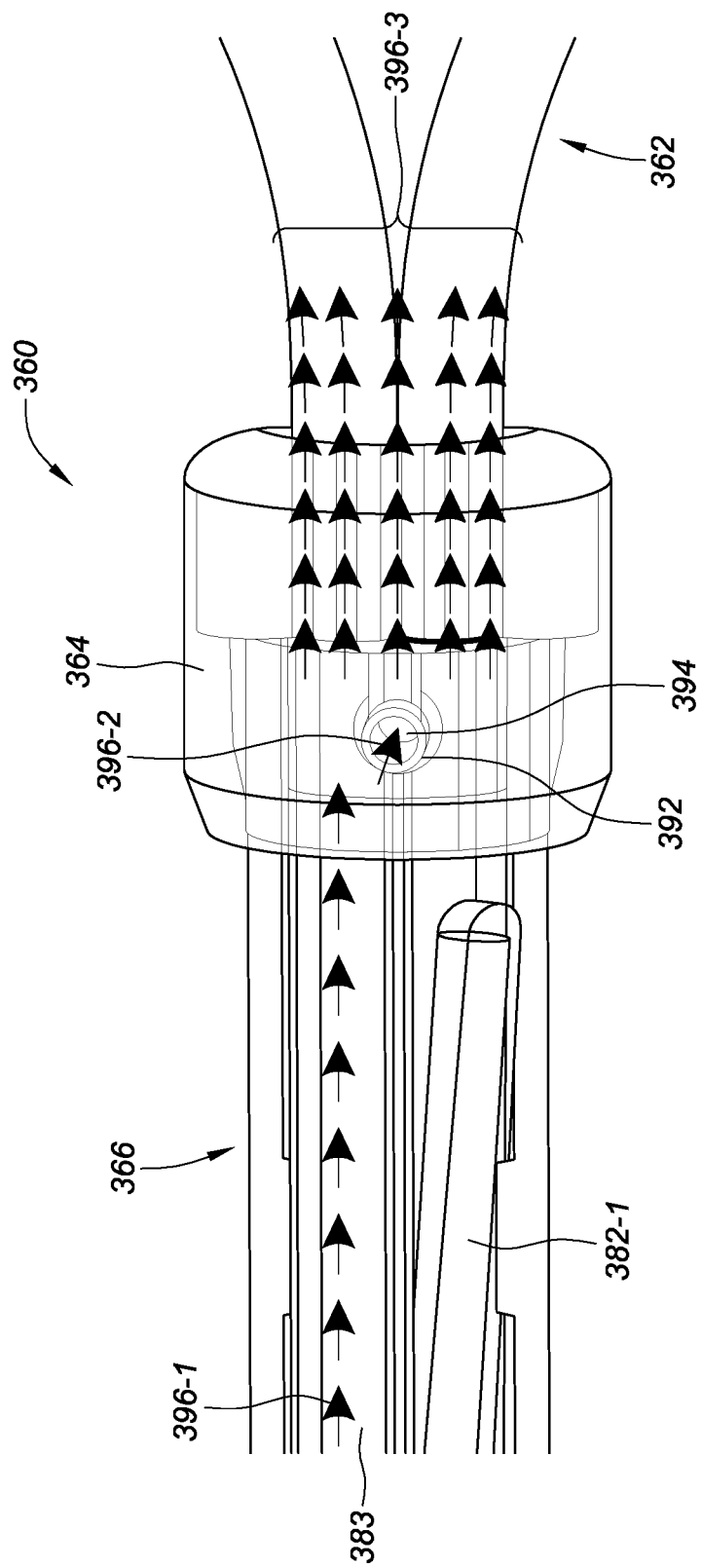

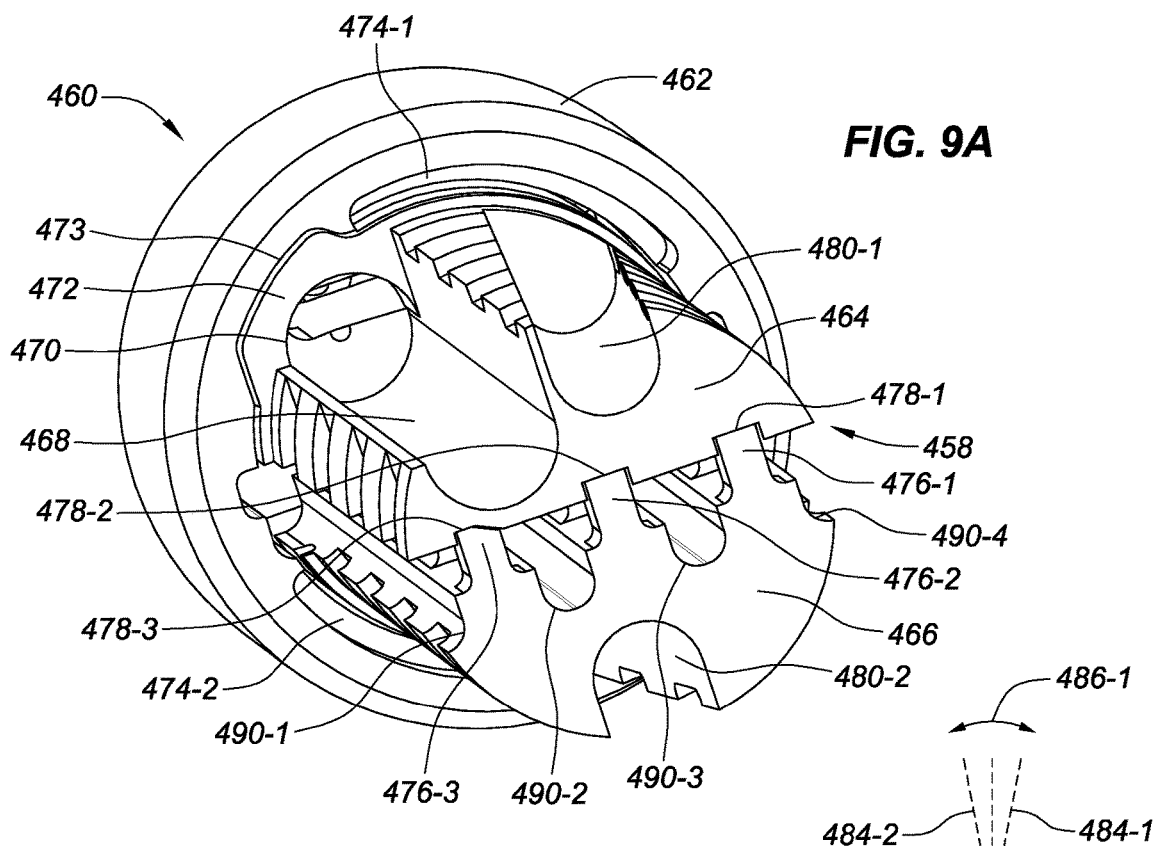
FIG. 9A
FIG. 9B
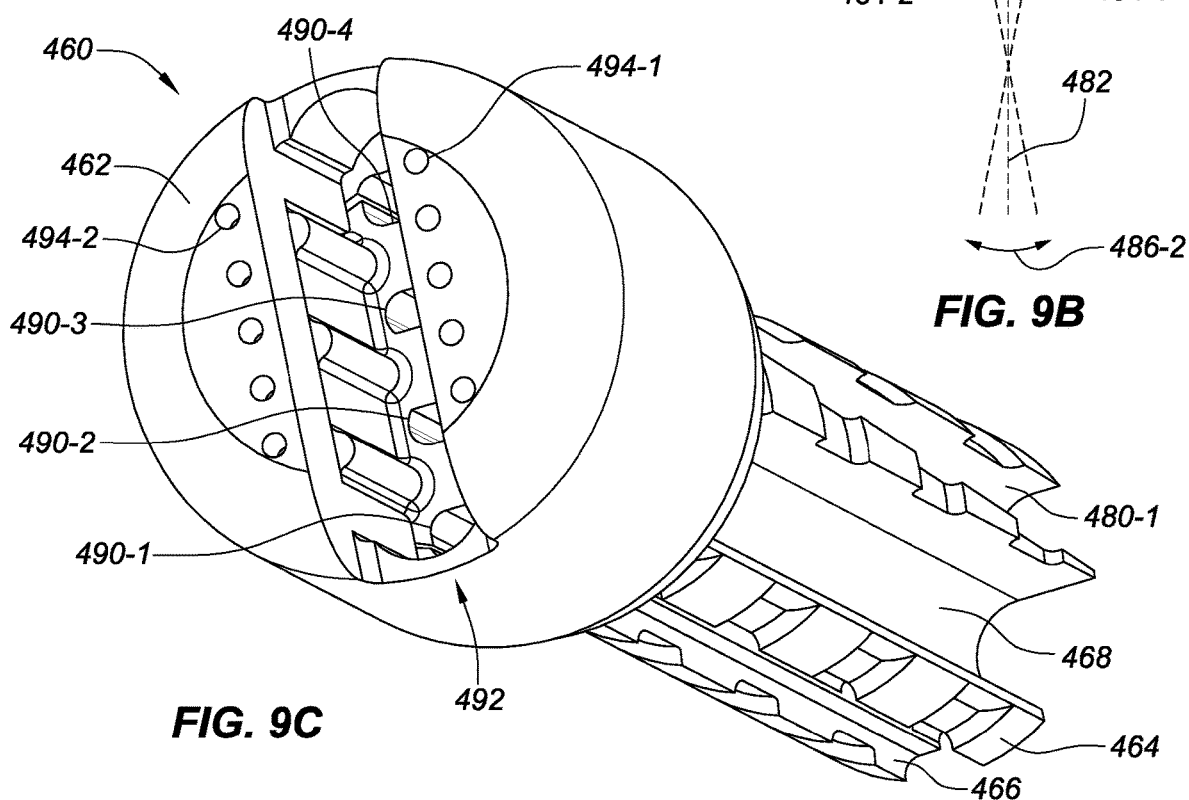
FIG. 9C

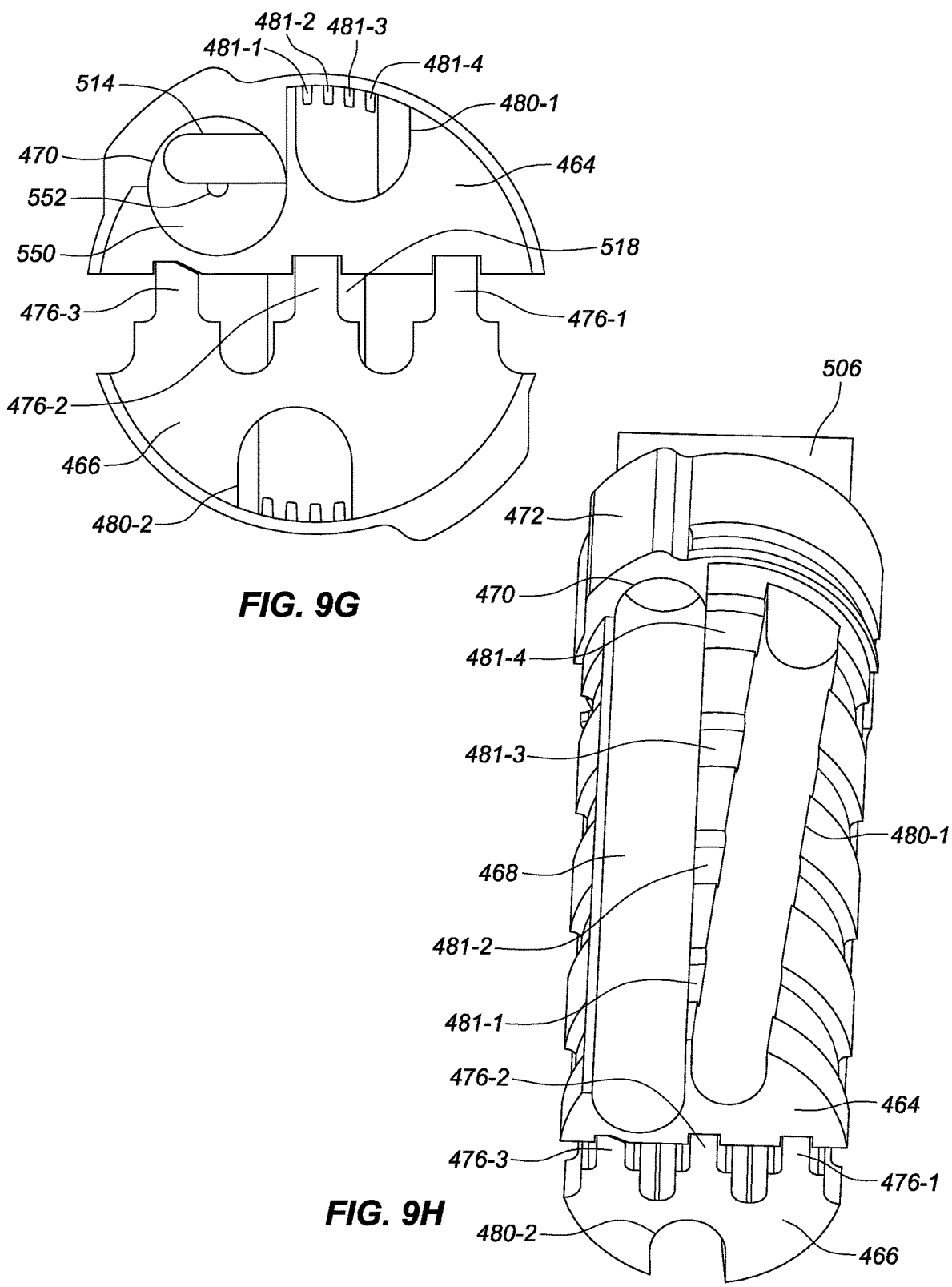

IRRIGATED HIGH DENSITY ELECTRODE CATHETER

CROSS-REFERENCE TO RELATED APPLICATION

This application claims priority to U.S. provisional patent application No. 62/331,292 entitled "Irrigated High Density Electrode Catheter," filed 3 May 2016, which is hereby incorporated by reference as though fully set forth herein.

FIELD OF THE DISCLOSURE

This disclosure relates to an irrigated high density electrode catheter.

BACKGROUND ART

Catheters have been used for cardiac medical procedures for many years. Catheters can be used, for example, to diagnose and treat cardiac arrhythmias, while positioned at a specific location within a body that is otherwise inaccessible without a more invasive procedure.

Conventional mapping catheters may include, for example, a plurality of adjacent ring electrodes encircling the longitudinal axis of the catheter and constructed from platinum or some other metal. These ring electrodes are relatively rigid. Similarly, conventional ablation catheters may comprise a relatively rigid tip electrode for delivering therapy (e.g., delivering RF ablation energy) and may also include a plurality of adjacent ring electrodes. It can be difficult to maintain good electrical contact with cardiac tissue when using these conventional catheters and their relatively rigid (or nonconforming), metallic electrodes, especially when sharp gradients and undulations are present.

Whether mapping or forming lesions in a heart, the beating of the heart, especially if erratic or irregular, complicates matters, making it difficult to keep adequate contact between electrodes and tissue for a sufficient length of time. These problems are exacerbated on contoured or trabeculated surfaces. If the contact between the electrodes and the tissue cannot be sufficiently maintained, quality lesions or accurate mapping are unlikely to result.

The foregoing discussion is intended only to illustrate the present field and should not be taken as a disavowal of claim scope.

BRIEF SUMMARY

Various embodiments of the present disclosure can include an irrigated high density electrode catheter can comprise a catheter shaft. The catheter shaft can include a proximal end and a distal end and can define a catheter shaft longitudinal axis. A flexible tip portion can be located adjacent to the distal end of the catheter shaft. An irrigated coupler can be disposed on the distal end of the catheter shaft and can be configured to discharge fluid over the flexible tip portion.

Various embodiments of the present disclosure can include a catheter. The catheter can include an elongate shaft including a proximal end and a distal end, the elongate shaft defining a shaft longitudinal axis. A coupler can be disposed within a distal end of the elongate shaft, the coupler defining a first sensor groove and a second sensor groove in an exterior surface of the coupler and a coupler longitudinal axis. A first five degree of freedom magnetic position sensor can be disposed in the first sensor groove and a second five degree of freedom magnetic position sensor can be disposed in the second sensor groove, the first five degree of freedom magnetic position sensor defining a first sensor longitudinal axis and the second five degree of freedom magnetic position sensor defining a second sensor longitudinal axis. The first sensor longitudinal axis and the second sensor longitudinal axis can be divergent with respect to each other and the coupler longitudinal axis.

Various embodiments of the present disclosure can include a medical device. The medical device can include an elongate shaft including a proximal end and a distal end, the elongate shaft defining a shaft longitudinal axis. A flexible tip mount can be disposed within the distal end of the elongate shaft, wherein the flexible tip mount includes a connective stem portion that includes a top connective stem portion and a bottom connective stem portion and an irrigated coupler connected to a distal end of the flexible tip mount. A flexible tip portion can include a proximal mounting portion and a distal flexible portion, the proximal mounting portion disposed between the top connective stem portion and the bottom connective stem portion. A first sensor groove can be defined in the top connective stem portion and a second sensor groove can be defined in the bottom connective stem portion. A first five degree of freedom magnetic position sensor can be disposed in the first sensor groove and a second five degree of freedom magnetic position sensor can be disposed in the second sensor groove, the first five degree of freedom magnetic position sensor defining a first sensor longitudinal axis and the second five degree of freedom magnetic position sensor defining a second sensor longitudinal axis.

BRIEF DESCRIPTION OF THE DRAWINGS

FIG. 8C is an isometric side, bottom, and rear view of the irrigated high density electrode catheter depicted in FIGS. 8A and 8B that includes a flexible tip portion, with an irrigated coupler and bottom connective stem portion, according to various embodiments of the present disclosure.

FIG. 8D is an isometric side, bottom, and rear view of the irrigated high density electrode catheter depicted in FIGS. 8A to 8C that includes a flexible tip portion, and bottom connective stem portion that includes an irrigation crossover, according to various embodiments of the present disclosure.

FIG. 8J is a schematic top view of the irrigated high density electrode catheter that illustrates fluid flow through the irrigated high density electrode catheter, according to embodiments of the present disclosure.

FIG. 9A is an isometric side and rear view of a flexible tip mount, according to various embodiments of the present disclosure.

FIG. 9B is a longitudinal axis along which a connective stem extends, according to embodiments of the present disclosure.

FIG. 9C is an isometric side and front view of the flexible tip mount depicted in FIG. 9A, according to various embodiments of the present disclosure.

FIG. 9G is a proximal end view of the bottom connective stem portion and the top connective stem portion as previously depicted in FIGS. 9A and 9C to 9F, according to various embodiments of the present disclosure.

FIG. 9H is an isometric top and proximal end view of the top connective stem portion and the bottom connective stem portion and FIG. 9I is a bottom and rear isometric view of the bottom connective stem portion and the top connective stem portion previously depicted in FIGS. 9A and 9C to 9G, according to various embodiments of the present disclosure.

DETAILED DESCRIPTION

Figure 1A:
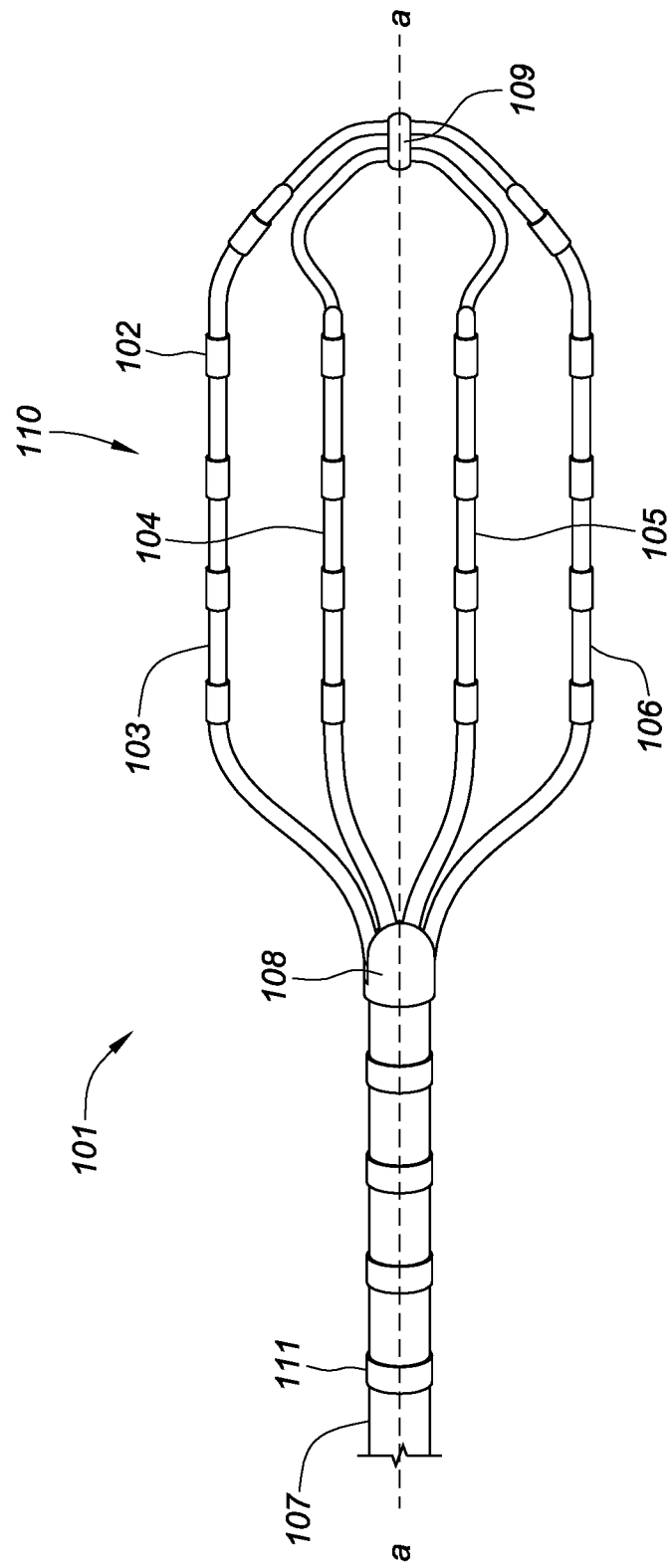
FIG. 1A is a top view of a high density electrode catheter, according to various embodiments of the present disclosure.
Figure 1B:
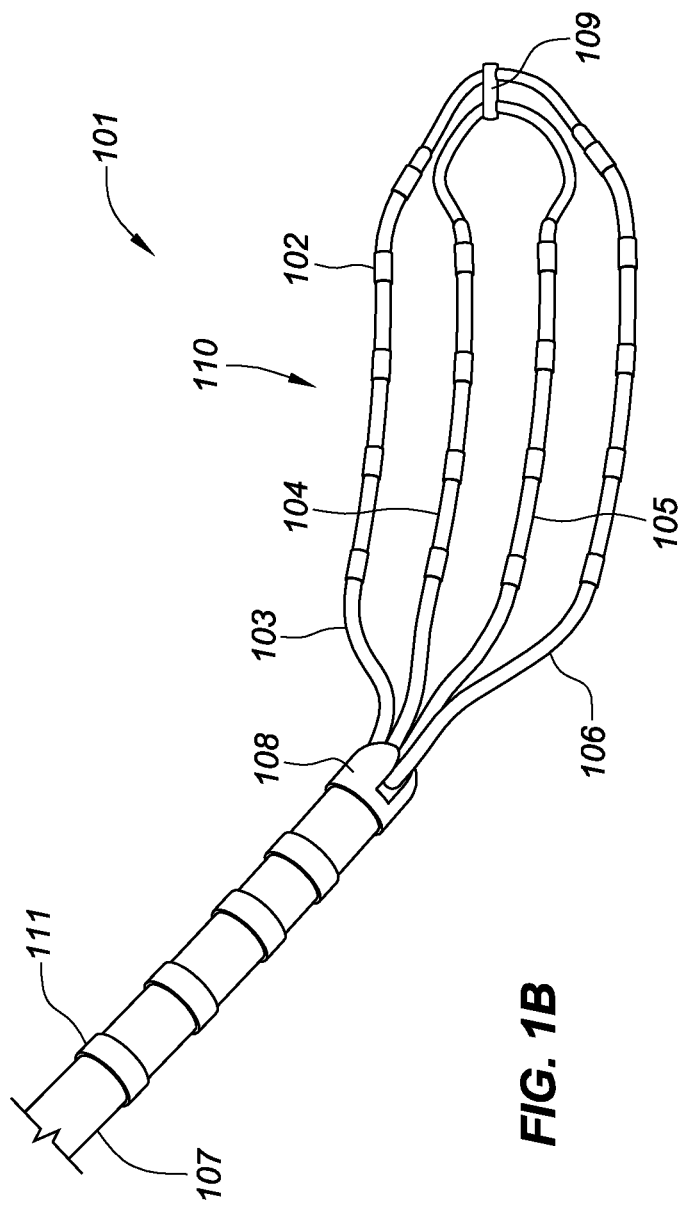
FIG. 1B is an isometric side and top view of the high density electrode catheter in FIG. 1A, according to various embodiments of the present disclosure.

FIG. 1A is a top view of a high density electrode catheter 101 and FIG. 1B is an isometric side and top view of the high density electrode catheter 101, according to various embodiments of the present disclosure. In some embodiments, the high density electrode catheter 101 can include a flexible tip portion 110 that forms a flexible array of microelectrodes 102. This planar array (or 'paddle' configuration) of microelectrodes 102 comprises four side-by-side, longitudinally-extending arms 103, 104, 105, 106, which can form a flexible framework on which the microelectrodes 102 are disposed. The four microelectrode-carrier arms can comprise a first outboard arm 103, a second outboard arm 106, a first inboard arm 104, and a second inboard arm 105, which can be joined at a distal end by a distal connective portion 209. These arms can be laterally separated from each other.

Each of the four arms can carry a plurality of microelectrodes 102. For example, each of the four arms can carry microelectrodes 102 spaced along a length of each of the four arms. Although each of the high density electrode catheters 101 depicted in FIGS. 1A and 1B depict four arms, the high density electrode catheters 101 could comprise more or fewer arms. Additionally, while the high density electrode catheter 101 depicted in FIGS. 1A and 1B depict 18 electrodes (e.g., 5 microelectrodes on the first outboard arm 103 and second outboard arm 106 and 4 microelectrodes on the first inboard arm 104 and second inboard arm 105), the catheters can include more or fewer than 18 electrodes. In addition, the first outboard arm 103 and second outboard arm 106 can include more or fewer than 5 microelectrodes and the first inboard arm 104 and second inboard arm 105 can include more or fewer than 4 microelectrodes).

In some embodiments, the microelectrodes 102 can be used in diagnostic, therapeutic, and/or mapping procedures. For example and without limitation, the microelectrodes 102 can be used for electrophysiological studies, pacing, cardiac mapping, and ablation. In some embodiments, the microelectrodes 102 can be used to perform unipolar or bipolar ablation. This unipolar or bipolar ablation can create specific lines or patterns of lesions. In some embodiments, the microelectrodes 102 can receive electrical signals from the heart, which can be used for electrophysiological studies. In some embodiments, the microelectrodes 102 can perform a location or position sensing function related to cardiac mapping.

In some embodiments, the high density electrode catheter 101 can include a catheter shaft 107. The catheter shaft 107 can include a proximal end and a distal end. The distal end can include a connector 108, which can couple the distal end of the catheter shaft 107 to a proximal end of the planar array. The catheter shaft 107 can define a catheter shaft longitudinal axis aa, as depicted in FIG. 1A, along which the first outboard arm 103, first inboard arm 104, second inboard arm 105, and second outboard arm 106 can generally extend parallel in relation therewith. The catheter shaft 107 can be made of a flexible material, such that it can be threaded through a tortuous vasculature of a patient. In some embodiments, the catheter shaft 107 can include one or more ring electrodes 111 disposed along a length of the catheter shaft 107. The ring electrodes 111 can be used for diagnostic, therapeutic, and/or mapping procedures, in an example.

As depicted in FIG. 1B, the flexible tip portion 110 can be adapted to conform to tissue (e.g., cardiac tissue). For example, when the flexible tip portion 110 contacts tissue, the flexible tip portion 110 can deflect, allowing the flexible framework to conform to the tissue. In some embodiments, the arms (or the understructure of the arms) comprising the paddle structure (or multi-arm, electrode-carrying, flexible framework) at the distal end of the catheters depicted in FIGS. 1A and 1B are preferably constructed from a flexible or spring-like material such as Nitinol and/or a flexible substrate, as discussed herein. The construction (including, for example, the length and/or diameter of the arms) and material of the arms can be adjusted or tailored to create, for example, desired resiliency, flexibility, foldability, conformability, and stiffness characteristics, including one or more characteristics that may vary from the proximal end of a single arm to the distal end of that arm, or between or among the plurality of arms comprising a single paddle structure. The foldability of materials such as Nitinol and/or flexible substrate provide the additional advantage of facilitating insertion of the paddle structure into a delivery catheter or introducer, whether during delivery of the catheter into the body or removal of the catheter from the body at the end of a procedure.

Among other things, the disclosed catheters, with their plurality of microelectrodes, are useful to (1) define regional propagation maps of particularly sized areas (e.g., one centimeter square areas) within the atrial walls of the heart; (2) identify complex fractionated atrial electrograms for ablation; (3) identify localized, focal potentials between the microelectrodes for higher electrogram resolution; and/or (4) more precisely target areas for ablation. These mapping catheters and ablation catheters are constructed to conform to, and remain in contact with, cardiac tissue despite potentially erratic cardiac motion. Such enhanced stability of the catheter on a heart wall during cardiac motion provides more accurate mapping and ablation due to sustained tissue-electrode contact. Additionally, the catheters described herein may be useful for epicardial and/or endocardial use. For example, the planar array embodiments depicted herein may be used in an epicardial procedure where the planar array of microelectrodes is positioned between the myocardial surface and the pericardium. Alternatively, the planar array embodiments may be used in an endocardial procedure to quickly sweep and/or analyze the inner surfaces of the myocardium and quickly create high-density maps of the heart tissue's electrical properties.

In some embodiments, use of the high density electrode catheter 101 can sometimes be plagued by coagulation of blood on various portions of the high density electrode catheter 101. For example, coagulation of blood can occur on the flexible tip portion 110 and/or on the connector 108 of the high density electrode catheter 101. Although coagulation of blood is discussed herein, in some instances other material can be collected on the flexible tip portion 110 and/or on the connector 108, such as tissue cells, for example. Coagulation of blood can impair the functionality of the microelectrodes if the blood coagulates on the microelectrodes. Additionally, coagulation of blood on the flexible tip portion 110 and/or on the connector 108 can cause clots to occur, if the coagulated blood breaks free. As such, it can be beneficial to prevent the coagulation of blood and/or accumulation of other material on the flexible tip portion 110 and/or on the connector 108, which can be accomplished through use of embodiments discussed in the present disclosure.

The contents of International Application No. PCT/US2014/011940 entitled Flexible High-Density Mapping Catheter Tips and Flexible Ablation Catheter Tips with Onboard High-Density Mapping Electrodes; U.S. application Ser. No. 15/331,562 entitled High Density Electrode Mapping Catheter; U.S. application Ser. No. 62/324,067 entitled High Density Electrode Mapping Catheter; U.S. application Ser. No. 15/331,369 entitled High Density Electrode Mapping Catheter; and U.S. application Ser. No. 62/484,267 entitled Ultrasonic Transducer Array Catheter with Integrated Coupler are hereby incorporated by reference as though fully set forth herein. Although some embodiments of the present disclosure include a flexible tip portion that includes diagnostic and/or therapeutic electrodes, embodiments of the present disclosure can include a flexible and/or rigid tip portion (e.g., distal assembly) in lieu of or in addition to the flexible tip portion, which can be an electrode assembly or any number of end use therapeutic and/or diagnostic devices. For example, the tip portion can include an ultrasound sensor and/or transducer, such as that associated with an intracardiac echocardiography (ICE) catheter; a laser, balloon or any other number of therapeutic and/or diagnostic devices.

Figure 2:
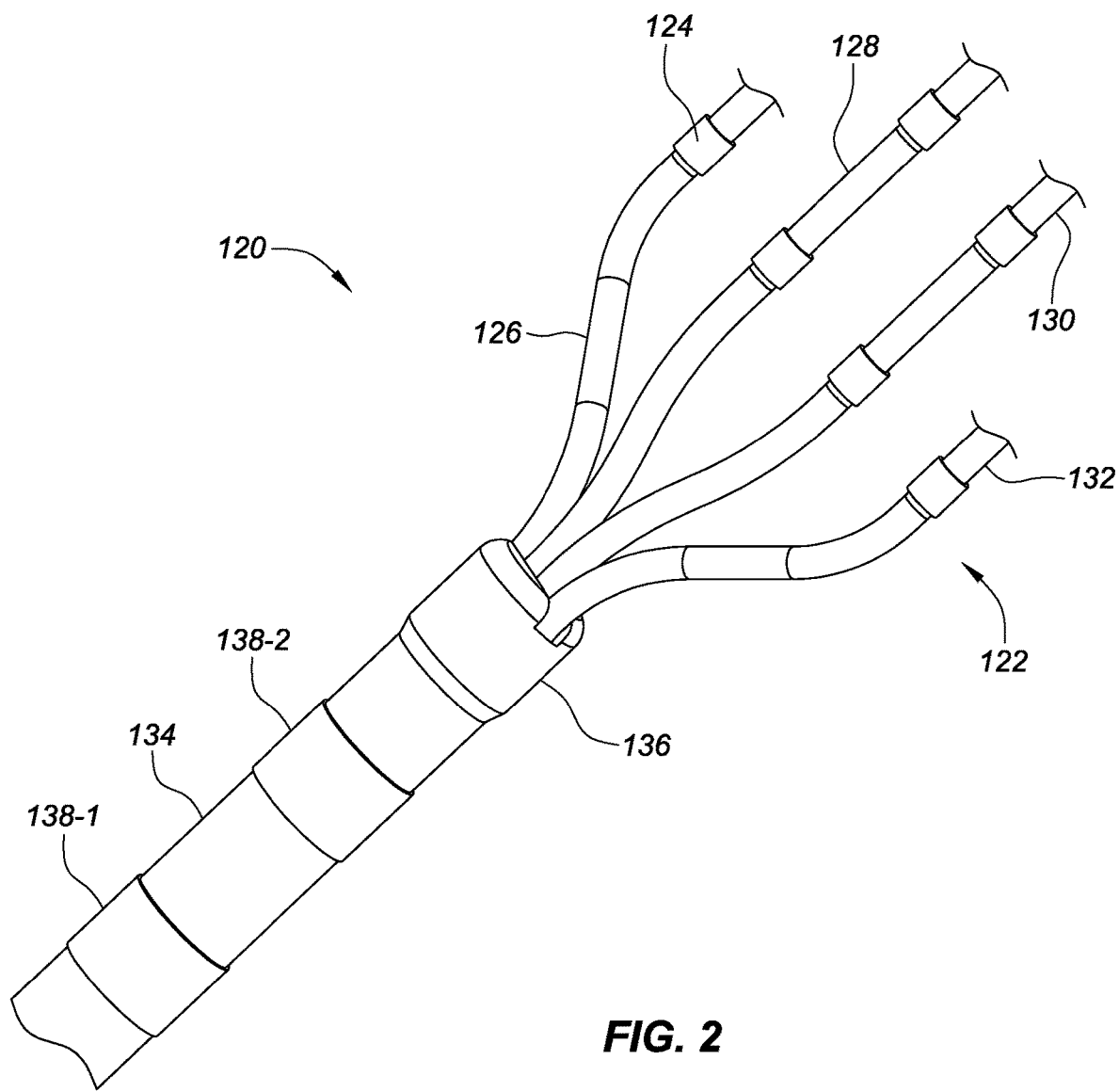
FIG. 2 is an isometric top and side view of an irrigated high density electrode catheter, according to various embodiments of the present disclosure.

FIG. 2 is an isometric top and side view of an irrigated high density electrode catheter 120, according to various embodiments of the present disclosure. In some embodiments, the irrigated high density electrode catheter 120 can include a flexible tip portion (e.g., planar array) 122 that forms a flexible array of microelectrodes 124, which are carried on longitudinally-extending arms 126, 128, 130, 132. The irrigated high density electrode catheter 120 can include a catheter shaft 134, which includes a proximal end and a distal end and extends along a longitudinal axis. In some embodiments, the distal end of the catheter shaft can include an irrigated coupler 136, which can couple the distal end of the catheter shaft 134 to a proximal end of the planar array 122. As discussed herein, the catheter shaft 134 can include one or more ring electrodes 138-1, 138-2 disposed along a length of the catheter shaft 134.

In some embodiments, the irrigated coupler 136 can include one or more irrigation ports that are configured to discharge a fluid (e.g., an irrigation fluid), which are further depicted in relation to FIGS. 3A to 4C. In some embodiments, the irrigation ports can be disposed such that they distribute fluid in a manner that substantially covers the planar array 122. In some embodiments, the irrigation ports can be configured to distribute fluid over the planar array 122 to prevent coagulation of blood or accumulation of other material on the planar array. In some embodiments, a distal portion of the planar array 122, for example, the portion of the planar array that surrounds the planar array coupler 209, depicted in FIGS. 1A and 1B can be susceptible to coagulation of blood. For instance, with reference to FIG. 6A, blood has coagulated on a distal portion of the planar array between a second inboard arm and a second outboard arm. Additionally, blood can coagulate along other portions of the planar array 122, such as around an unirrigated connector 108, as depicted in FIGS. 1A and 1B. Accordingly, embodiments of the present disclosure can be configured to distribute fluid to one or more of these portions of the planar array 122.

Figure 3A:
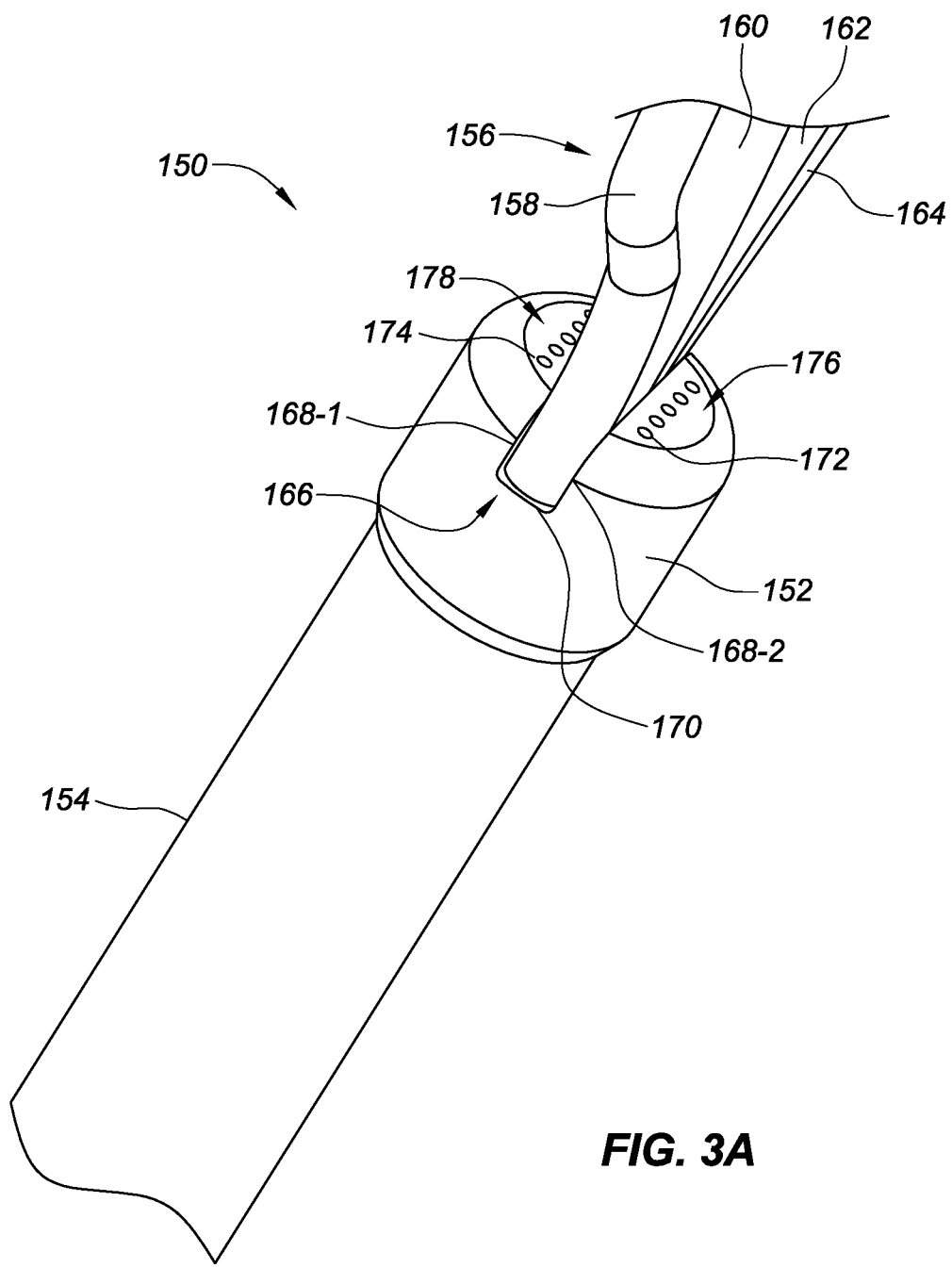
FIG. 3A is an isometric side, top, and front view of an irrigated high density electrode catheter with an irrigated coupler, according to various embodiments of the present disclosure.

FIG. 3A is an isometric side, top, and front view of an irrigated high density electrode catheter 150 with an irrigated coupler 152, according to various embodiments of the present disclosure. The irrigated coupler 152 can be disposed at a distal end of a catheter shaft 154 (e.g., elongate shaft) and can connect the flexible tip portion 156, which can include longitudinally-extending arms 158, 160, 162, 164, with the catheter shaft 154. In some embodiments, the irrigated coupler 152 and the catheter shaft 154 can extend along a longitudinal axis defined by the irrigated high density electrode catheter 150. In some embodiments, the irrigated coupler 152 can include a slot 166 that passes through a distal end of the irrigated coupler, which is defined by a first slot wall 168-1 and a second slot wall 168-2 and a base wall 170. In some embodiments, the first slot wall 168-1 and second slot wall 168-2 can extend through a distal end of the irrigated coupler 152. The first slot wall 168-1 and the second slot wall 168-2 can extend on either side of the longitudinal axis defined by the irrigated high density electrode catheter 150 can be parallel with the longitudinal axis. In some embodiments, the first slot wall 168-1 and the second slot wall 168-2 and can be parallel with one another. The base wall 170 can include an opening, which can be configured to receive the proximal ends of the longitudinally-extending arms 158, 160, 162, 164.

In some embodiments, the irrigated coupler 152 can include one or more irrigation ports 172, 174. Although more than two irrigation ports are depicted, for ease of illustration only irrigation port 172 and irrigation port 174 have been labeled in FIG. 3A. As depicted in FIG. 3A, the irrigated coupler 152 can include a first row 176 of irrigation ports disposed on a first side of the flexible tip portion 156 and a second row 178 of irrigation ports disposed on a second side of the flexible tip portion 156. Although five irrigation ports 172, 174 are depicted as being disposed on either side of the flexible tip portion 156, greater than or fewer than five irrigation ports 172, 174 can be disposed on either side of the flexible tip portion 156. Similarly, although one row of irrigation ports is depicted as being disposed on either side of the flexible tip portion 156 in the irrigated coupler 152, more than one row of irrigation ports can be disposed on either side of the flexible tip portion 156 in the irrigated coupler 152. In some embodiments, one or more rows of irrigation ports can be disposed on a first side of the irrigated coupler 152 and no irrigation ports can be disposed on the second side of irrigated coupler 152. Although the irrigation ports 172, 174 are depicted as circular, the irrigation ports 172, 174 can be of other shapes. For example, the irrigation ports 172, 174 can be ovals, squares, rectangles, triangles, etc.

Figure 3B:
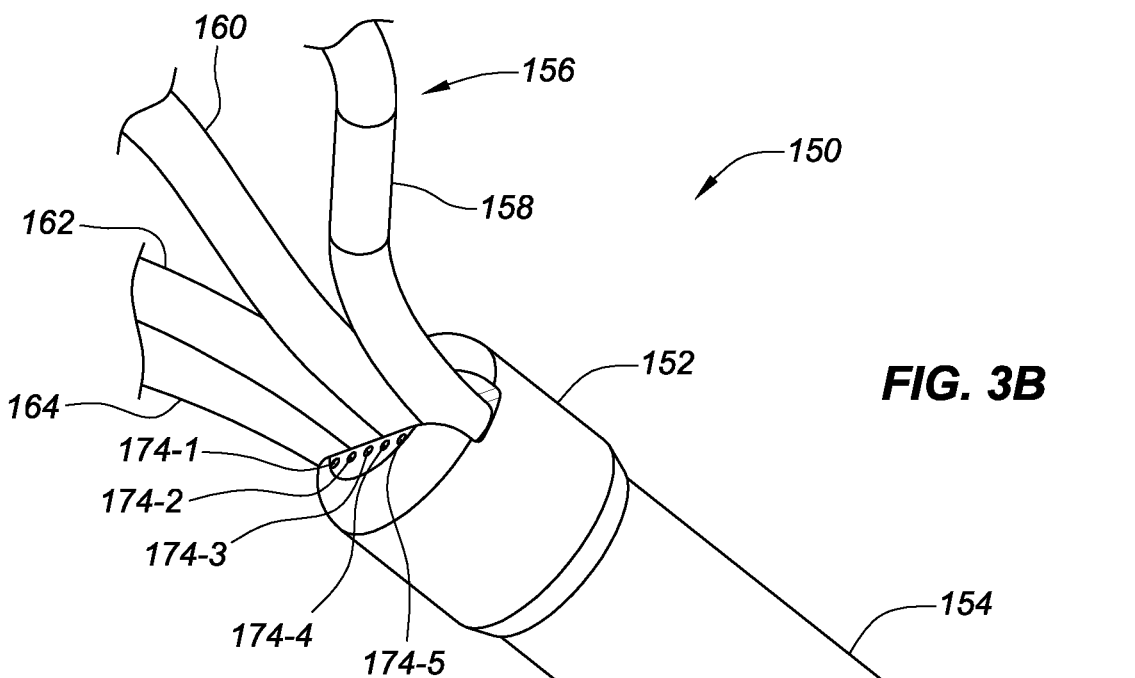
FIG. 3B is an isometric side, bottom, and front view of the irrigated high density electrode catheter with the irrigated coupler depicted in FIG. 3A, according to various embodiments of the present disclosure.

FIG. 3B is an isometric side, bottom, and front view of the irrigated high density electrode catheter 150 with the irrigated coupler 152 depicted in FIG. 3A, according to various embodiments of the present disclosure. As depicted, the second row 178 of irrigation ports can include five irrigation ports 174-1, 174-2, . . . , 174-5. In some embodiments, the irrigation ports 174-1, 174-2, . . . , 174-5 can be configured to direct a fluid flow to one or more portions of the flexible tip portion 156. The fluid flow can be a planar fan shaped fluid flow in some embodiments, which can help to ensure that fluid is distributed about a majority of the flexible tip portion 156.

Figure 3C:
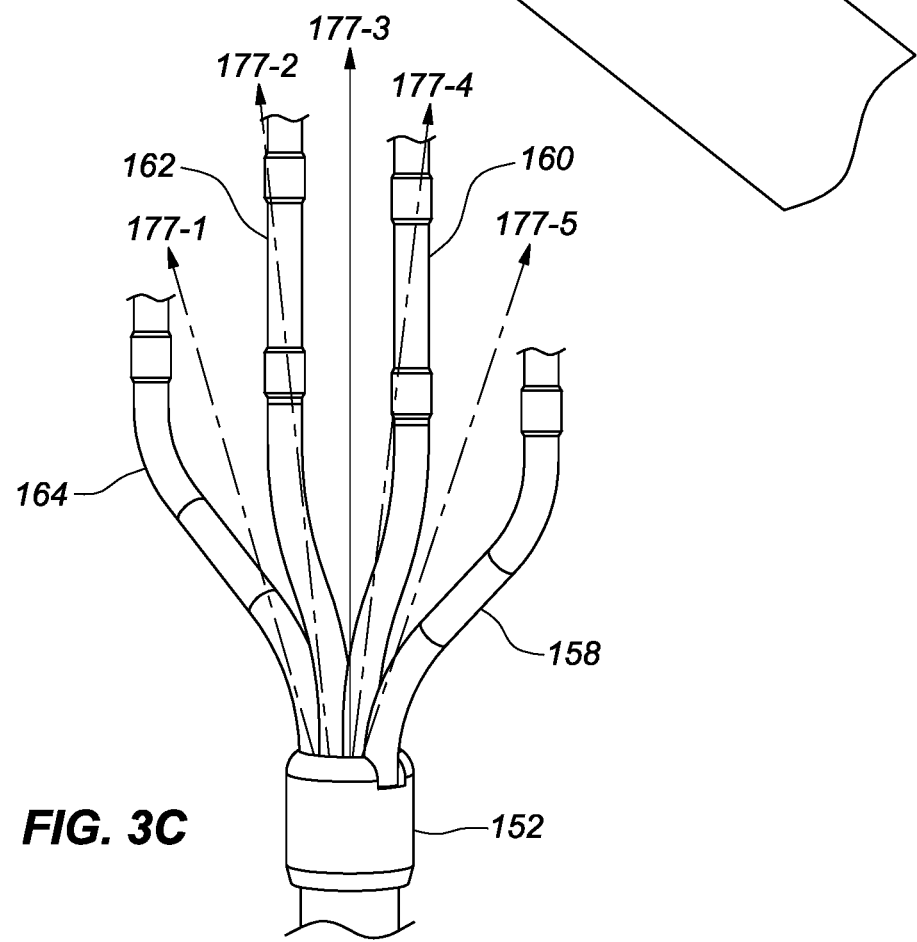
FIG. 3C is a bottom view of the irrigated high density electrode catheter with the irrigated coupler depicted in FIG. 3A and irrigation paths, according to various embodiments of the present disclosure.

FIG. 3C is a bottom view of the irrigated high density electrode catheter 150 with the irrigated coupler 152 depicted in FIG. 3A and irrigation paths 177-1, 177-2, . . . , 177-5, according to various embodiments of the present disclosure. In some embodiments, a first irrigation path 177-1 can be associated with a first irrigation port 174-1, a second irrigation path 177-2 can be associated with a second irrigation port 174-2, a third irrigation path 177-3 can be associated with a third irrigation port 174-3, a fourth irrigation path 177-4 can be associated with a fourth irrigation port 174-4, and a fifth irrigation path 177-5 can be associated with a fifth irrigation port 174-5. The irrigation ports 174-1, 174-2, . . . , 174-5 can be configured to direct fluid flow along the irrigation paths 177-1, 177-2, . . . , 177-5. For example, the third irrigation port 174-3 can include a lumen that extends through the irrigated coupler 152 parallel with a longitudinal axis of the high density electrode catheter 150 in order to direct fluid along the third irrigation path 177-3.

The second and fourth irrigation ports 174-2, 174-4 can include lumens that extend through the irrigated coupler 152 and are divergent with the longitudinal axis of the irrigated high density electrode catheter 150 in order to direct fluid along the second and fourth irrigation paths 177-2, 177-4. For instance, the lumens associated with the second and fourth irrigation ports 174-2, 174-4 can be disposed at non-zero angles with respect to the longitudinal axis. The first and fifth irrigation ports 174-1, 174-5 can include lumens that extend through the irrigated coupler 152 and are divergent with the longitudinal axis of the irrigated high density electrode catheter 150 in order to direct fluid along the first and fifth irrigation paths 177-1, 177-5. For instance, the lumens associated with the first and fifth irrigation ports 174-1, 174-5 can be disposed at non-zero angles with respect to the longitudinal axis, which are greater than those angles associated with the second and fourth irrigation ports 174-2, 174-4.

In some embodiments, the irrigated coupler 152 can be formed (e.g., molded, machined) to form the irrigation ports 174-1, 174-2, . . . , 174-5 and their respective lumens. The lumens associated with each of the irrigation ports 174-1, 174-2, . . . , 174-5 can be formed at various angles with respect to the longitudinal axis of the irrigated high density electrode catheter 150, as discussed herein. In some embodiments, one or more of the lumens associated with each of the irrigation ports 174-1, 174-2, . . . , 174-5 can be formed at non-zero angles with respect to the longitudinal axis of the irrigated high density electrode catheter 150. As previously discussed, the third irrigation port 174-3 can be formed at a non-zero angle with respect to the longitudinal axis, however, other irrigation ports can also be formed at non-zero angles with respect to the longitudinal axis of the irrigated high density electrode catheter 150. In some embodiments, all of the irrigation ports 174-1, 174-2, . . . , 174-5 can be formed at non-zero angles with respect to the longitudinal axis of the irrigated high density electrode catheter 150.

Figure 3D:
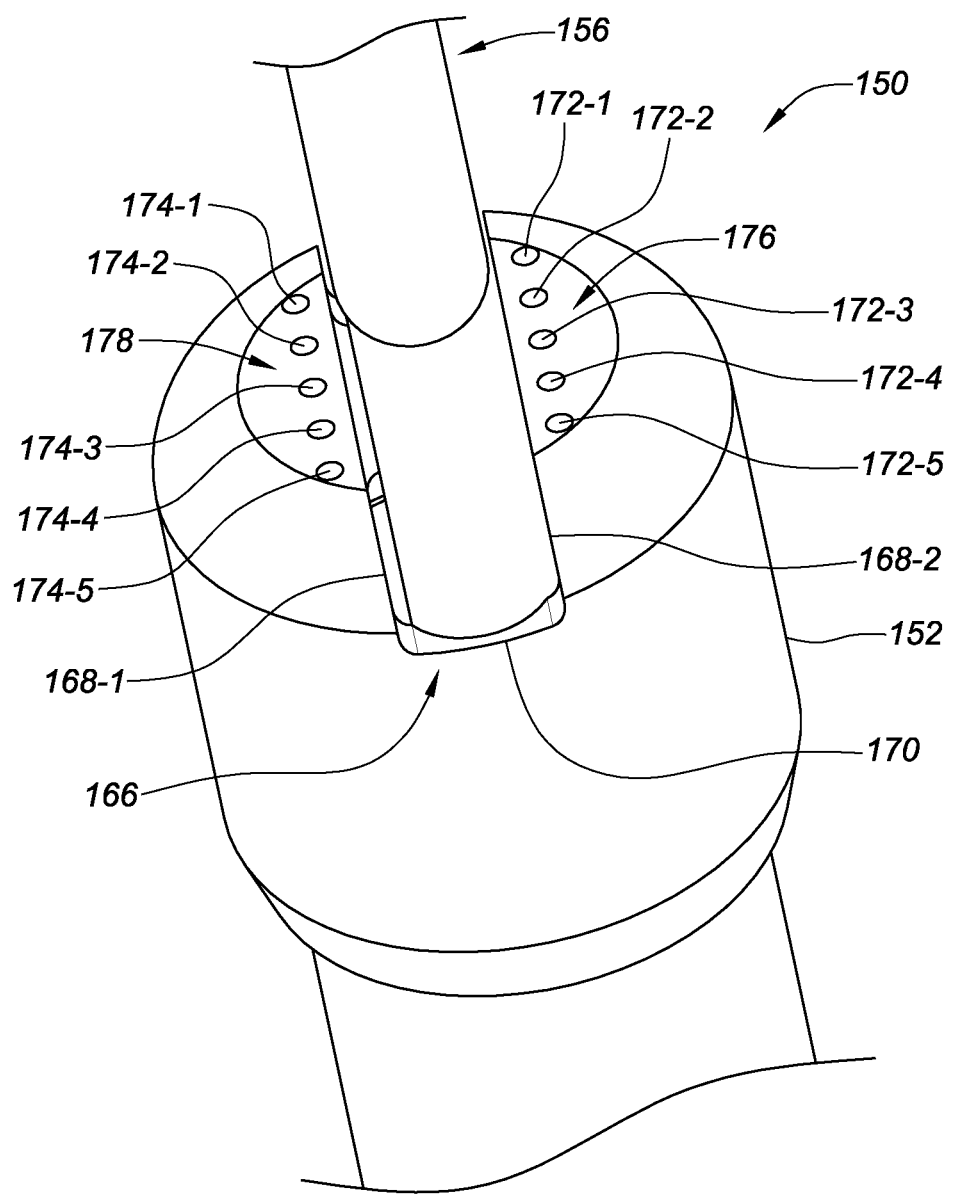
FIG. 3D is a side and front view of the irrigated high density electrode catheter with the irrigated coupler depicted in FIG. 3A that includes irrigation ports disposed in a distal end of the irrigated coupler in a first pattern, according to various embodiments of the present disclosure.

FIG. 3D is a side and front view of the irrigated high density electrode catheter 150 with the irrigated coupler 152 depicted in FIG. 3A that includes irrigation ports 172-1, 172-2, . . . , 172-5 and 174-1, 174-2, . . . , 174-5 disposed in a distal end of the irrigated coupler 152 in a first pattern, according to various embodiments of the present disclosure. As previously discussed, the irrigation ports 174-1, 174-2, . . . , 174-5, 172 can be arranged in a first row 176 and a second row 178, which are parallel to a plane formed by the flexible tip portion 156.

In some embodiments, the first slot wall 168-1 and the second slot wall 168-2 can include irrigation ports defined in the first slot wall 168-1 and the second slot wall 168-2. In some embodiments, a space can exist between each slot wall 168-1, 168-2 and the flexible tip portion 156, allowing for fluid to exit the irrigation ports and travel distally towards the distal end of the flexible tip portion 156. In some embodiments, the ports disposed on the first slot wall 168-1 and the second slot wall 168-2 can be included in place of or in addition to the irrigation ports 172-1, 172-2, . . . , 172-5 and irrigation ports 174-1, 174-2, . . . , 174-5 disposed in a distal end of the irrigated coupler 152.

Figure 4B:
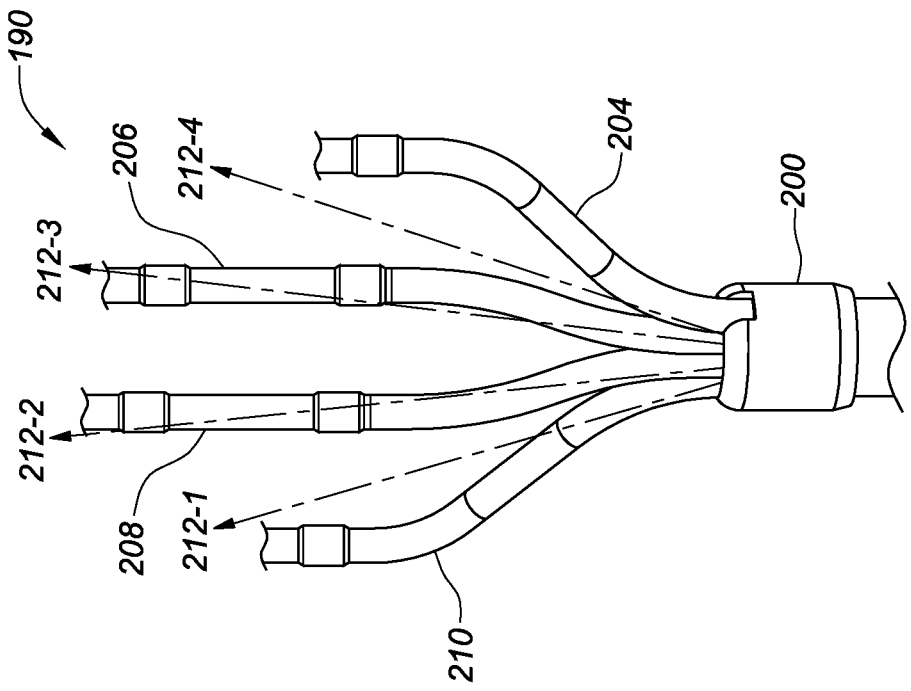
FIG. 4B is a bottom view of the irrigated high density electrode catheter with the irrigated coupler depicted in FIG. 4A and irrigation paths, according to various embodiments of the present disclosure.
Figure 4A:
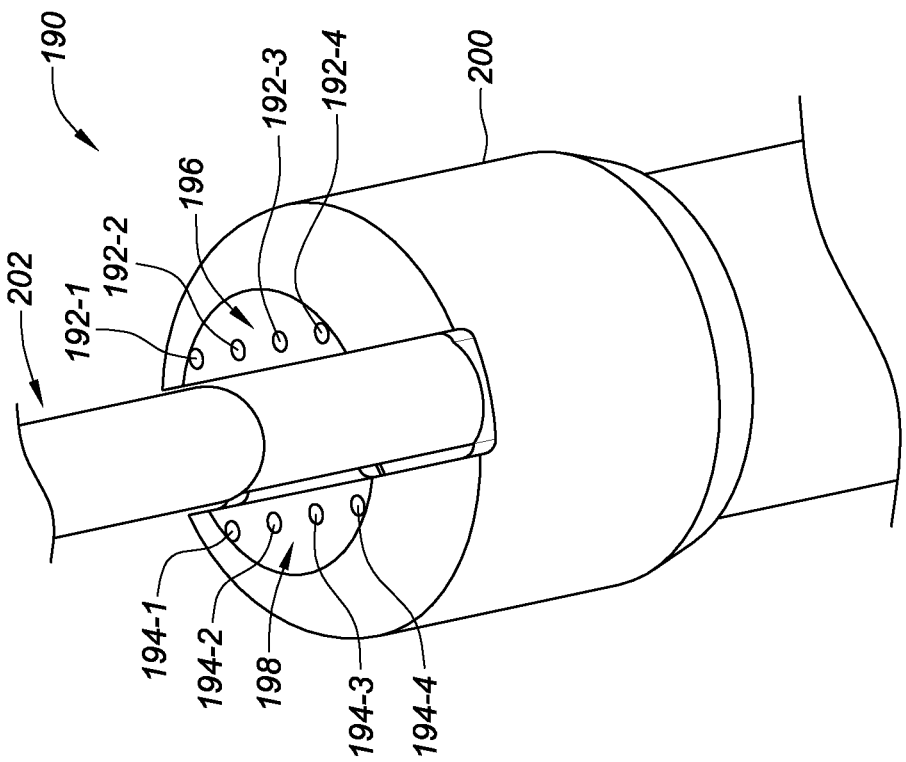
FIG. 4A is a side and front view of an irrigated high density electrode catheter with an irrigated coupler that includes irrigation ports disposed in a distal end of the irrigated coupler in a second pattern, according to various embodiments of the present disclosure.

FIG. 4A depicts a side and front view of an irrigated high density electrode catheter 190 with an irrigated coupler 200 that includes irrigation ports 192-1, 192-2, . . . , 192-4 and 194-1, 194-2, . . . , 194-4 disposed in a distal end of the irrigated coupler 200 in a second pattern, according to various embodiments of the present disclosure. As depicted, the irrigated high density electrode catheter 190 can include a first row 196 of irrigation ports 192-1, 192-2, . . . , 192-4 and a second row 198 of irrigation ports 194-1, 194-2, . . . , 194-4 disposed on the distal end and more specifically, the distal face of the irrigated coupler 200. The first and second row 196, 198 can be disposed on either side of a flexible tip portion 202, as previously discussed.

In some embodiments, the number of irrigation ports in each row can match a number of longitudinally extending arms that are included in the flexible tip portion 202. For example, although not depicted in FIG. 4A, the flexible tip portion 202 can include four longitudinally extending arms. Thus, four irrigation ports 192-1, 192-2, . . . , 192-4 can be included on a first side of the irrigated coupler 200 in a first row 196 and four irrigation ports 194-1, 194-2, . . . , 194-4 can be included on a second side of the irrigated coupler 200, in a second row 198.

In some embodiments, each of the irrigation ports 192-1, 192-2, . . . , 192-4 and 194-1, 194-2, . . . , 194-4 can be configured to direct fluid over each of the four longitudinally extending arms of the flexible tip portion 202. In a manner analogous to that discussed in relation to FIGS. 3A to 3D, each of the irrigation ports can be configured to direct fluid over a respective one of the longitudinally extending arms of the flexible tip portion 202.

FIG. 4B depicts a bottom view of the irrigated high density electrode catheter 190 with the irrigated coupler 200 depicted in FIG. 4A and irrigation paths 112-1, 212-2, . . . , 212-4, according to various embodiments of the present disclosure. In some embodiments, a first irrigation path 212-1 can be associated with a first irrigation port 194-1, a second irrigation path 212-2 can be associated with a second irrigation port 194-2, a third irrigation path 212-3 can be associated with a third irrigation port 194-3, and a fourth irrigation path 212-4 can be associated with a fourth irrigation port 194-4. The irrigation ports 194-1, 194-2, . . . , 194-4 can be configured to direct fluid flow along the irrigation paths 212-1, 212-2, . . . , 212-4.

For example, the first and fourth irrigation ports 194-1, 194-4 can include lumens that extend through the irrigated coupler 200 at angles that are divergent with respect to a longitudinal axis of the irrigated high density electrode mapping catheter 190 in order to direct fluid along the first and fourth irrigation paths 212-1, 212-4 and toward a first outboard arm 210 and second outboard arm 204, respectively. The second and third irrigation ports 194-2, 194-3 can include lumens that extend through the irrigated coupler 200 and are divergent with respect to the longitudinal axis of the irrigated high density electrode mapping catheter 190 in order to direct fluid along the second and third irrigation paths 212-2, 212-3 and toward a first inboard arm 208 and second inboard arm 206, respectively. For instance, the lumens associated with the second and third irrigation ports 194-2, 194-3 can be disposed at non-zero angles with respect to the longitudinal axis.

In some embodiments, the angles at which the second and third irrigation ports 194-2, 194-3 are disposed with respect to the longitudinal axis can be less than the angles at which the first and fourth irrigation ports 194-1, 194-4 are disposed with respect to the longitudinal axis. In some embodiments, the irrigation ports 192-1, 192-2, . . . , 192-4 and 194-1, 194-2, . . . , 194-4 can all be disposed at a non-zero angle with respect to the longitudinal axis. In some embodiments, the non-zero angle at which each of the irrigation ports 192-1, 192-2, . . . , 192-4 and 194-1, 194-2, . . . , 194-4 are disposed at can be the same. In some embodiments, each of the irrigation ports 192-1, 192-2, . . . , 192-4 and 194-1, 194-2, . . . , 194-4 can be disposed at a zero angle. As discussed herein, in some embodiments, the irrigated coupler 200 can be formed (e.g., molded, machined) to form the irrigation ports 192-1, 192-2, . . . , 192-4 and 194-1, 194-2, . . . , 194-4 and their respective lumens.

Figure 4C:
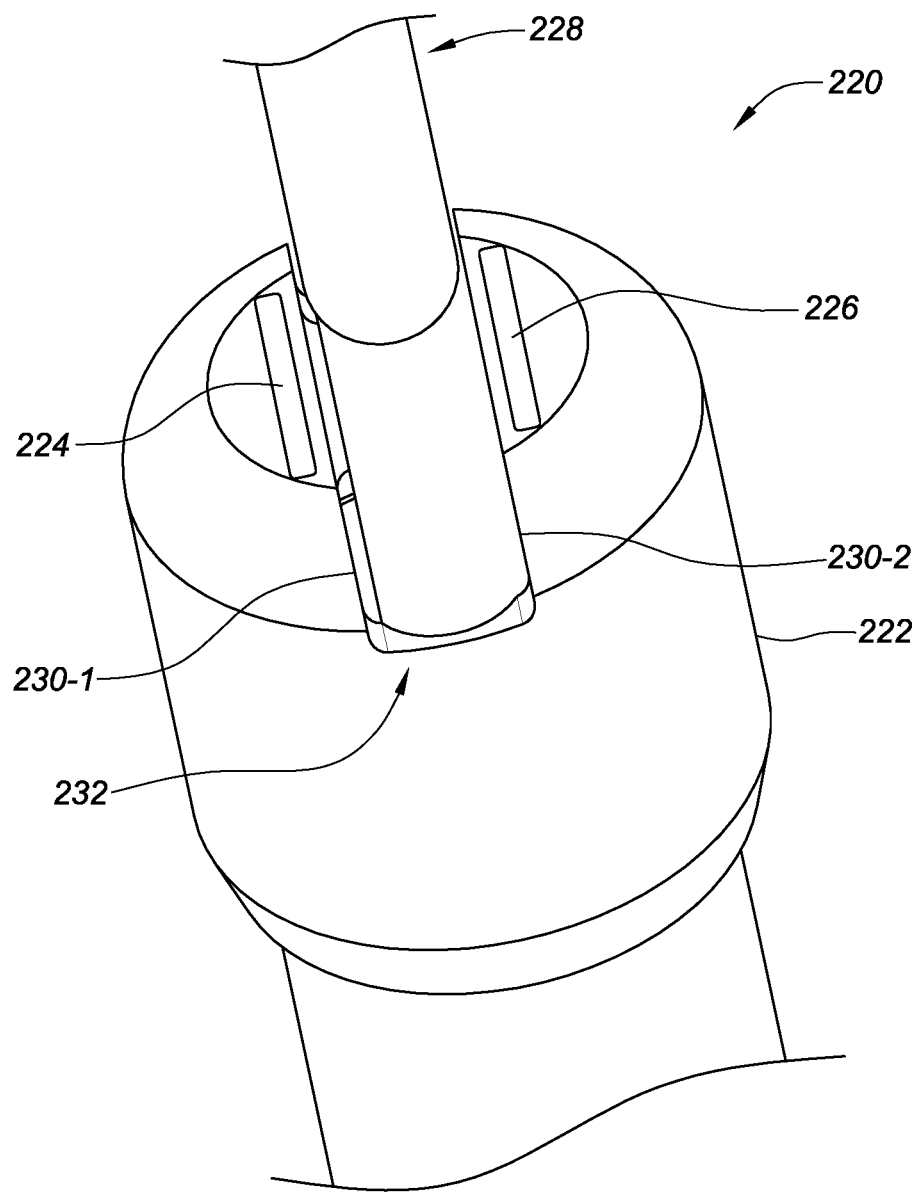
FIG. 4C is a side and front view of an irrigated high density electrode catheter with an irrigated coupler that includes irrigation ports disposed in a distal end of the irrigated coupler in a third pattern, according to various embodiments of the present disclosure.

FIG. 4C depicts a side and front view of an irrigated high density electrode mapping catheter 220 with an irrigated coupler 222 that includes irrigation ports disposed in a distal end of the irrigated coupler 222 in a third pattern, according to various embodiments of the present disclosure. As depicted, the irrigated high density electrode mapping catheter 220 can include a first elongated irrigation port 224 defined in the distal end (e.g., distal face) of the irrigated coupler 222 and on a first side of a flexible tip portion 228 of the catheter 220 and a second elongated irrigation port 226 defined in the distal end (e.g., distal face) of the irrigated coupler 222 and on a second side of the flexible tip portion 228 of the catheter 220. The elongated irrigation ports 224, 226 can extend along the distal face of the irrigated coupler 222 and can be parallel with a plane formed by the flexible tip portion 228. In some embodiments, the first and second elongated irrigation ports 224, 226 can be parallel with the first and second slot walls 230-1, 230-2 of the slot 232, respectively. In some embodiments, the elongated irrigation ports 224, 226 can be configured to distribute a planar fluid flow over the flexible tip portion 228.

Figure 4D:
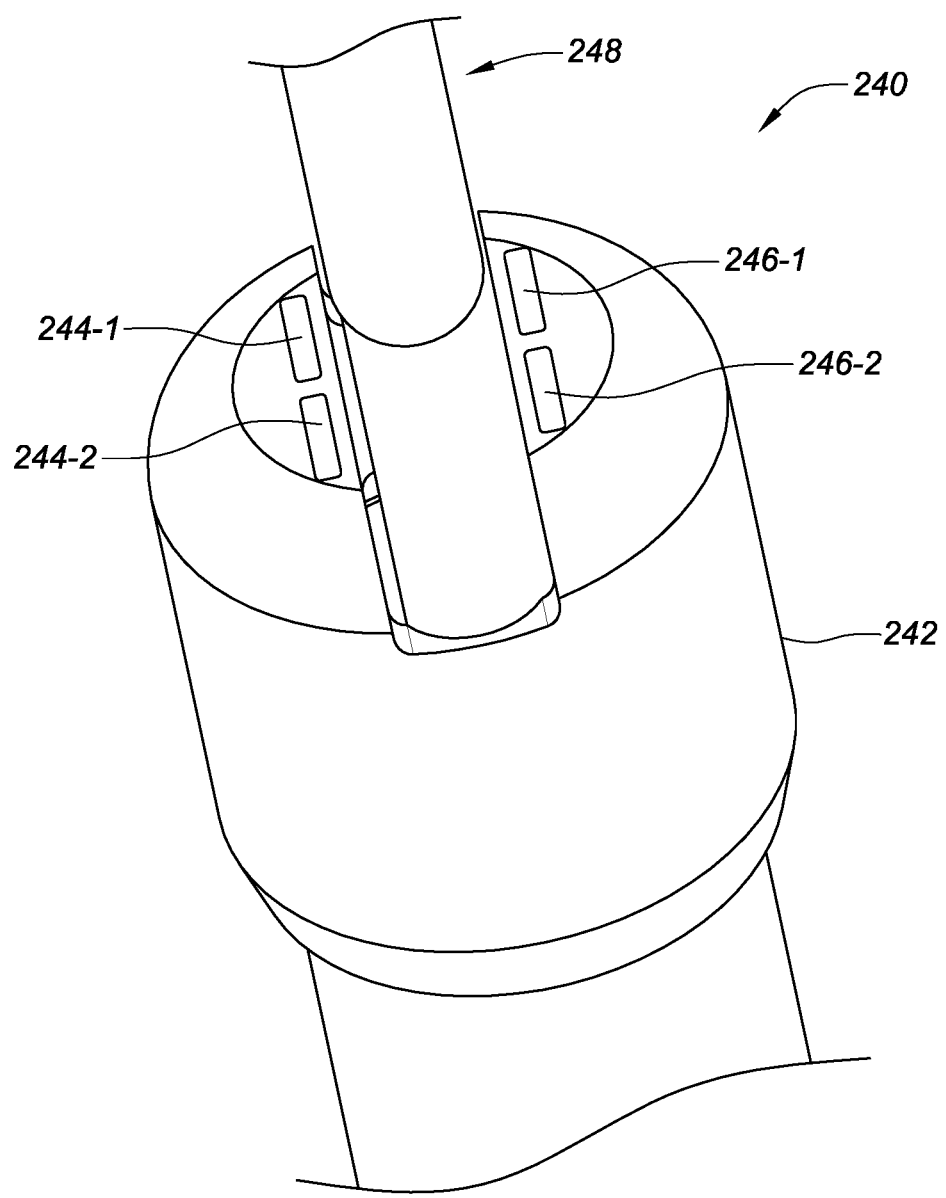
FIG. 4D is a side and front view of an irrigated high density electrode catheter with an irrigated coupler that includes irrigation ports disposed in a distal end of the irrigated coupler in a fourth pattern, according to various embodiments of the present disclosure.

FIG. 4D depicts a side and front view of an irrigated high density electrode catheter 240 with an irrigated coupler 242 that includes irrigation ports disposed in a distal end of the irrigated coupler 242 in a fourth pattern, according to various embodiments of the present disclosure. In some embodiments, the irrigation ports 244-1, 244-2, 246-1, 246-2 can be elongated, as discussed in FIG. 4C. However, as depicted in FIG. 4C, a plurality of elongated irrigation ports can be included on either side of the flexible tip portion 248. For instance, a first pair of elongated irrigation ports 244-1, 244-2 can be disposed next to one another on a first side of the flexible tip portion 248 and a second pair of elongated irrigation ports 246-1, 246-2 can be disposed next to one another on a second side of the flexible tip portion 248. Although pairs of elongated irrigation ports are disclosed in FIG. 4C, more than two irrigation ports or fewer than two irrigation ports can be disposed on either side of the flexible tip portion. In some embodiments, the elongated irrigation ports 244-1, 244-2 on the first side can be longitudinally aligned with one another and the elongated irrigation ports 246-1, 246-2 on the second side can be longitudinally aligned with one another, as depicted in FIG. 4C. In some embodiments, the elongated irrigation ports 244-1, 244-2, 246-1, 246-2 can aid in producing a planar flow of fluid, which can be distributed across the flexible tip portion 248.

In some embodiments, in a manner analogous to that discussed in relation to FIGS. 3C and 4B, the irrigation ports 244-1, 244-2, 246-1, 246-2 can include lumens, which can be disposed at non-zero angles with respect to a longitudinal axis formed by the irrigated high density electrode catheter 240. Accordingly, the irrigation ports 244-1, 244-2, 246-1, 246-2 can direct fluid towards targeted portions of the flexible tip portion 248.

Figure 5:
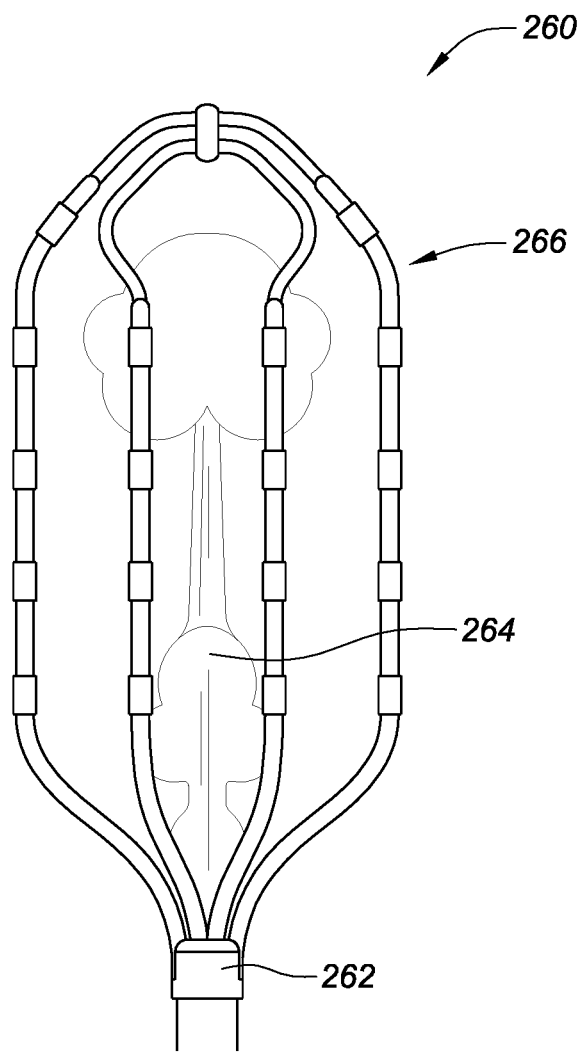
FIG. 5 is a top view of an irrigated high density electrode catheter with an irrigated coupler that is discharging a fluid, according to various embodiments of the present disclosure.

FIG. 5 depicts a top view of an irrigated high density electrode catheter 260 with an irrigated coupler 262 that is discharging a fluid 264, according to various embodiments of the present disclosure. The irrigated high density electrode catheter 260 can include irrigation ports, as discussed herein, which can be configured to discharge fluid over a flexible tip portion 266 of the irrigated high density electrode catheter 260. As depicted, the fluid is depicted as being discharged over the flexible tip portion. As further depicted in FIG. 5, the flow rate of fluid that is discharged through the irrigation ports of the irrigated coupler 262 is 2 milliliters per minute (ml/min), however, this flow rate is provided for example purposes only and the flow rate can be greater than or less than 2 ml/min.

Figure 6B:
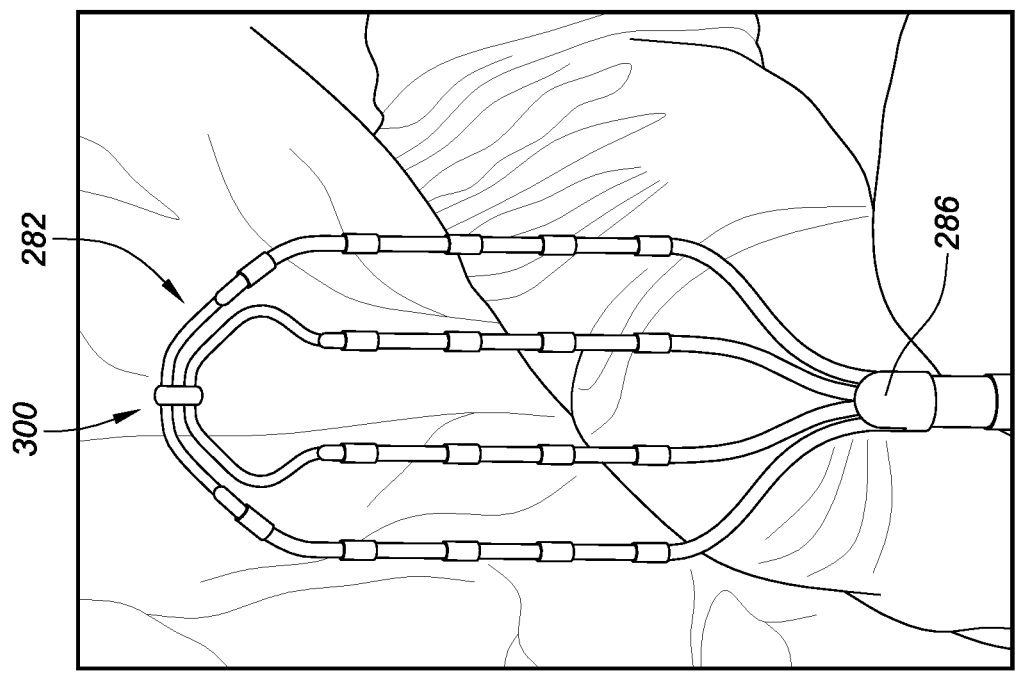
FIG. 6B is a top view of an irrigated high density electrode catheter with an irrigated coupler after performance of a medical procedure, according to various embodiments of the present disclosure.
Figure 6A:
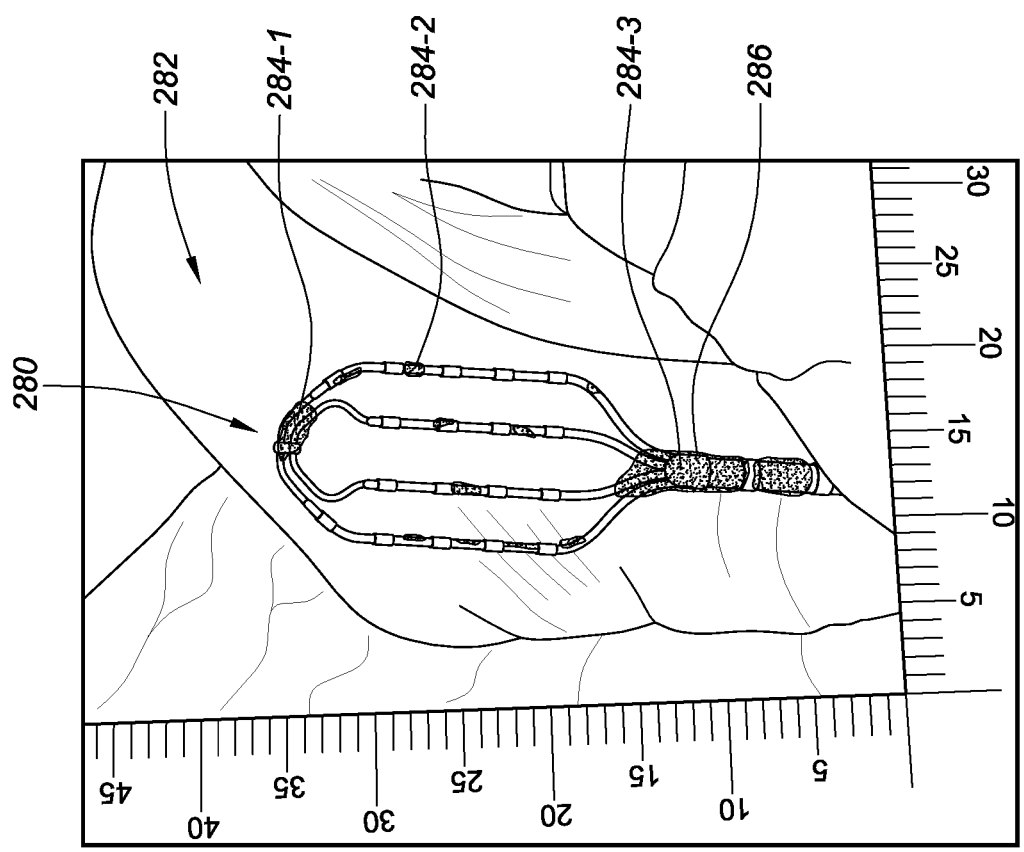
FIG. 6A is a top view of a non-irrigated high density electrode catheter after performance of a medical procedure, according to various embodiments of the present disclosure.

FIG. 6A depicts a top view of a non-irrigated high density electrode catheter 280 after performance of a medical procedure, according to various embodiments of the present disclosure. The non-irrigated high density electrode catheter 280 includes a flexible tip portion 282, which is depicted as having coagulated blood 284-1 present on the distal end of the flexible tip portion 282. In addition, coagulated blood 284-2 is depicted as being present on one or more of the microelectrodes of the flexible tip portion 282 and also depicts coagulated blood 284-3 as being present on a non-irrigated coupler 286 of the electrode catheter 280.

FIG. 6B depicts a top view of an irrigated high density electrode catheter 300 with an irrigated coupler 286 after performance of a medical procedure, according to various embodiments of the present disclosure. As depicted, the irrigated high density electrode catheter 300 is generally free of coagulated blood, in contrast to the non-irrigated coupler 286 of the electrode catheter 280 depicted in FIG. 6A.

Figure 7:
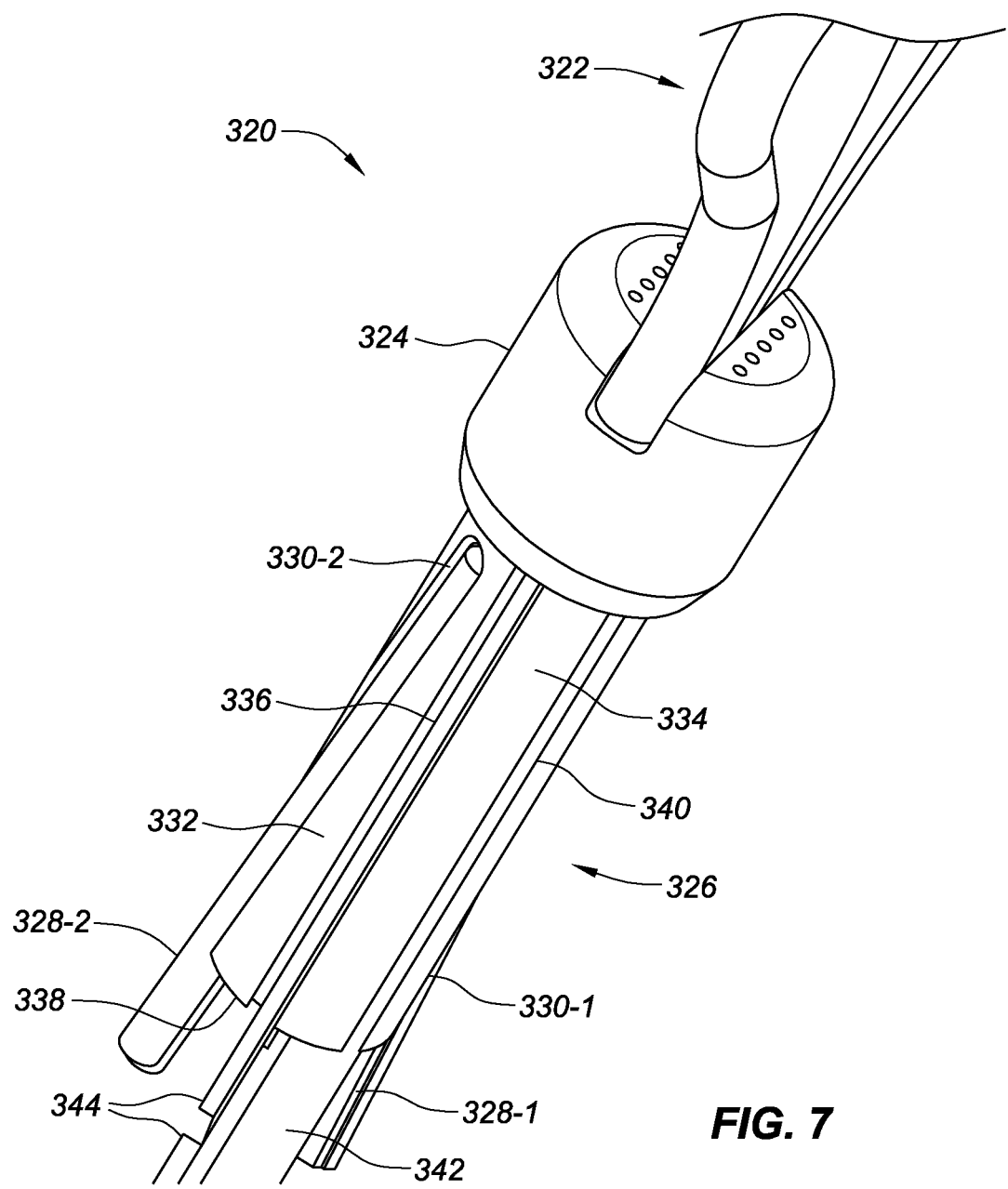
FIG. 7 is an isometric side, top, and front view of an irrigated high density electrode catheter that includes a flexible tip portion, with an irrigated coupler and connective stem, according to various embodiments of the present disclosure.

FIG. 7 depicts an isometric side, top, and front view of an irrigated high density electrode catheter 320 that includes a flexible tip portion 322, with an irrigated coupler 324 and connective stem 326, according to various embodiments of the present disclosure. The irrigated coupler 324 can include irrigation ports, as discussed herein. In some embodiments, a proximal end of the irrigated coupler 324 can be connected with a distal end of the connective stem 326. In some embodiments, the connective stem 326 can be inserted into a distal end of a catheter shaft and connected with the catheter shaft. For example, an outer diameter of the connective stem 326 can be less than an inner diameter of the catheter shaft.

In some embodiments, the connective stem 326 can be configured to hold a six degree of freedom (DOF) sensor assembly, which includes a pair of magnetic position sensors 328-1, 328-2. In some embodiments, each of the magnetic position sensors 328-1, 328-2 can be disposed about a respective longitudinal axis. In some embodiments, each of the magnetic position sensors 328-1, 328-2 can include a coil wound around a longitudinal axis (e.g., sensor longitudinal axis). In an example, the first magnetic position sensor 328-1 can include a coil wound about a first sensor longitudinal axis and the second magnetic position sensor 328-2 can include a coil wound about a second sensor longitudinal axis, as further discussed herein. In some embodiments, the magnetic position sensors 328-1, 328-2 can be elongated, as depicted in FIG. 7.

The connective stem 326 can include sensor grooves 330-1, 330-2 formed in an outer portion of the connective stem 326, in which the six degree of freedom sensor assembly can be placed. The magnetic position sensors 328-1, 328-2 can each be offset by a particular angle from a longitudinal axis formed by the connective stem 326. Each sensor can be offset by the particular angle with respect to the longitudinal axis formed by the connective stem 326, causing the two five DOF sensors together to form a six DOF sensor assembly, which is able to sense position (e.g., x, y, z) and orientation (e.g., roll, pitch, yaw). For example, because the two magnetic position sensors 328-1, 328-2 are at a slight angle with respect to one another, they can be at different rotational angles with respect to the axis of the magnetic field. Thus, as the magnetic position sensors 328-1, 328-2 rotate in any angle, the difference in voltage, and also their vectors can be picked up and consequently, a 6 DOF sensor can be created.

In some embodiments, the sensor grooves 330-1, 330-2 can be offset by a particular angle with respect to the longitudinal axis formed by the connective stem 326 and can be diametrically opposed to one another. By doing so, the magnetic position sensors 328-1, 328-2 can be inserted into the sensor grooves 330-1, 330-2 and thus set at an appropriate angle with respect to one another to enable the two five DOF magnetic position sensors 328-1, 328-2 to act as a six DOF sensor assembly. In an example, the first sensor groove 330-1 can be disposed at a positive 5 degree angle with respect to the longitudinal axis formed by the connective stem 326 and the second sensor groove 330-2 can be disposed at a negative 5 degree angle with respect to the longitudinal axis formed by the connective stem 326 to create a 10 degree separation between the magnetic position sensors 328-1, 328-2.

In some embodiments, the degree of separation between the magnetic position sensors 328-1, 328-2 and sensor grooves 330-1, 330-2 can be in a range from 1 degree to 20 degrees, 5 degrees to 15 degrees, and preferably from 10 degrees to 12 degrees. However, the degree of separation can be less than 1 degree or over 20 degrees. In some embodiments, each of the magnetic position sensors 328-1, 328-2 and sensor grooves 330-1, 330-2 can be disposed at a same angle with respect to the longitudinal axis formed by the connective stem 326. In some embodiments, one of the magnetic position sensors 328-1, 328-2 and sensor grooves 330-1, 330-2 can be disposed at a greater angle than the other magnetic position sensors 328-1, 328-2 and sensor grooves 330-1, 330-2, however, the degree of separation between the magnetic position sensors 328-1, 328-2 and sensor grooves 330-1, 330-2 can still be within the ranges discussed herein.

In some embodiments, the connective stem 326 can be divided along the longitudinal axis of the connective stem 326 to form a top connective stem portion 332 and a bottom connective stem portion 334. In some embodiments, a seam 336 can extend between the top connective stem portion 332 and the bottom connective stem portion 334.

The connective stem 326 can include a stem key 338 in some embodiments and the irrigated coupler 324 can include a corresponding recessed key area, further depicted herein, which is configured to accept the stem key 338. The stem key 338 and the corresponding recessed key area can aid in alignment between the connective stem 326 and the irrigated coupler 324. In some embodiments, an inner surface of the catheter shaft, which is configured to accept connective stem 326 can include a recessed shaft key area that is configured to accept the stem key 338 to aid in alignment between the connective stem 326 and the catheter shaft.

In some embodiments, the connective stem 326 can define a longitudinal irrigation lumen 340, which can be configured for fluid flow. The longitudinal irrigation lumen 340 can be contained within the connective stem 326 and/or the irrigation lumen 340 can include a longitudinal slit along an outer surface of the connective stem 326 that exposes the interior of the longitudinal irrigation lumen 340 to an exterior of the connective stem 326. In some embodiments, an irrigation tube 342 can extend through a portion of the longitudinal irrigation lumen 340. The longitudinal irrigation lumen 340 and/or irrigation tube 342 can be configured to provide a fluid flow to the irrigation ports of the irrigated coupler 324.

The connective stem 326 can be configured to house an understructure that forms the longitudinally-extending arms of the flexible tip portion 322. As depicted in FIG. 7, a first outboard mounting arm 344 of an outboard understructure of the flexible tip portion 322 can be contained between the top connective stem portion 332 and the bottom connective stem portion 334.

Figure 8A:
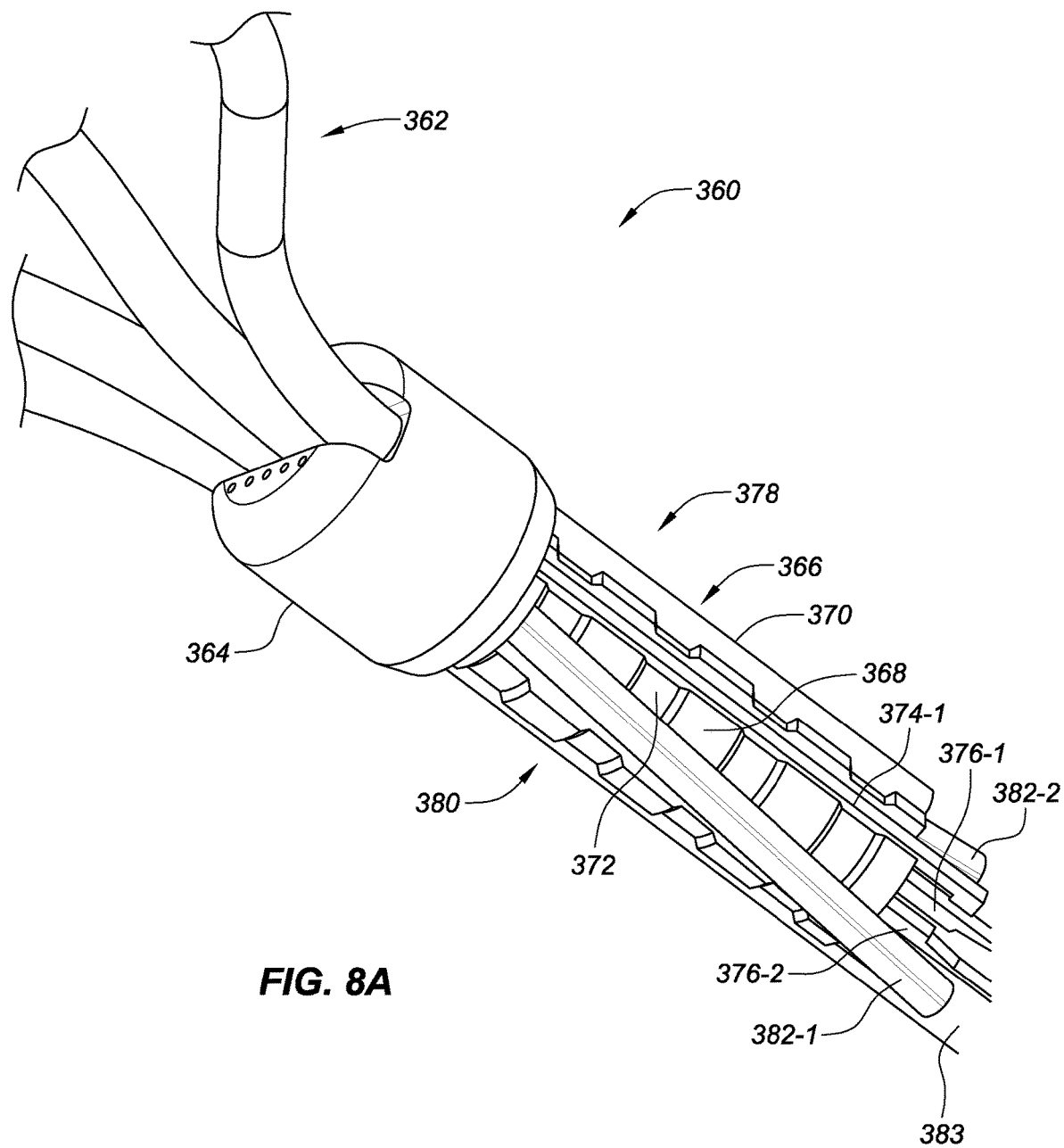
FIG. 8A is an isometric side, bottom, and front view of an irrigated high density electrode catheter that includes a flexible tip portion, with an irrigated coupler and ribbed connective stem, according to various embodiments of the present disclosure.

FIG. 8A depicts an isometric side, bottom, and front view of an irrigated high density electrode catheter 360 that includes a flexible tip portion 362, with an irrigated coupler 364 and ribbed connective stem 366, according to various embodiments of the present disclosure. The embodiments disclosed in FIG. 8A can include the same features as those discussed in relation to FIG. 7, with the addition of ribs 368 that circumferentially extend around the ribbed connective stem 366. In some embodiments, the ribs 368 can circumferentially extend around a body of the ribbed connective stem 366, up to the stem key 370. A radial height of the ribs can be less than, equal to, or greater than a radial height of the stem key 370. In some embodiments, the ribs 368 can define circumferential grooves 372 that extend around the body of the ribbed connective stem 366 between the ribs 368. The radial height of the ribs 368 can be configured to provide a diameter of the ribbed connective stem 366, which is less than a diameter of a catheter shaft, which accepts the ribbed connective stem 366. In some embodiments, the grooves can reduce a friction associated with inserting the ribbed connective stem 366 into a lumen defined by the catheter shaft, and/or provide an area for an adhesive to collect when the ribbed connective stem 366 is inserted into the lumen defined by the catheter shaft.

As depicted, the connective stem 366 can include a first five DOF magnetic position sensor 382-1, second five DOF magnetic position sensor 382-2, and an irrigation tube 383, as discussed in relation to FIG. 7. As further discussed in relation to FIG. 7, the connective stem 366 can include a top connective stem portion 380 and a bottom connective stem portion 378 that contain an understructure that forms the longitudinally-extending arms of the flexible tip portion 362. For example, the connective stem 366 can house an outboard understructure that includes a first outboard mounting arm 374-1 and a second outboard mounting arm, which is depicted in FIG. 8B, and an inboard understructure that includes a first inboard mounting arm 376-1 and a second inboard mounting arm 376-2.

Figure 8B:
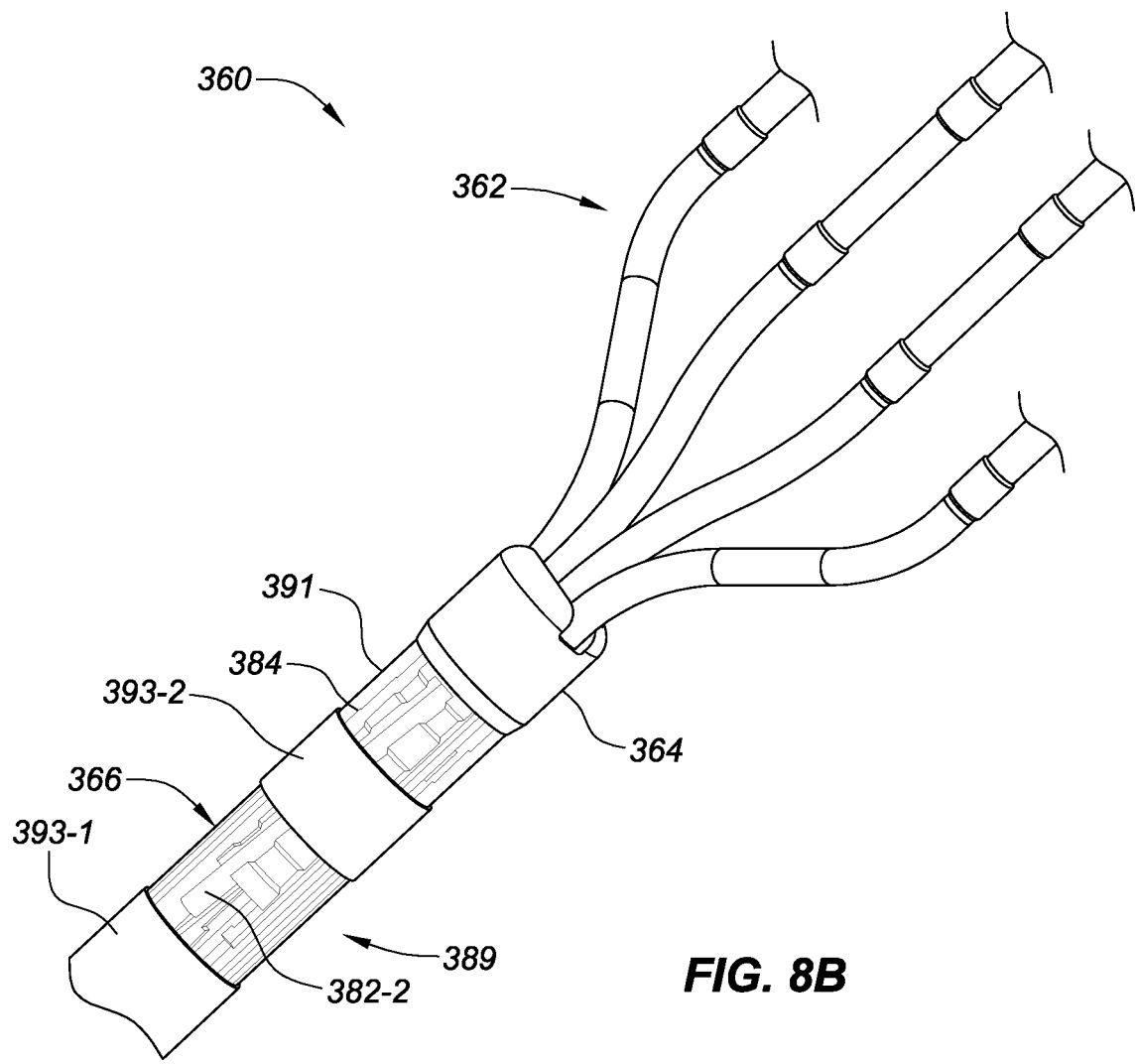
FIG. 8B is an isometric top and side view of the irrigated high density electrode mapping catheter in FIG. 8A inserted into the distal end of a catheter shaft, according to various embodiments of the present disclosure.

FIG. 8B depicts an isometric top and side view of the irrigated high density electrode catheter 360 in FIG. 8A inserted into the distal end of a catheter shaft 389, according to various embodiments of the present disclosure. In some embodiments, the catheter shaft 389 can include an elongate shaft that extends along a shaft longitudinal axis and can include a shaft proximal end and a shaft distal end. In some embodiments, and as depicted in FIG. 8B, the irrigated high density electrode catheter 360 can be inserted into the distal end of the catheter shaft 389. For example, the ribbed connective stem 366, which houses the irrigation tube 383 and the first and second five DOF magnetic sensors 382-1, 382-2 can be inserted into a lumen formed in the distal end of the catheter shaft 389. The catheter shaft 389 can be formed from a material 391 that is flexible, rigid, and/or semi-rigid in some embodiments. As depicted in FIG. 8B, the flexible material 391 can be semi-translucent.

In some embodiments, the catheter shaft 389 can be inserted up to a proximal end of the irrigated coupler 364, into the irrigated coupler 364, or around the irrigated coupler 364. As further discussed in relation to FIG. 2, the catheter shaft 134 can include one or more ring electrodes 393-1, 393-2 disposed along a length of the catheter shaft 389.

FIG. 8B depicts an isometric side, top, and rear view of the irrigated high density electrode catheter 360 depicted in FIG. 8A that includes a flexible tip portion 362, with an irrigated coupler 364 and top connective stem portion 380, according to various embodiments of the present disclosure. In some embodiments, the top connective stem portion 380 can include a planar inner surface. In some embodiments, a plurality of longitudinal ridges 384-1, 384-2, 384-3 can extend perpendicular to the planar inner surface of the top connective stem portion 380.

FIG. 8C is an isometric side, bottom, and rear view of the irrigated high density electrode catheter 360 depicted in FIGS. 8A and 8B that includes a flexible tip portion 362, with an irrigated coupler 364 and bottom connective stem portion 378, according to various embodiments of the present disclosure. As depicted, the bottom connective stem portion 378 can include a five DOF magnetic position sensor 382-1, as discussed in relation to FIG. 7. FIG. 8C depicts an understructure that forms the longitudinally-extending arms of the flexible tip portion 362. For example, the bottom connective stem portion 378 can house an outboard understructure that includes a first outboard mounting arm 374-1 and a second outboard mounting arm 374-2, and an inboard understructure that includes a first inboard mounting arm 376-1 and a second inboard mounting arm 376-2.

The bottom connective stem portion 378 and the top connective stem portion 380 (FIG. 8A) can together form the connective stem 366. Portions of the outboard and/or inboard understructure that are located distally with respect to the connective stem 366 can be disposed within a housing (e.g., a tube, covering). For example, with reference to the second outboard mounting arm 374-2, the second outboard mounting arm 374-2 can be disposed within a tube 412. In some embodiments, the bottom connective stem portion 378 and the top connective stem portion 380 can include opposing complementary planar faces. Upon assembly of the bottom connective stem portion 378 and the top connective stem portion 380, the connective stem portions 378, 380 can form the connective stem 366.

In some embodiments, as depicted in FIG. 8C, the bottom connective stem portion 378 and/or the top connective stem portion 380 can define longitudinally extending slots (e.g., channels) that extend along one or more of the complementary planar faces of the bottom connective stem portion 378 and the top connective stem portion 380. The longitudinally extending slots can be defined by longitudinally extending ridges 384-1, 384-2, . . . , 384-9, in some embodiments, hereinafter referred to in the plural as longitudinally extending ridges 384. The longitudinally extending ridges can extend upward and transversely to the planar face of the bottom connective stem portion 378 and/or the top connective stem portion 380. In some embodiments, as depicted in FIG. 8C, the first outboard mounting arm 374-1, second outboard mounting arm 374-2, first inboard mounting arm 376-1, and second inboard mounting arm 376-2 can be disposed between each one of and/or adjacent to the longitudinally extending ridges 384.

In some embodiments, three sets of longitudinally extending ridges 384 are depicted. For example, a first set of longitudinally extending ridges 384-1, 384-2, 384-3 are disposed between the first outboard mounting arm 374-1 and the first inboard mounting arm 376-1, a second set of longitudinally extending ridges 384-4, 384-5, 384-6 are disposed between the first inboard mounting arm 376-1 and the second inboard mounting arm 376-2, and a third set of longitudinally extending ridges 384-7, 384-8, 384-9 are disposed between the second outboard mounting arm 374-2 and the second inboard mounting arm 376-2.

In some embodiments, the longitudinally extending ridges 384 can be divided into a distal set of longitudinally extending ridges 384-1, 384-4, 384-7, a middle set of longitudinally extending ridges 384-2, 384-5, 384-8, and a proximal set of longitudinally extending ridges 384-3, 384-6, 384-9. In some embodiments, the distal set of longitudinally extending ridges 384-1, 384-4, 384-7 and the middle set of longitudinally extending ridges 384-2, 384-5, 384-8 can define distal lateral mounting gaps 386-1, 386-2, 386-3 extending therebetween, and the proximal set of longitudinally extending ridges 384-3, 384-6, 384-9 and the middle set of longitudinally extending ridges 384-2, 384-5, 384-8 can define proximal lateral mounting gaps 386-4, 386-5, 386-6 extending therebetween. In some embodiments, although three rows of longitudinally extending ridges 384 are depicted, as well as proximal, middle, and distal sets of longitudinally extending ridges, fewer or greater than three rows and/or three sets can be included in embodiments of the present disclosure.

In some embodiments, each of the inboard mounting arms 376-1, 376-2 can include an inboard frame lock tab 388-1, 388-2, as discussed in US application Ser. No. 15/331,369, which is hereby incorporated by reference as though fully set forth herein. The first inboard mounting arm 376-1 can be disposed between a first row of longitudinally extending ridges 384-1, 384-2, 384-3 and the second row of longitudinally extending ridges 384-4, 384-5, 384-6 and the second inboard mounting arm 376-2 can be disposed between a second row of longitudinally extending ridges 384-4, 384-5, 384-6 and the third row of longitudinally extending ridges 384-7, 384-8, 384-9. A first inboard frame lock tab 388-1 can be included on the first inboard mounting arm 376-1 and can be disposed in a center proximal mounting gap 386-5. A second inboard frame lock tab 388-2 can be included on the second inboard mounting arm 376-2 and can be disposed in a center distal mounting gap 386-2. Thus, the frame lock tabs 388-1, 388-2 can be locked into place via the center proximal mounting gap 386-5 and the center distal mounting gap 386-2.

Additionally, the first outboard mounting arm 374-1 can include outboard frame lock tabs 390-1, 390-2 and the second outboard mounting arm 374-2 can include outboard frame lock tabs 390-3, 390-4. The outboard frame lock tabs 390-1, 390-2 can be disposed in a right distal mounting gap 386-1 and a right proximal mounting gap 386-4, respectively. Likewise, the outboard frame lock tabs 390-3, 390-4 can be disposed in a left distal mounting gap 386-3 and a left proximal mounting gap 386-6, respectively. Accordingly, the first inboard mounting arm 376-1 and the second inboard mounting arm 376-2, as well as the first outboard mounting arm 374-1 and second outboard mounting arm 374-2, can be locked to the bottom connective stem portion 378 via the frame lock tabs.

In some embodiments, the bottom connective stem portion 378 can include an irrigation cross-over 392. In some embodiments, the top connective stem portion 380 can include an irrigation lumen that extends longitudinally through the top connective stem portion 380 and is fluidly coupled with a cross-over lumen 394 defined by the irrigation cross-over 392. In some embodiments, the irrigation lumen can be a lumen defined by the top connective stem portion 380 and/or can be an irrigation tube 383 (FIG. 8A) that is attached to the top connective stem portion 380. As further discussed herein, the irrigation lumen can provide a fluid to a first side of the irrigated coupler 364. The fluid can be expelled from irrigation ports defined by the irrigated coupler 364 and can be transferred to another side of the irrigated coupler via the cross-over lumen 394. For example, the irrigation cross-over lumen 394 can provide fluid to an opposite side of the irrigated coupler 364.

FIG. 8D is an isometric side, bottom, and rear view of the irrigated high density electrode catheter 360 depicted in FIGS. 8A-8C that includes a flexible tip portion 362, and bottom connective stem portion 378 that includes an irrigation cross-over 392, according to various embodiments of the present disclosure. As previously discussed, the irrigation cross-over 392 can define a cross-over lumen 394. In some embodiments, the irrigation cross-over 392 can extend upward and perpendicular to a planar face of the bottom connective stem portion 378, as depicted. In some embodiments, the irrigation cross-over 392 can include a barrel portion 402, which defines the cross-over lumen 394. As previously discussed, the cross-over lumen 394 can be in fluid communication with an irrigation lumen such as the irrigation tube 383 (FIG. 8A).

In some embodiments, the first inboard mounting arm 376-1 and/or the second inboard mounting arm 376-2 can include barrel cutouts 404-1, 404-2. For example, the first inboard mounting arm 376-1 can define a first barrel cutout 404-1 and the second inboard mounting arm 376-2 can define a second barrel cutout 404-2. The first barrel cutout 404-1 and the second barrel cutout 404-2 can allow for the barrel portion 402 to extend upward past the first inboard mounting arm 376-1 and the second inboard mounting arm 376-2.

Figure 8E:
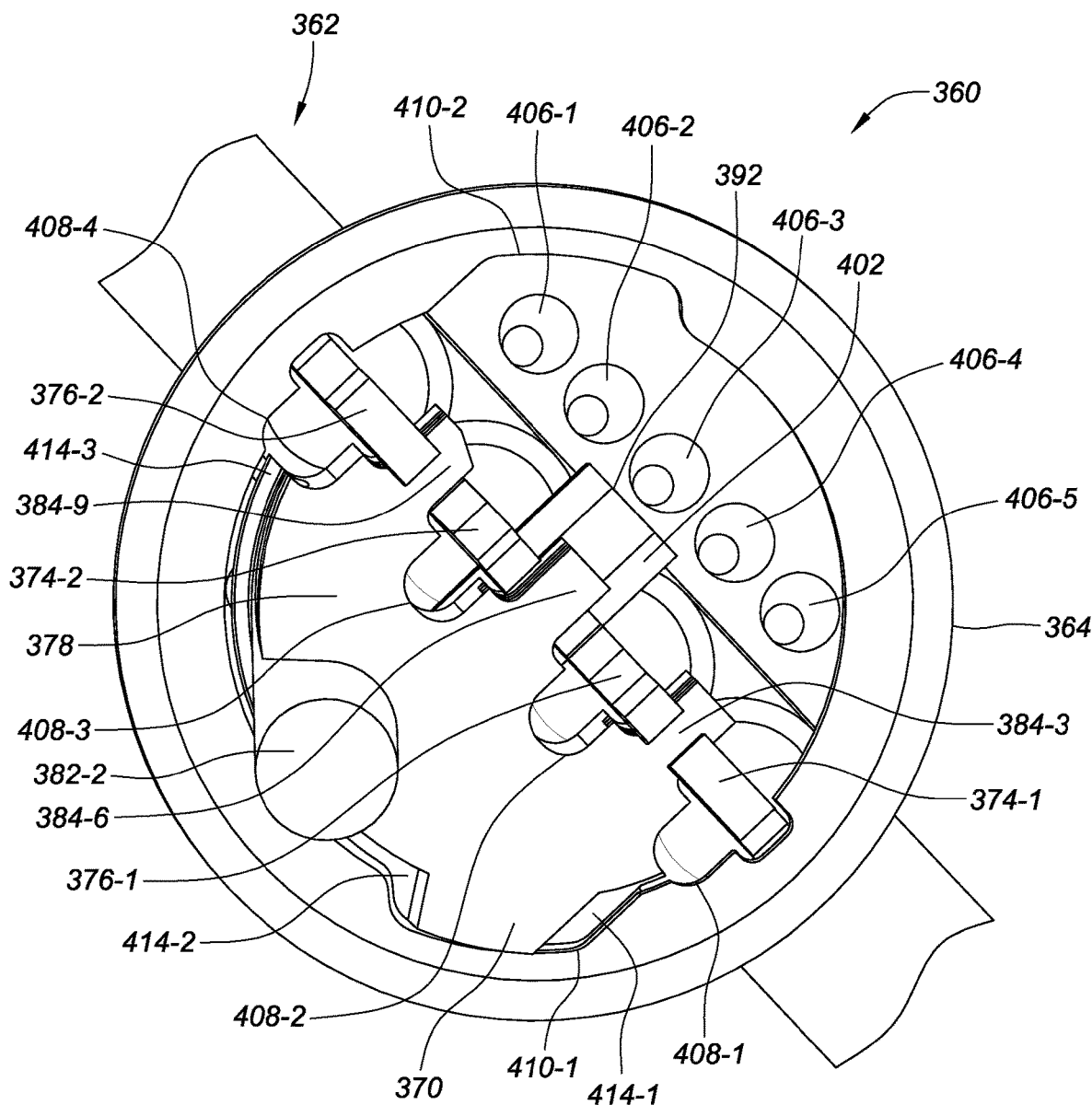
FIG. 8E is a rear view of the irrigated high density electrode catheter depicted in FIGS. 8A to 8D that includes a flexible tip portion, and bottom connective stem portion that includes an irrigation cross-over, according to various embodiments of the present disclosure.

FIG. 8E is a rear view of the irrigated high density electrode catheter 360 depicted in FIGS. 8A-8D that includes a flexible tip portion 362, and bottom connective stem portion 378 that includes an irrigation cross-over 392, according to various embodiments of the present disclosure. As previously discussed, the high density electrode catheter 360 can include an irrigation cross-over 392. The irrigation cross-over 392 can include a barrel portion 402, which can define a lumen that can be fluidly coupled with an irrigation tube, in some embodiments. The irrigation tube can provide a fluid to irrigation ports 406-1, 406-2, . . . , 406-5 disposed in a distal face of the irrigated coupler 364. As depicted, the irrigation ports 406-1, 406-2, . . . , 406-5 can be tapered. For example, the irrigation ports 406-1, 406-2, . . . , 406-5 can be tapered, such that a diameter of each of the irrigation ports 406-1, 406-2, . . . , 406-5 decreases distally to form a nozzle. In some embodiments, tapering the irrigation ports 406-1, 406-2, . . . , 406-5 can allow for an increased velocity of fluid flow through the irrigation ports 406-1, 406-2, . . . , 406-5.

As further depicted in FIG. 8E, the irrigated high density electrode catheter 360 includes a longitudinally extending ridge 384-3 disposed between the first outboard mounting arm 374-1 and the first inboard mounting arm 376-1, a second longitudinally extending ridge 384-6 disposed between the first inboard mounting arm 376-1 and the second inboard mounting arm 376-2, and a third longitudinally extending ridge 384-9 disposed between the second outboard mounting arm 374-2 and the second inboard mounting arm 376-2. In some embodiments, the bottom connective stem portion 378 can define a plurality of wire slots 408-1, 408-2, 408-3, 408-4 defined under each one of the inboard mounting arms 376-1, 376-2 and the outboard mounting arms 374-1, 374-2. In an example, a u-shaped slot is defined beneath each one of the inboard mounting arms 376-1, 376-2 and the outboard mounting arms 374-1, 374-2. Although the u-shaped slot can be of another shape. In some embodiments, one or more wires can be disposed in each slot and can electrically couple one or more electrodes and/or sensors disposed on each one of the inboard mounting arms 376-1, 376-2 and/or the outboard mounting arms 374-1, 374-2. The u-shaped slots can provide a space for the wires to be disposed in some embodiments.

In some embodiments, the irrigated coupler 364 can include key slots 410-1, 410-2, which can allow for the bottom connective stem portion 378 and the top connective stem portion 380 to be aligned with the irrigated coupler 364. As depicted in FIG. 8E, the bottom connective stem portion 378 can include a stem key 370, which can be disposed in a respective key slot 410-1. In some embodiments, the bottom connective stem portion 378 can include one or more recessed edges 414-1, 414-2, 414-3 that interface with the irrigated coupler 364. In an example, the one or more recessed edges 414-1, 414-2, 414-3 can provide an area for an adhesive to accumulate when connecting the bottom connective stem portion 378 to the irrigated coupler 364.

Figure 8F:
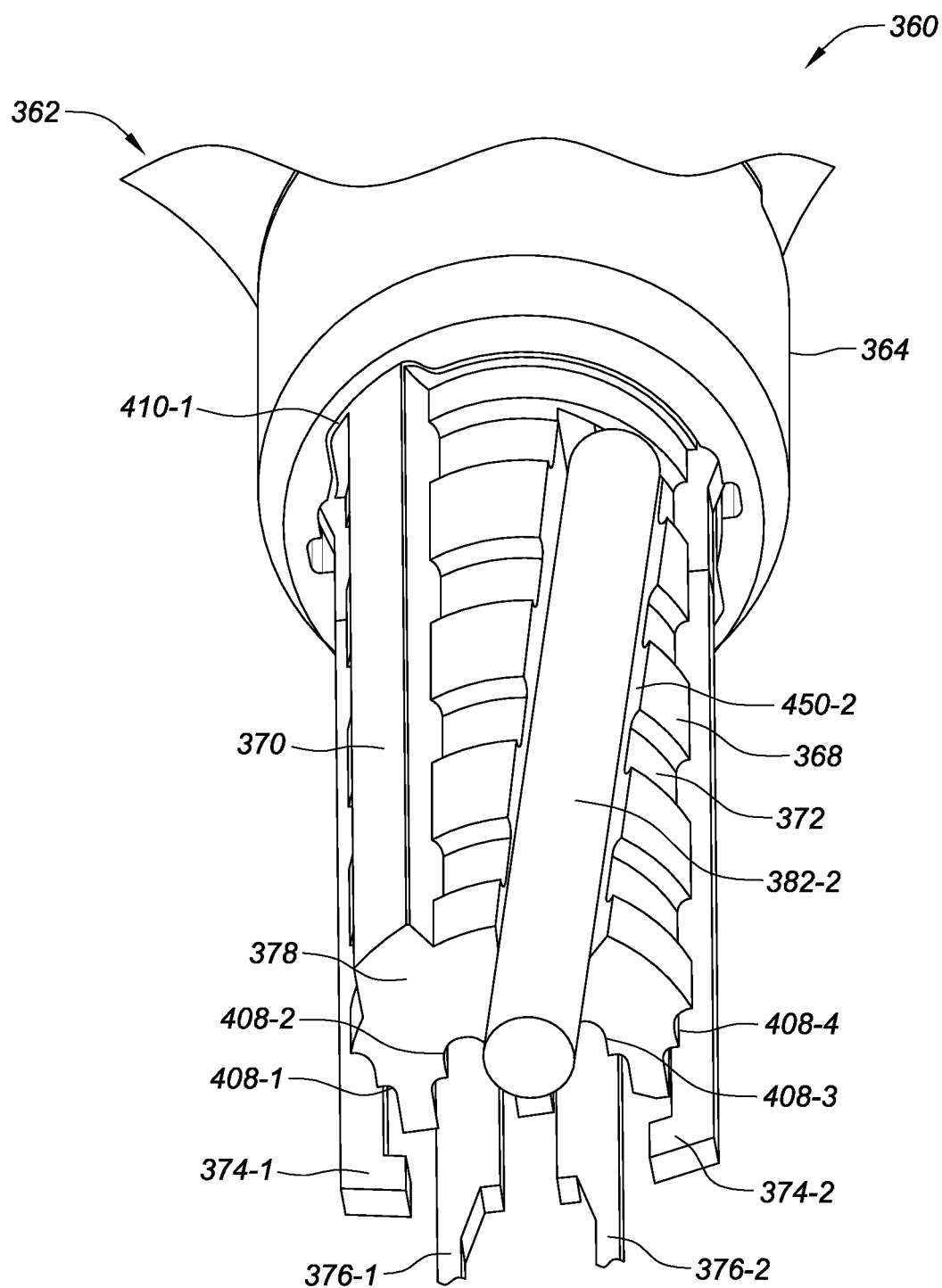
FIG. 8F is an isometric rear view of an irrigated high density electrode catheter depicted in FIGS. 8A to 8E that includes a flexible tip portion, with an irrigated coupler and ribbed bottom connective stem portion, according to various embodiments of the present disclosure.

FIG. 8F is an isometric rear view of an irrigated high density electrode catheter 360 depicted in FIGS. 8A-8E that includes a flexible tip portion 362, with an irrigated coupler 364 and ribbed bottom connective stem portion 378, according to various embodiments of the present disclosure. In some embodiments, ribs 368 can circumferentially extend around an outer surface of the bottom connective stem portion 378. In some embodiments, the ribs 368 can circumferentially extend around the outer surface of the bottom connective stem portion 378, up to the stem key 370, which is depicted as being disposed in the key slot 410-1. A radial height of the ribs can be less than, equal to, or greater than a radial height of the stem key 370. In some embodiments, the ribs 368 can define circumferential grooves 372 that extend around the outer surface of the bottom connective stem portion 378 between the ribs 368. The radial height of the ribs 368 can be configured to provide a diameter of the bottom connective stem portion 378, which is less than a diameter of a catheter shaft, which accepts the bottom connective stem portion 378. In some embodiments, the grooves can reduce a friction associated with inserting the bottom connective stem portion 378 into a lumen defined by the catheter shaft, and/or provide an area for an adhesive to collect when the bottom connective stem portion 378 is inserted into the lumen defined by the catheter shaft.

FIG. 8F further depicts the five DOF magnetic position sensor 382-2. In some embodiments, an outer surface of the five DOF magnetic position sensor 382-2 can be equal to (e.g., flush with) an outer surface of the ribs 368. In some embodiments, the outer surface of the five DOF magnetic position sensor 382-2 can be inset from (e.g., recessed with respect to) an outer surface of the ribs 368.

Figure 8G:
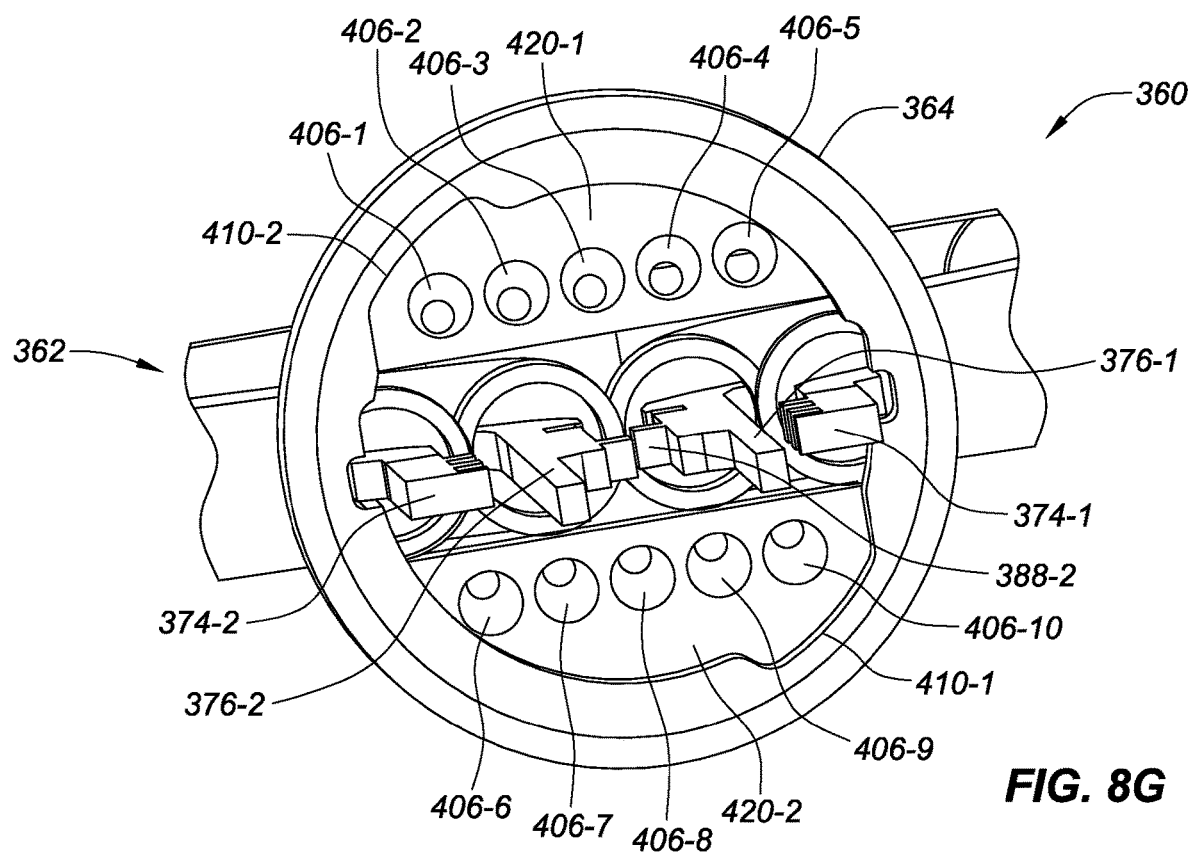
FIG. 8G is a rear view of an irrigated coupler and a flexible tip portion of an irrigated high density electrode catheter depicted in FIGS. 8A to 8F, according to various embodiments of the present disclosure.

FIG. 8G is a rear view of an irrigated coupler 364 and a flexible tip portion 362 of an irrigated high density electrode catheter 360 depicted in FIGS. 8A-8F, according to various embodiments of the present disclosure. The irrigated high density electrode catheter 360 can include outboard mounting arms 374-1, 374-2 and inboard mounting arms 376-1, 376-2. As previously discussed, the mounting arms can include one or more frame lock tabs. For example, with respect to the first inboard mounting arm 376-1, the first inboard mounting arm 376-1 can include a frame lock tab 388-2.

As depicted, the irrigated coupler includes a first row of irrigation ports 406-1, 406-2, . . . , 406-5 and a second row of irrigation ports 406-6, 406-7, . . . , 406-10, through which an irrigation fluid can be expelled. In an example, the irrigated high density electrode catheter 360 can include a first manifold area 420-1 and a second manifold area 420-2, which can distribute fluid to each one of the irrigation ports 406-1, 406-2, . . . , 406-10. As depicted, the first manifold area 420-1 and the second manifold area 420-2 can be recessed areas through which fluid can flow.

Figure 8H:
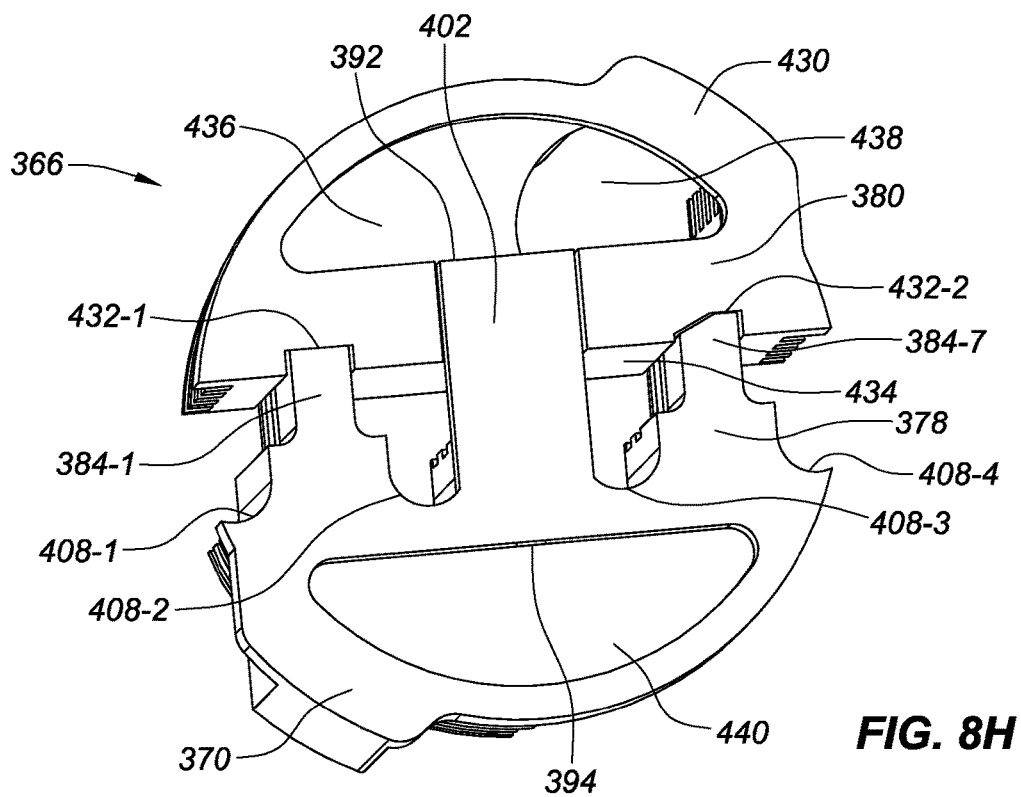
FIG. 8H is a front view of a connective stem depicted in FIGS. 8A to 8G, according to various embodiments of the present disclosure.

FIG. 8H is a front view of a connective stem 366, according to various embodiments of the present disclosure. The connective stem can include a bottom connective stem portion 378 and a top connective stem portion 380. As previously discussed, the bottom connective stem portion 378 can include a plurality of longitudinal ridges (e.g., longitudinal ridges 384-1, 384-7) and the bottom connective stem portion 378 can define a plurality of wire slots. As discussed herein, one or more frame members can be disposed between or adjacent to each one of the longitudinal ridges (e.g., longitudinal ridges 384-1, 384-7) and wires can be disposed in each one of the wire slots to provide a way to electrically couple one or more electrodes and/or sensors disposed on a flexible framework formed from the frame members. As further depicted, the bottom connective stem portion 378 can include a bottom stem key 370 and the top connective stem portion 380 can include a top stem key 430, which can aid in connection with the irrigated coupler 364.

In some embodiments, the top connective stem portion 380 can define one or more longitudinal slots 432-1, 432-2 in a planar surface 434 of the top connective stem portion 380. As depicted, the longitudinal ridges 384-1, 384-7 can be disposed in a respective one of the longitudinal slots 432-1, 432-2.

The top connective stem portion 380 can define a top inlet manifold 436 on a distal face of the top connective stem portion 380 and can further define an irrigation tube lumen 438 into which an irrigation tube can be disposed in some embodiments. The irrigation tube can provide a flow of irrigation fluid to the top inlet manifold 436, which can distribute the irrigation fluid to a first row of irrigation ports 406-1, 406-2, . . . , 406-5. The connective stem 366 can include an irrigation cross-over 392, which can transfer fluid from the top inlet manifold 436 to a bottom inlet manifold 440 via a cross-over lumen 394, which is defined by a barrel portion 402. The bottom inlet manifold 440 can distribute the irrigation fluid to a second row of irrigation ports 406-6, 406-7, . . . , 406-10.

Figure 8I:
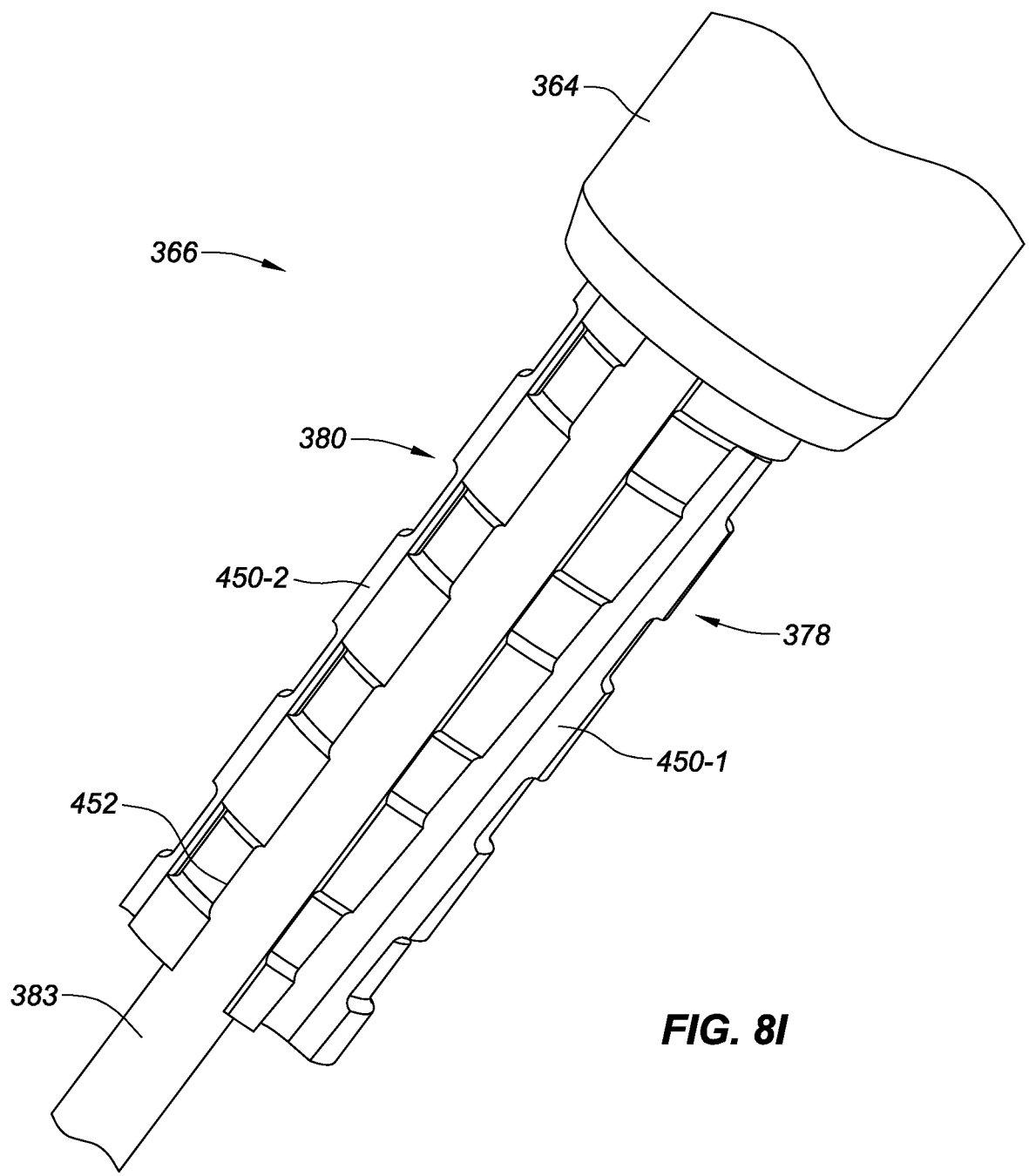
FIG. 8I is an isometric side view of a connective stem and an irrigated coupler depicted in FIGS. 8A to 8H, according to various embodiments of the present disclosure.

FIG. 8I is an isometric side view of a connective stem 366 and an irrigated coupler 364, according to various embodiments of the present disclosure. In some embodiments, as discussed herein, the connective stem 366 can include a pair of sensor grooves defined in the connective stem 366. In an example, a first sensor groove 450-1 can be defined in a bottom connective stem portion 378 and a second sensor groove 450-2 can be defined in a top connective stem portion 380, as further discussed herein. The first and second sensor grooves 450-1, 450-2 can be disposed at angles that are divergent with respect to a longitudinal axis that extends through the connective stem 366. Additionally, the first sensor groove 450-1 can be disposed at an angle that is divergent with respect to the second sensor groove 450-2.

FIG. 8I further depicts an irrigation tube 383 that longitudinally extends along the connective stem 366. The connective stem 366 can define an irrigation tube channel 452 that longitudinally extends along the connective stem 366. In some embodiments, the irrigation tube channel 452 can longitudinally extend along the top connective stem portion 380, in some embodiments. The irrigation tube 383 can be formed from a flexible material in some embodiments, such as a polymer.

FIG. 8J is a schematic top view of the irrigated high density electrode catheter 360 that illustrates fluid flow 396-1, 396-2, 396-3 through the irrigated high density electrode catheter 360, according to embodiments of the present disclosure. In an example, an irrigation tube 383 can be disposed in a connective stem 366 of the irrigated high density electrode catheter 360, as previously discussed herein. The connective stem 366 can include a first five DOF magnetic position sensor 382-1 and can be connected with an irrigated coupler 364. A flexible tip portion 362 can extend distally with respect to the irrigated coupler 364. In some embodiments, an initial irrigation fluid flow 396-1 can be provided through the irrigation tube 383. A cross-over irrigation flow 396-2 can be directed through a cross-over lumen 394 defined by an irrigation cross-over 392 and into a bottom inlet manifold (e.g., bottom inlet manifold 440, FIG. 8H) and through a second row of irrigation ports (e.g., irrigation ports 406-6, 406-7, . . . , 406-10, FIG. 8G). A remainder flow 396-3 of the initial irrigation fluid flow 396-1 that has not been directed through the cross-over lumen 394 can be directed into a top inlet manifold 436 and through a first row of irrigation ports 406-1, 406-2, . . . , 406-5.

FIG. 9A is an isometric side and rear view of a flexible tip mount 460, according to various embodiments of the present disclosure. Although some embodiments of the present disclosure reference use with a diagnostic catheter, embodiments of the present disclosure can also be used with an ablation catheter including a flexible or rigid tip. For example, the mount 460 can be used with an ablation catheter with a flexible or rigid tip. The flexible tip mount 460 can include an irrigated coupler 462. The irrigated coupler 462 can have those features as previously discussed herein, for example, in relation to FIGS. 8A to 8I. The flexible tip mount 460 can include a connective stem 458, which can include a top connective stem portion 464 and a bottom connective stem portion 466. The top connective stem portion 464 can define an irrigation channel 468. The top connective stem portion 464 can further define an irrigation lumen 470. In an example, an irrigation tube can be disposed in the irrigation channel 468 and can be fluidly coupled with the irrigation channel 468. An irrigation fluid can be provided to the irrigation channel 468 via the irrigation tube and can flow through irrigation ports defined in the irrigated coupler 462.

The top connective stem portion 464 can further be coupled with the irrigated coupler 462 and can include a top stem key 472, which can be disposed in a respective key slot 473 defined in the irrigated coupler 462. As further depicted, the irrigated coupler 462 can define recessed edges 474-1, 474-2, which can extend along an interface between the irrigated coupler 462 and the connective stem 458. The recessed edges 474-1, 474-2 can provide an area for an adhesive to accumulate. In an example, an adhesive can be used to connect the connective stem 458 and the irrigated coupler 462.

In some embodiments, the bottom connective stem portion 466 can include a plurality of longitudinal ridges 476-1, 476-2, 476-3 that extend perpendicular to an inner planar surface of the bottom connective stem portion 466. The top connective stem portion 464 can define a plurality of longitudinal slots (e.g., channels) 478-1, 478-2, 478-3 in an inner planar surface of the top connective stem portion 464. As previously discussed herein, the plurality of longitudinal ridges 476-1, 476-2, 476-3 can be disposed in a respective one of the plurality of longitudinal slots 478-1, 478-2, 478-3. In some embodiments, a framework for a flexible tip portion can be disposed between and/or adjacent to each one of the longitudinal slots 478-1, 478-2, 478-3.

The framework of the flexible tip portion can be disposed between and/or adjacent to the plurality of longitudinal ridges 476-1, 476-2, 476-3. In some embodiments, the bottom connective stem portion 466 can define a plurality of wire slots 490-1, 490-2, 490-3, 490-4, as previously discussed herein. In an example, a u-shaped slot can be defined between and/or adjacent to each one of the longitudinal ridges 476-1, 476-2, 476-3, although the u-shaped slot can be of another shape. In some embodiments, one or more wires can be disposed in each slot and can be electrically coupled with one or more electrodes and/or sensors disposed on the framework of the flexible tip portion. The u-shaped slots can provide a space for the wires to be disposed in some embodiments.

In some embodiments, the irrigated coupler 462 can include a plurality of irrigation ports. As depicted in FIG. 9C, the irrigated coupler 462 can include a first row of irrigation ports and a second row of irrigation ports on either side of a flexible framework slot 492. For ease or illustration, only a first irrigation port 494-1 from a first row of irrigation ports and a second irrigation port 494-2 from a second row of irrigation ports has been labeled.

In some embodiments, the connective stem 458 can define a first sensor groove 480-1 and a second sensor groove 480-2. As depicted, the first and second sensor grooves 480-1, 480-2 can be disposed at angles that are divergent with respect to a longitudinal axis that extends through the connective stem 458. Additionally, the first sensor groove 480-1 can be disposed at an angle that is divergent with respect to the second sensor groove 480-2.

FIG. 9B is a longitudinal axis 482 along which the connective stem 458 extends, according to embodiments of the present disclosure. In some embodiments, a first sensor can be disposed in the first sensor groove 480-1 and can extend along a first sensor longitudinal axis 484-1 and a second sensor can be disposed in the second sensor groove 480-2 and can extend along a second sensor longitudinal axis 484-2. In some embodiments, the first sensor longitudinal axis 484-1 and the second sensor longitudinal axis 484-2 can be disposed at an angle 486-1, 486-2 with respect to one another. In an example, the angles 486-1, 486-2 can be equal to one another. In some embodiments, the angles 486-1, 486-2 can be in a range from 1 degree to 20 degrees. In some embodiments, the angles 486-1, 486-2 can be in a range from 6 degrees to 12 degrees. In an example, each sensor longitudinal axis 484-1, 484-2 can be disposed at an angle with respect to the longitudinal axis 482. For example, the angle at which each sensor longitudinal axis 484-1, 484-2 can be disposed at with respect to the longitudinal axis 482 can be in a range from 0.5 degrees to 10 degrees. In some embodiments, the angle at which each sensor longitudinal axis 484-1, 484-2 can be disposed at with respect to the longitudinal axis 482 can be in a range from 3 degrees to 6 degrees. In some embodiments, the angle at which each sensor longitudinal axis 484-1, 484-2 is disposed at with respect to the longitudinal axis 482 can be equal to one another.

FIG. 9C is an isometric side and front view of a flexible tip mount 460 depicted in FIG. 9A, according to various embodiments of the present disclosure. The flexible tip mount 460 can include an irrigated coupler 462. The irrigated coupler 462 can have those features as previously discussed herein, for example, in relation to FIGS. 8A to 8I. For instance, the irrigated coupler 462 can have a number of irrigation ports. As depicted, the flexible tip mount 460 can include a connective stem 458, which can include a top connective stem portion 464 and a bottom connective stem portion 466. The top connective stem portion 464 can define an irrigation channel 468. The top connective stem portion 464 can further define an irrigation lumen 470. In an example, an irrigation tube can be disposed in the irrigation channel 468 and can be fluidly coupled with the irrigation lumen 470. An irrigation fluid can be provided to the irrigation lumen 470 via the irrigation tube and can flow through irrigation ports defined in the irrigated coupler 462.

The top connective stem portion 464 can further be coupled with the irrigated coupler 462 and can include a top stem key 472, which can be disposed in a respective key slot 473 defined in the irrigated coupler 462. As further depicted, the irrigated coupler 462 can define recessed edges 474-1, 474-2, which can extend along an interface between the irrigated coupler 462 and the connective stem 458. The recessed edges 474-1, 474-2 can provide an area for an adhesive to accumulate. In an example, an adhesive can be used to connect the connective stem 458 and the irrigated coupler 462.

In some embodiments, the bottom connective stem portion 466 can include a plurality of longitudinal ridges 476-1, 476-2, 476-3. The top connective stem portion 464 can define a plurality of longitudinal slots 478-1, 478-2, 478-3 in a planar surface of the top connective stem portion 464. As previously discussed herein, the plurality of longitudinal ridges 476-1, 476-2, 476-3 can be disposed in a respective one of the plurality of longitudinal slots 478-1, 478-2, 478-3. In some embodiments, a framework for a flexible tip portion can be disposed between and/or adjacent to each one of the longitudinal slots 478-1, 478-2, 478-3.

In some embodiments, the connective stem 458 can define a first sensor groove 480-1 and a second sensor groove 480-2. As depicted, the first and second sensor grooves 480-1, 480-2 can be disposed at angles that are divergent with respect to a longitudinal axis that extends through the connective stem 458. Additionally, the first sensor groove 480-1 can be disposed at an angle that is divergent with respect to the second sensor groove 480-2.

Figure 9D:
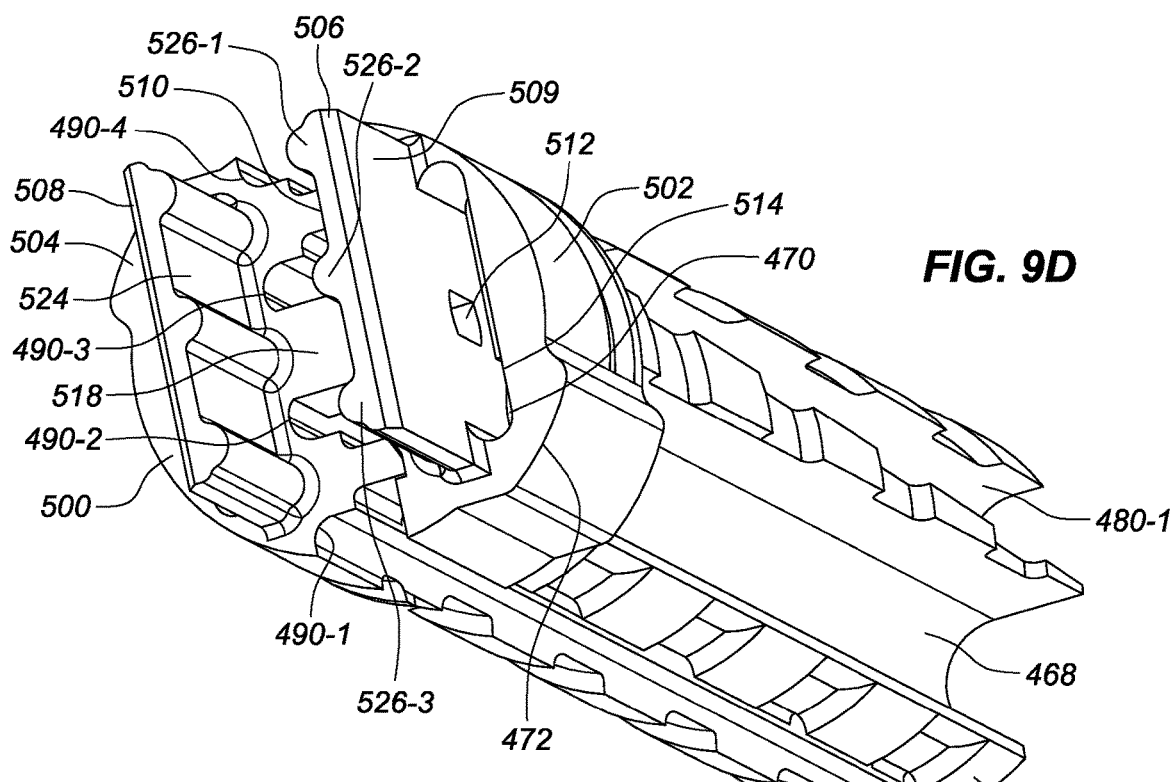
FIGS. 9D and 9E are isometric side and front views of the bottom connective stem portion and top connective stem portion previously depicted in FIGS. 9A and 9C, according to various embodiments of the present disclosure.
Figure 9E:
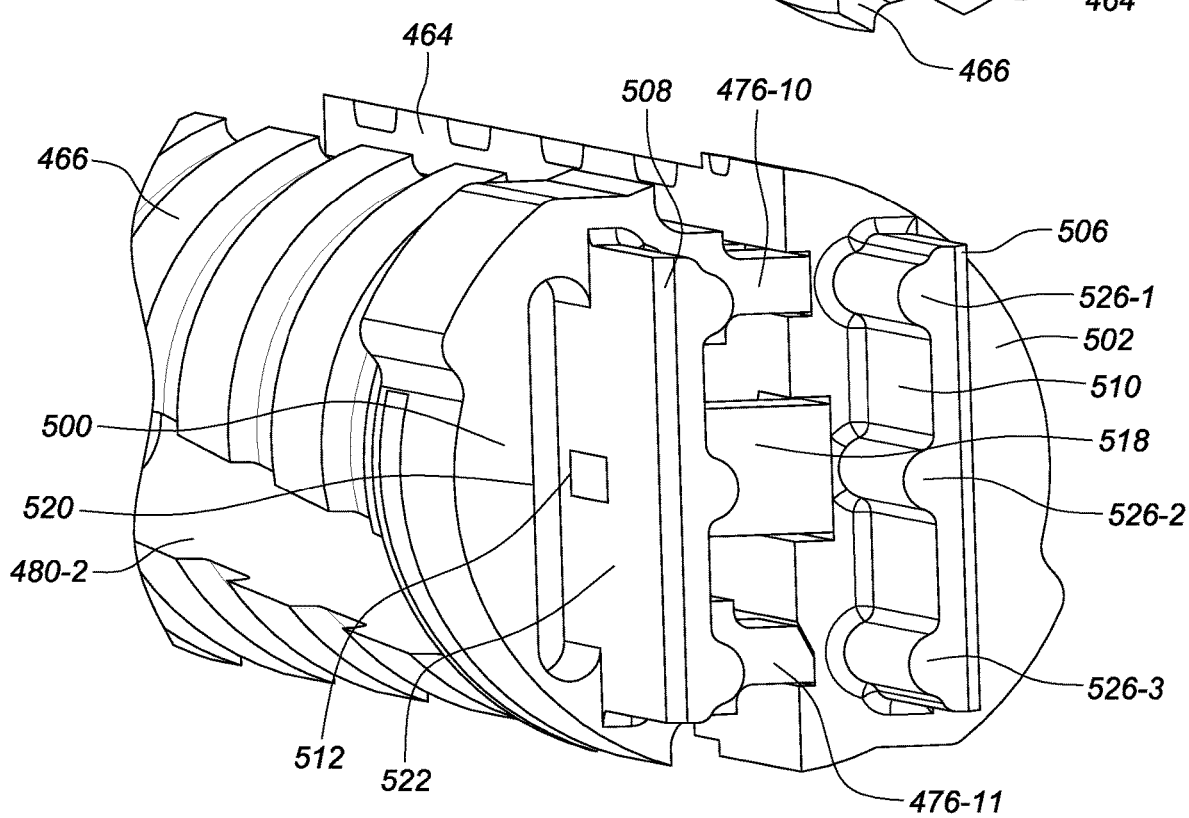

FIGS. 9D and 9E are isometric side and front views of the bottom connective stem portion 466 and top connective stem portion 464 previously depicted in FIGS. 9A and 9C, according to various embodiments of the present disclosure. In some embodiments, the bottom connective stem portion 466 can include a bottom flared distal mounting portion 500. The bottom flared distal mounting portion 500 can have an increased diameter over portions of the bottom connective stem portion 466 located proximal to the bottom flared distal mounting portion 500. Likewise, in some embodiments, the top connective stem portion 464 can include a top flared distal mounting portion 502. The top flared distal mounting portion 502 can have an increased diameter over portions of the top connective stem portion 464 located proximal to the top flared distal mounting portion 502. Each of the top flared mounting portion 502 and the bottom flared distal mounting portion 500 can include a top connective stem key 472 and a bottom connective stem key 504, respectively, as previously discussed herein.

In some embodiments, the top connective stem portion 464 can include a top alignment framework feature 506 and the bottom connective stem portion 466 can include a bottom framework alignment feature 508. The top framework alignment feature 506 can extend distally with respect to the distal end of the top connective stem portion 464 and can include a top planar irrigation face 509 and a planar inner face 510, better illustrated in FIG. 9E. The bottom framework alignment feature 508 can extend distally with respect to the distal end of the bottom connective stem portion 466 and can include a bottom planar irrigation face 522 and a planar inner face 524.

In some embodiments, an irrigation cross-over lumen 512 can be defined in the top planar irrigation face 509. In an example, an irrigation fluid can be provided via an irrigation channel 468, which can hold an irrigation tube in some embodiments, as discussed herein. The irrigation fluid can pass from the irrigation tube disposed in the irrigation channel 468 and through the irrigation lumen 470 into a top irrigation manifold 514. In some embodiments, the top irrigation manifold 514 can be a space defined between the top flared mounting portion 502 and the top planar irrigation face 509. The top irrigation manifold 514 can be in fluid communication with the first row of irrigation ports (e.g., first irrigation port 494-1), as depicted in FIG. 9C, and can thus provide the irrigation fluid to the first row of irrigation ports.

In some embodiments, the irrigation fluid that flows into the top irrigation manifold 514 can also flow through the irrigation cross-over lumen 512, which can be defined in the planar irrigation face 509 and can extend therethrough. The irrigation fluid can flow through a barrel portion 518 and out an opposite side of the irrigation cross-over lumen 512 and into a bottom irrigation manifold 520. The bottom irrigation manifold 520 can be a space defined between the bottom flared mounting portion 500 and a bottom planar irrigation face 522. The bottom irrigation manifold 520 can be in fluid communication with the second row of irrigation ports (e.g., second irrigation port 494-2), as depicted in FIG. 9C, and can thus provide the irrigation fluid to the first row of irrigation ports. Accordingly, irrigation fluid can be expelled via the first and second rows of irrigation ports via the irrigation cross-over lumen 512.

In some embodiments, the planar inner faces 510, 524 can each include longitudinally extending alignment features that extend along each one of the planar faces 510, 524. For example, with reference to the planar inner face 510, the planar inner face 510 can include three alignment features 526-1, 526-2, 526-3 that longitudinally extend along the planar inner face 510. Each one of the alignment features 526-1, 526-2, 526-3 can be hemi cylindrical in shape. In some embodiments, the alignment features 526-1, 526-2, 526-3 can be disposed in line with longitudinal ridges 476-10, 476-11 and can thus help to separate a flexible framework that is disposed between the top connective stem portion 464 and the bottom connective stem portion 466.

In some embodiments, the alignment features 526-1, 526-2, 526-3 can serve as strengthening members. For example, each one of the bottom and top framework alignment features 508, 506 can include longitudinally and axially extending alignment features that extend along the planar inner faces 510, 524. The alignment features 526-1, 526-2, 526-3 can increase a stiffness and/or strength of each one of the bottom and top framework alignment features 508, 506 by adding extra material to the planar inner faces 510, 524. In some embodiments, the top connective stem portion 464 and the bottom connective stem portion 466 can be formed from a polymer. The polymer can be injection molded, machined, etc. to form the top connective stem portion 464 and the bottom connective stem portion 466.

Figure 9F:
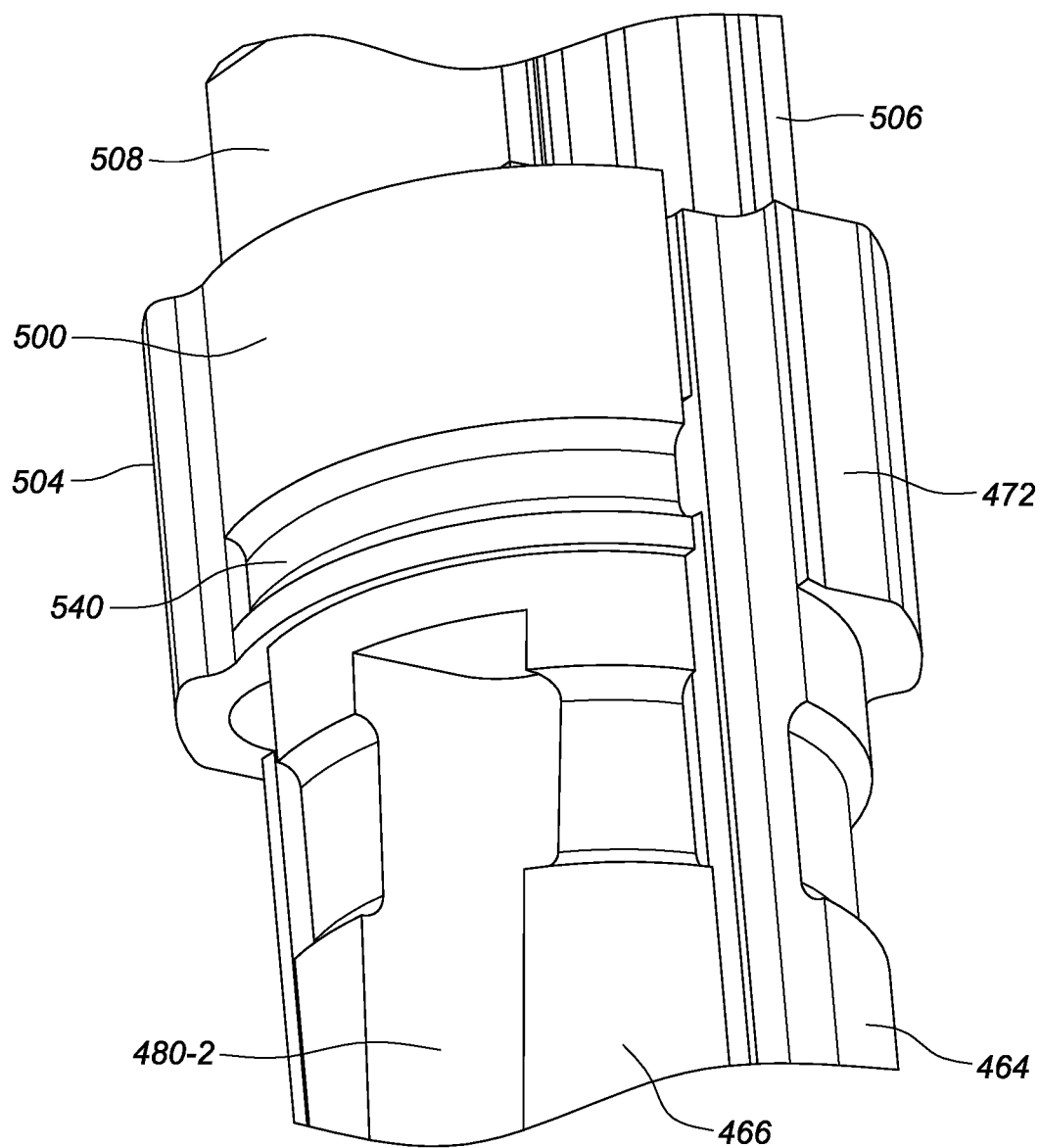
FIG. 9F is an isometric view of a distal end of the top connective stem portion and the bottom connective stem portion previously depicted in FIGS. 9A and 9C to 9E, according to various embodiments of the present disclosure.

FIG. 9F is an isometric view of a distal end of the top connective stem portion 464 and the bottom connective stem portion 466 previously depicted in FIGS. 9A and 9C to 9E, according to various embodiments of the present disclosure. As depicted, the bottom connective stem portion 466 defines the second sensor groove 480-2 in which a sensor can be placed. In some embodiments, the bottom connective stem portion 466 can include a bottom flared distal mounting portion 500, from which extends a bottom connective stem key 504, as previously discussed. Likewise, the top connective stem portion 464 can include a top flared distal mounting portion 502, from which extends a top connective stem key 472. The top connective stem portion 464 can include a top alignment framework feature 506 and the bottom connective stem portion 466 can include a bottom framework alignment feature 508.

In some embodiments, a groove 540 can be defined in a proximal portion of the bottom flared distal mounting portion 500 and/or can be formed in a proximal portion of the top flared distal mounting portion 502. With reference to the bottom flared distal mounting portion 500, the groove can circumferentially extend about the bottom flared distal mounting portion 500.

FIG. 9G is a proximal end view of the bottom connective stem portion 466 and the top connective stem portion 464 as previously depicted in FIGS. 9A and 9C to 9F, according to various embodiments of the present disclosure. As further depicted, the irrigation lumen 470 can be fluidly coupled with the top irrigation manifold 514 and can thus provide an irrigation fluid to the top irrigation manifold 514. A portion of the irrigation fluid can be transferred to a bottom irrigation manifold 520 via a cross-over lumen defined by a barrel portion, as previously discussed. In some embodiments, a tapered wall 550 can define the irrigation lumen 470. In an example, the tapered wall 550 can be tapered from a proximal opening of the irrigation lumen 470 to a tapered point 552. In an example, the tapered wall 550 can improve a flow of fluid through the irrigation lumen 470. For instance, the flow of fluid through the irrigation lumen 470 can be improved by reducing a turbulence in the flow of fluid. In an example where the irrigation lumen 470 does not include a tapered wall 550, the flow of fluid can be more turbulent, increasing a pressure and causing disturbances in flow from the irrigation ports 494 defined in the irrigated coupler 462.

Figure 9I:
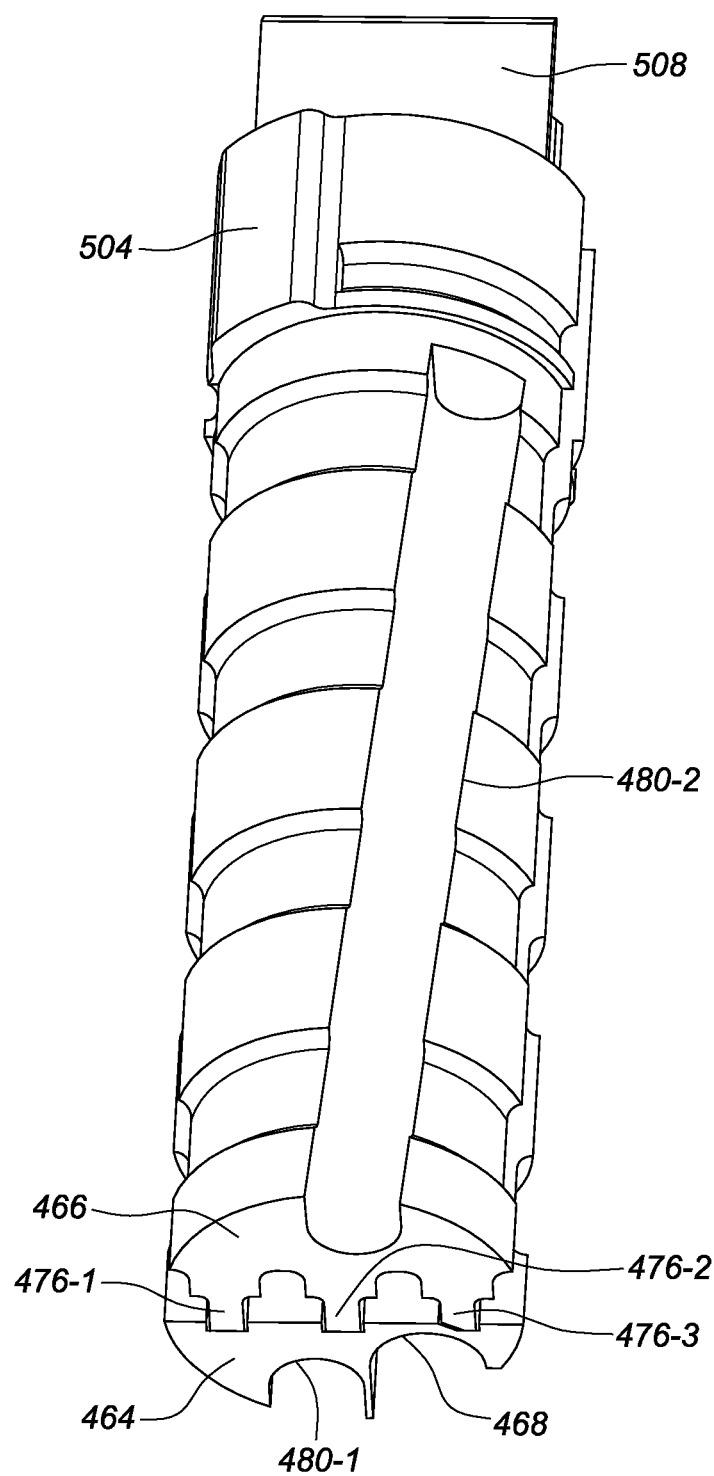

FIG. 9H is an isometric top and proximal end view of the top connective stem portion 464 and the bottom connective stem portion 466 and FIG. 9I is a bottom and rear isometric view of the bottom connective stem portion 466 and the top connective stem portion 464, according to various embodiments of the present disclosure. As depicted, the first sensor groove 480-1 is disposed at an angle with respect to a longitudinal axis along which the top connective stem portion 464 and the bottom connective stem portion 466 extend. As discussed in relation to FIG. 9B, the second sensor groove 480-2 can be disposed at an angle with respect to the first sensor groove 480-1. FIGS. 9G and 9H further depict circumferential grooves 481-1, 481-2, 481-3, 481-4 that extend around a circumference of the connective stem portions 464, 466.

Figure 9J:
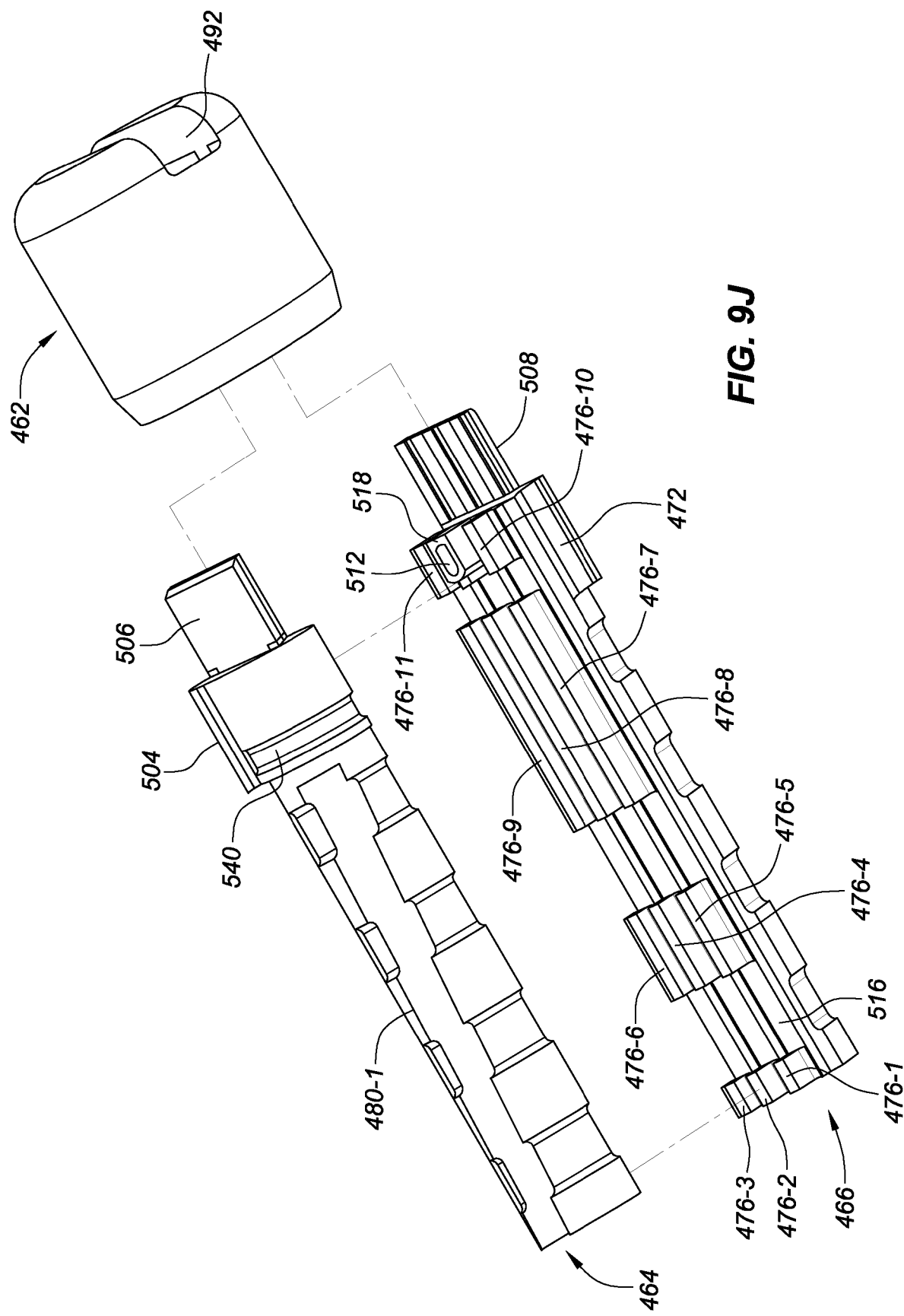
FIG. 9J is an isometric side view of the top connective stem portion, the bottom connective stem portion, and the irrigated coupler.

FIG. 9J is an isometric side view of the top connective stem portion 464, the bottom connective stem portion 466, and the irrigated coupler 462, and FIGS. 9K to 9N are isometric side and rear views of the top connective stem portion 464, the bottom connective stem portion 466, and the irrigated coupler 462, according to embodiments of the present disclosure. As depicted, the bottom connective stem portion 466 can include a plurality of longitudinal ridges 476-1, 476-2, 476-3, 476-4, 476-5, 476-6, 476-7, 476-8, 476-9, 476-10, 476-11, hereinafter referred to in the plural as longitudinal ridges 476, that extend perpendicular to an inner planar surface 516 of the bottom connective stem portion 466. In some embodiments, a flexible framework of an understructure can be disposed between the longitudinal ridges 476. The bottom connective stem portion 466 further includes a barrel portion 518 that extends perpendicular to the inner planar surface 516 of the bottom connective stem portion 466. The barrel portion can define the irrigation cross-over lumen as discussed herein.

As further depicted in FIG. 9J, the top connective stem portion 464 defines the first sensor groove 480-1 in which a position sensor (e.g., magnetic sensor can be disposed). The bottom connective stem portion 466 can define a second sensor groove 480-2 and irrigation channel 468. The top connective stem portion 464 and the bottom connective stem portion 466 can be assembled such that the longitudinal ridges 476 disposed on the inner planar surface 516 of the bottom connective stem portion 466 align with and are disposed within longitudinal slots 478-1, 478-2, 478-3 defined in an inner planar surface of the top connective stem portion 464. Upon assembly of the top connective stem portion 464 and the bottom connective stem portion 466, the top connective stem portion 464 and the bottom connective stem portion 466 can be disposed in the irrigated coupler 462.

Figure 9K:
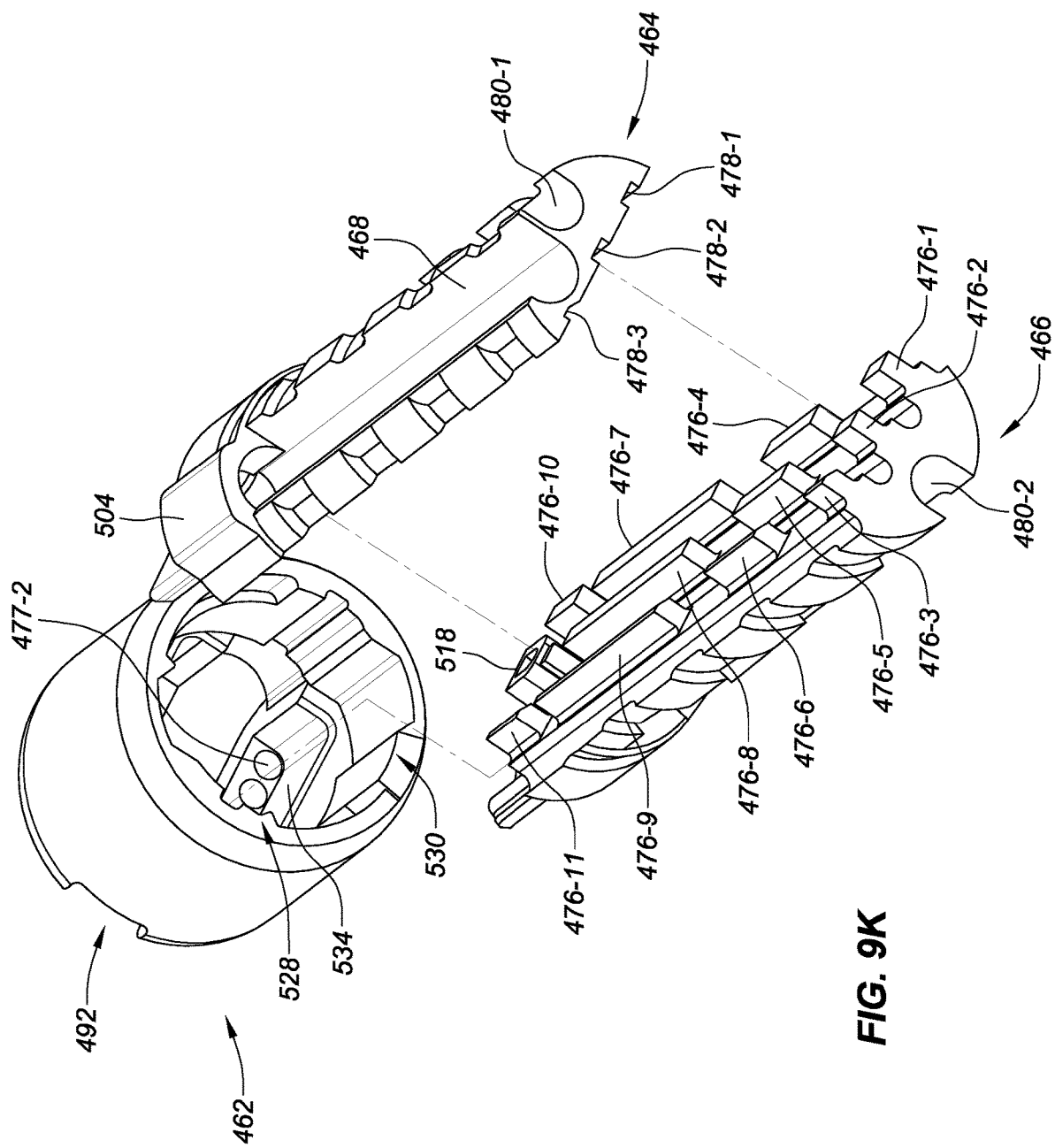
FIGS. 9K to 9N depict isometric side and rear views of the top connective stem portion, the bottom connective stem portion, and the irrigated coupler previously depicted in FIGS. 9A and 9C to 9I, according to embodiments of the present disclosure.
Figure 9L:
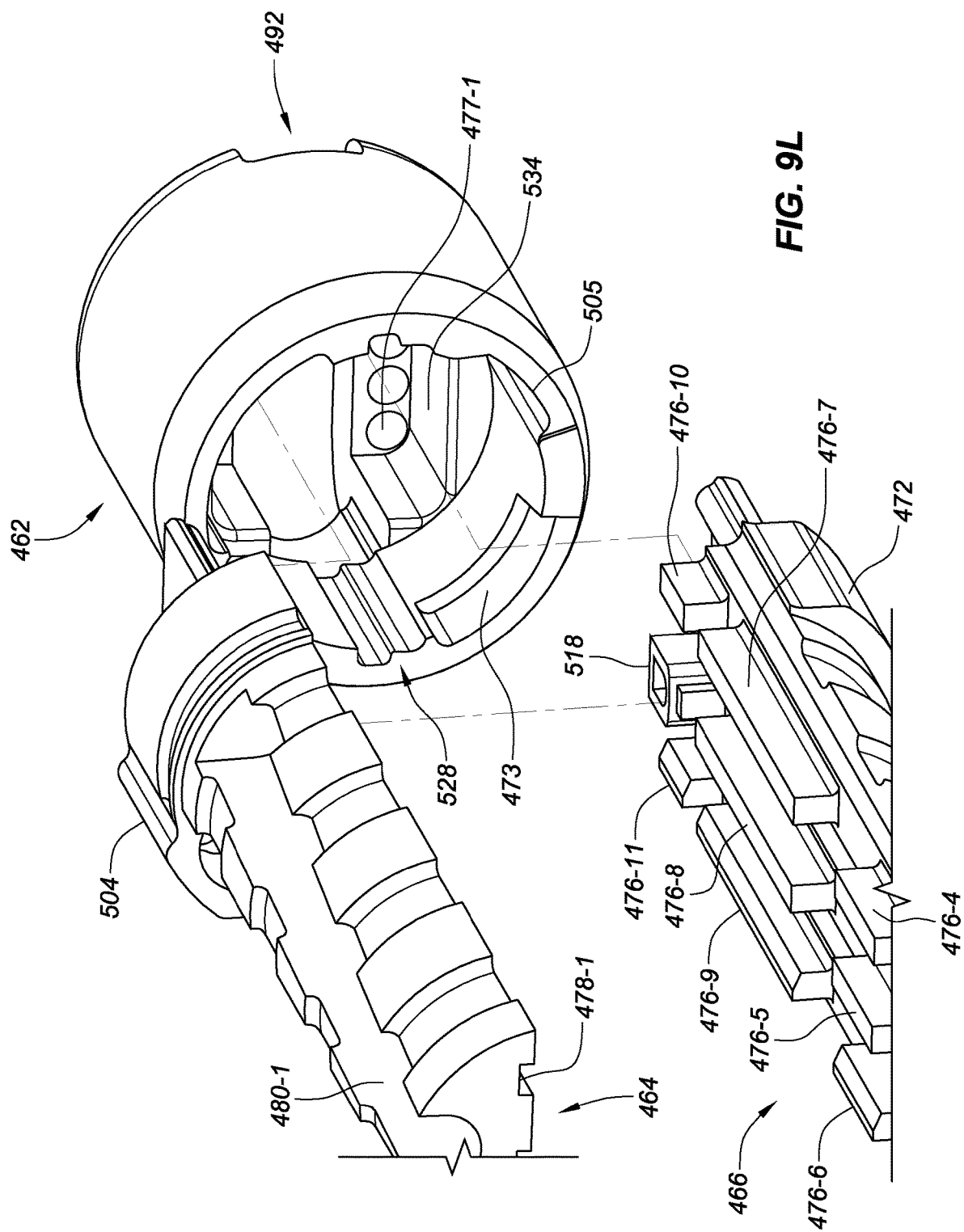
Figure 9M:
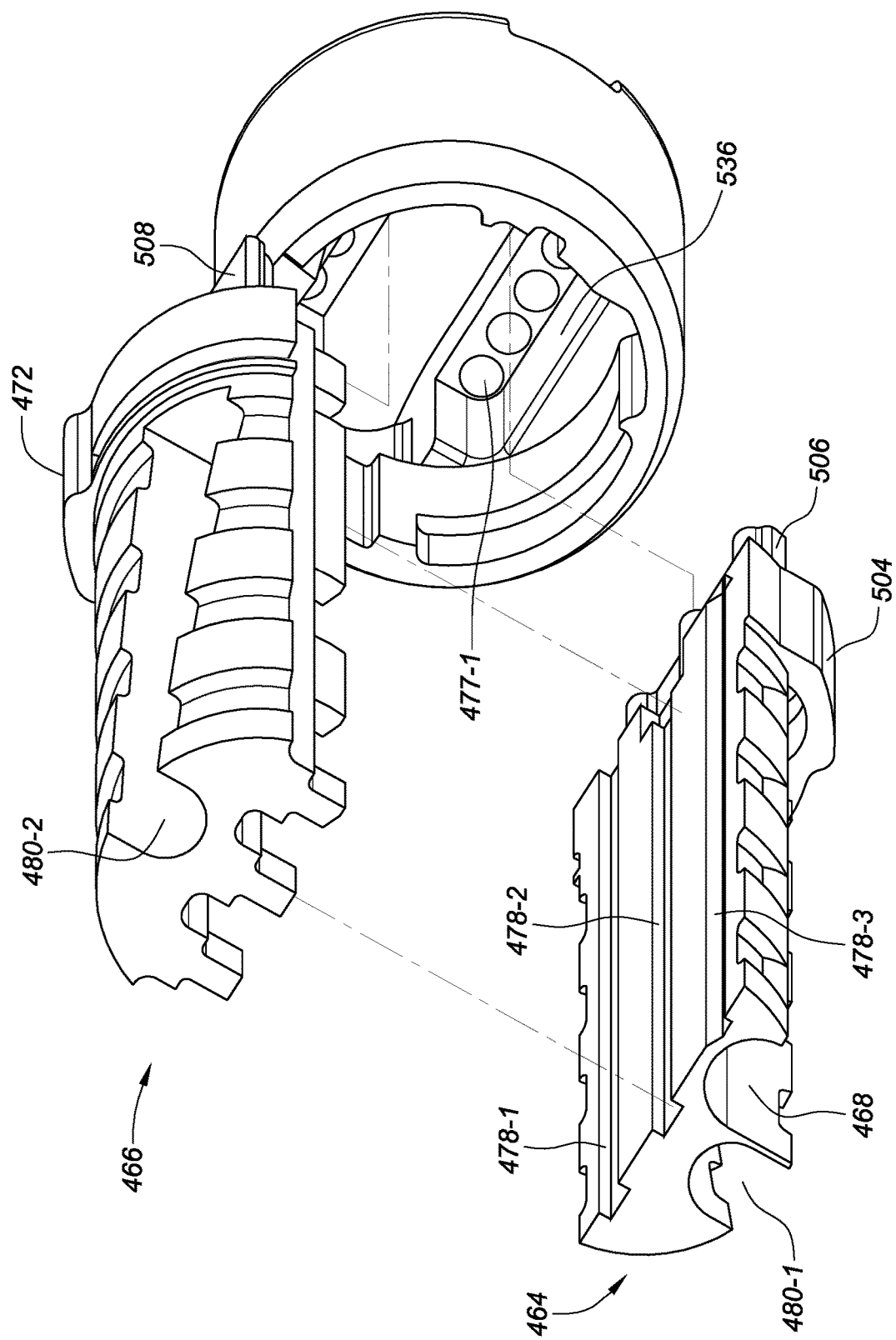
Figure 9N:
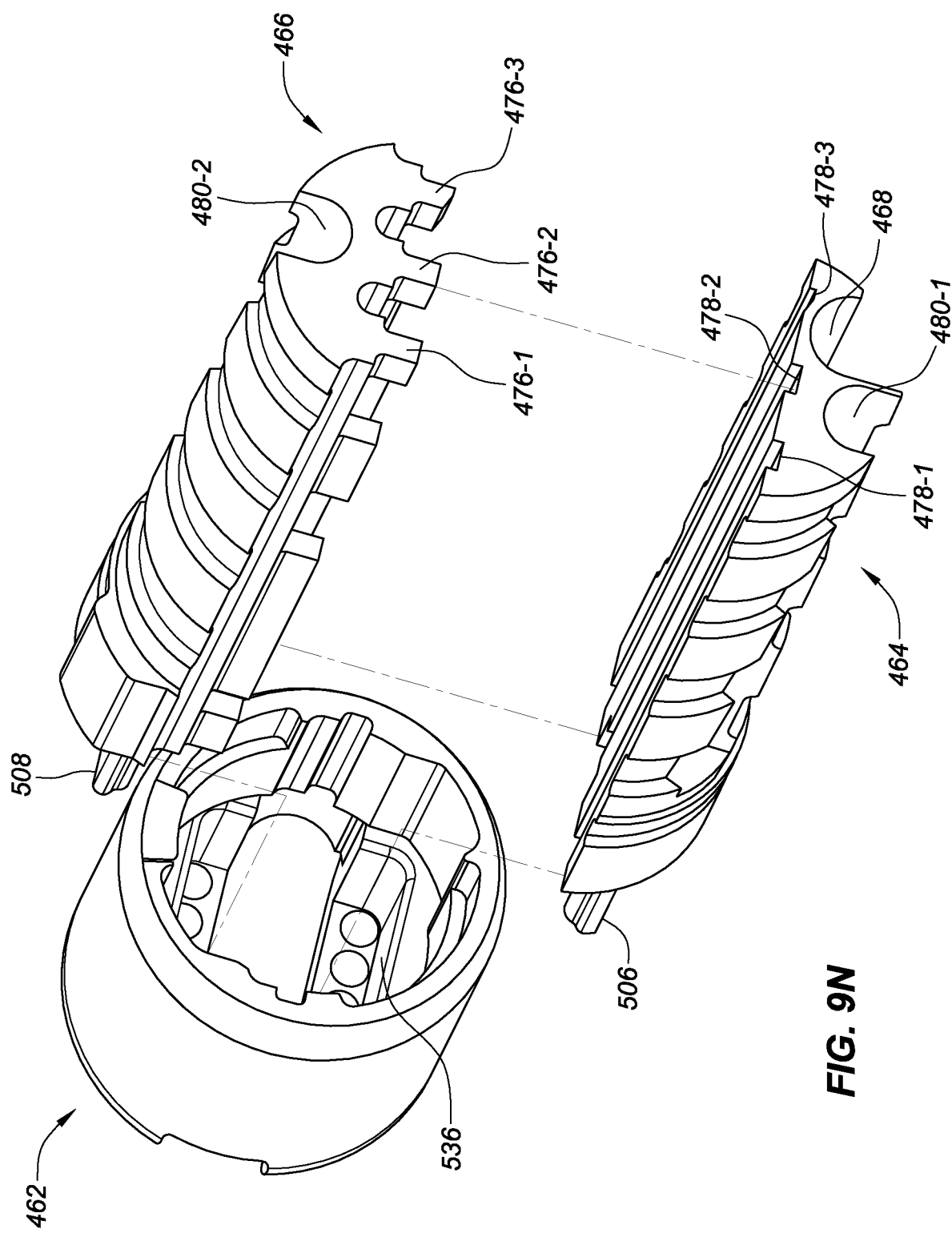

In some embodiments, the irrigated coupler 462 can include irrigation ports (e.g., irrigation port 477-1, 477-2) through which an irrigation fluid can flow, as discussed herein. The irrigated coupler 462 can further define a flexible framework slot 492, in which a flexible tip portion of a catheter can be disposed. As depicted in FIG. 9K, the irrigated coupler 462 can define longitudinal side slots 528 into which the top connective stem portion 464 and the bottom connective stem portion 466 can be slid into. In an example, the longitudinal side slots 528 can be defined in an inner wall of the irrigated coupler 462. The distal ends of the top connective stem portion 464 and the bottom connective stem portion 466 can be slid into the longitudinal side slots 528 and into a mounting lumen 530 defined by the irrigated coupler. In some embodiments, each of the bottom connective stem portion 466 and top connective stem portion 464 can include stem keys 472, 504, as previously discussed herein. In an example, the irrigated coupler 462 can include respective key slots. For example, the irrigated coupler 462 can include a key slot 473 defined in an inner wall of the irrigated coupler 462. The bottom connective stem portion 466 and the top connective stem portion 464 can be slid into the mounting lumen 530 such that the stem keys 472, 504 are aligned with a respective key slot 473, 505.

As depicted in FIGS. 9K to 9N, the irrigated coupler 462 can define a top irrigation manifold 534 and a bottom irrigation manifold 536. Upon assembly of the top connective stem portion 464 and the bottom connective stem portion 466 with the irrigated coupler 462, a top irrigation chamber can be formed via the top planar irrigation face 509 and the top irrigation manifold 534 and a bottom irrigation chamber can be formed via the bottom planar irrigation face 522 and the bottom irrigation manifold 536. Accordingly, an irrigation fluid can be introduced into the top irrigation chamber and the bottom irrigation chamber via the irrigation cross-over lumen 512. Upon introduction of fluid into the top irrigation chamber and the bottom irrigation chamber, the fluid can be expelled from respective irrigation ports (e.g., irrigation ports 477-1, 477-2).

Figure 9O:
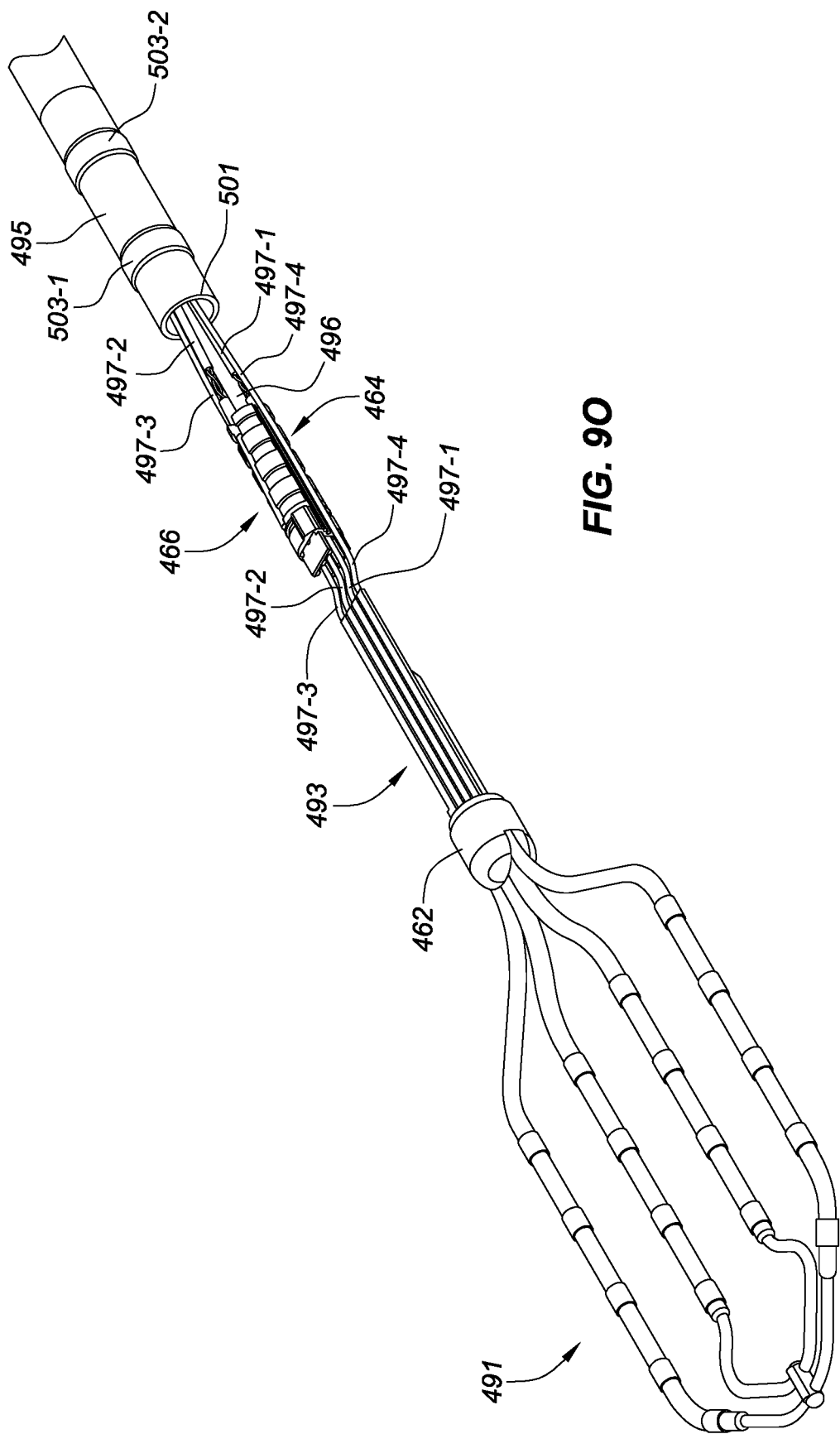
FIG. 9O depicts a flexible tip portion, irrigated coupler, top connective stem portion, and bottom connective stem portion prior to being inserted into a catheter shaft, according to embodiments of the present disclosure.

FIG. 9O depicts a flexible tip portion 491, irrigated coupler 462, top connective stem portion 464, and bottom connective stem portion 466 prior to being inserted into a catheter shaft 495, according to embodiments of the present disclosure. As depicted, the irrigated coupler 462 can be disposed at a proximal end of the flexible tip portion 491, between the flexible tip portion 491 and a proximal understructure 493. The proximal understructure 493 can be inserted between a top connective stem portion 464 and a bottom connective stem portion 466, as discussed herein, which can hold the proximal understructure 493 in fixed relation to the top connective stem portion 464 and the bottom connective stem portion 466. The top connective stem portion 464 and the bottom connective stem portion 466 can be inserted into the irrigated coupler 462, as previously discussed.

Figure 9P:
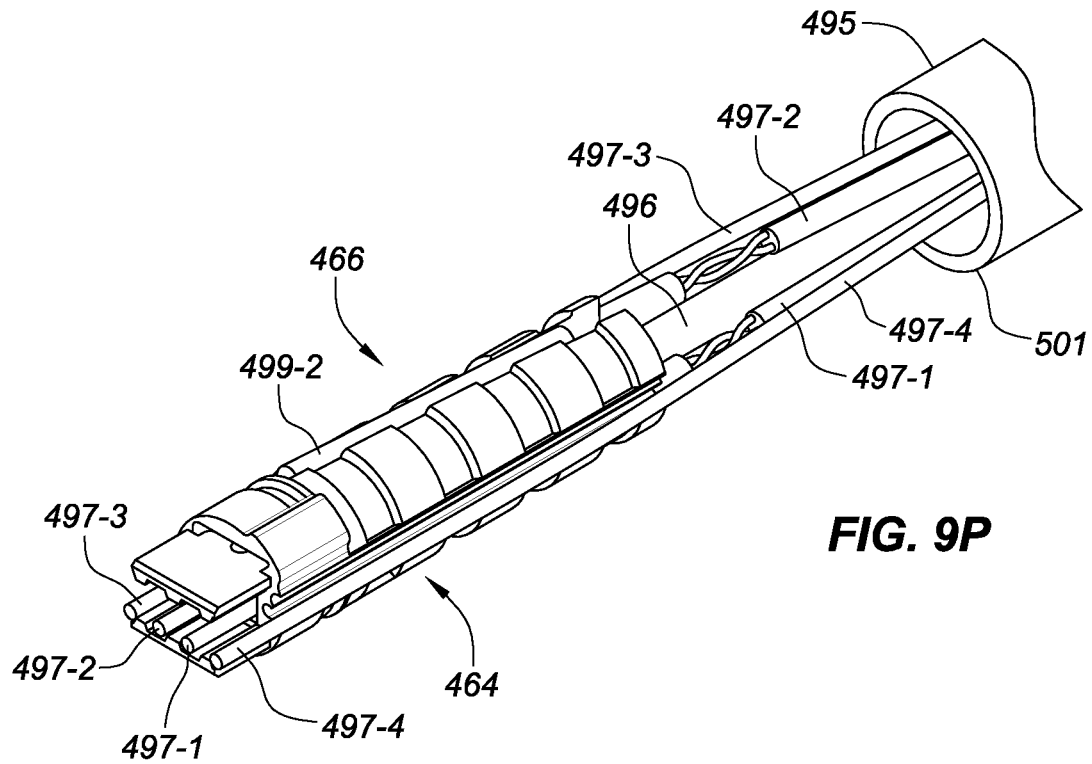
FIG. 9P depicts a bottom isometric side view of the bottom connective stem portion and top connective stem portion depicted in FIG. 9O, before insertion into a distal end of the catheter shaft, according to embodiments of the present disclosure.

In some embodiments, the top connective stem portion 464 can include a first five DOF magnetic position sensor 499-1 (FIG. 9Q) and the bottom connective stem portion 466 can include a second five DOF magnetic position sensor 499-2 (FIG. 9P). FIG. 9O depicts a first, second, third, and fourth set of wires/tubes carrying wires 497-1, 497-2, 497-3, 497-4, which can be associated with electrical elements (e.g., electrodes) disposed on the flexible tip portion 491. Additionally, FIG. 9O depicts an irrigation tube 496 that is connected to the top connective stem portion 464 and can provide a fluid to the irrigated coupler 462. Upon assembly, the irrigated coupler 462 can be connected with a distal end 501 of the catheter shaft 495. As further depicted, the catheter shaft 495 can include a first and second ring electrode 503-1, 503-2.

Figure 9Q:
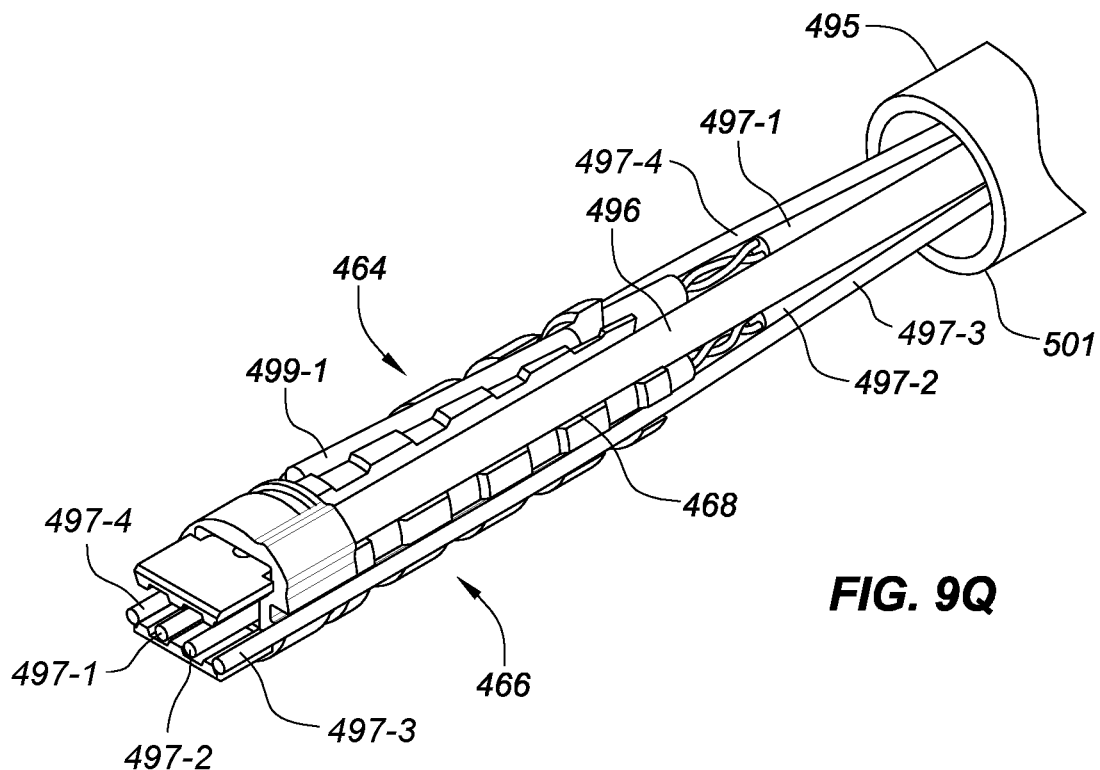
FIG. 9Q depicts a top isometric side view of the top connective stem portion and bottom connective stem portion depicted in FIG. 9O, before insertion into a distal end of the catheter shaft, according to embodiments of the present disclosure.

FIG. 9P depicts a bottom isometric side view of the bottom connective stem portion 466 and top connective stem portion 464 depicted in FIG. 9O, before insertion into a distal end 501 of the catheter shaft 495, according to embodiments of the present disclosure. FIG. 9Q depicts a top isometric side view of the top connective stem portion 464 and bottom connective stem portion 466 depicted in FIG. 9O, before insertion into a distal end 501 of the catheter shaft 495, according to embodiments of the present disclosure. As further depicted, a second five DOF magnetic position sensor 499-2 can be disposed within a respective sensor groove in the bottom connective stem portion 466 and a first five DOF magnetic position sensor 499-1 can be disposed within a respective sensor groove in the top connective stem portion 464. The irrigation tube 496 can be disposed in an irrigation channel 468.

Figure 10A:
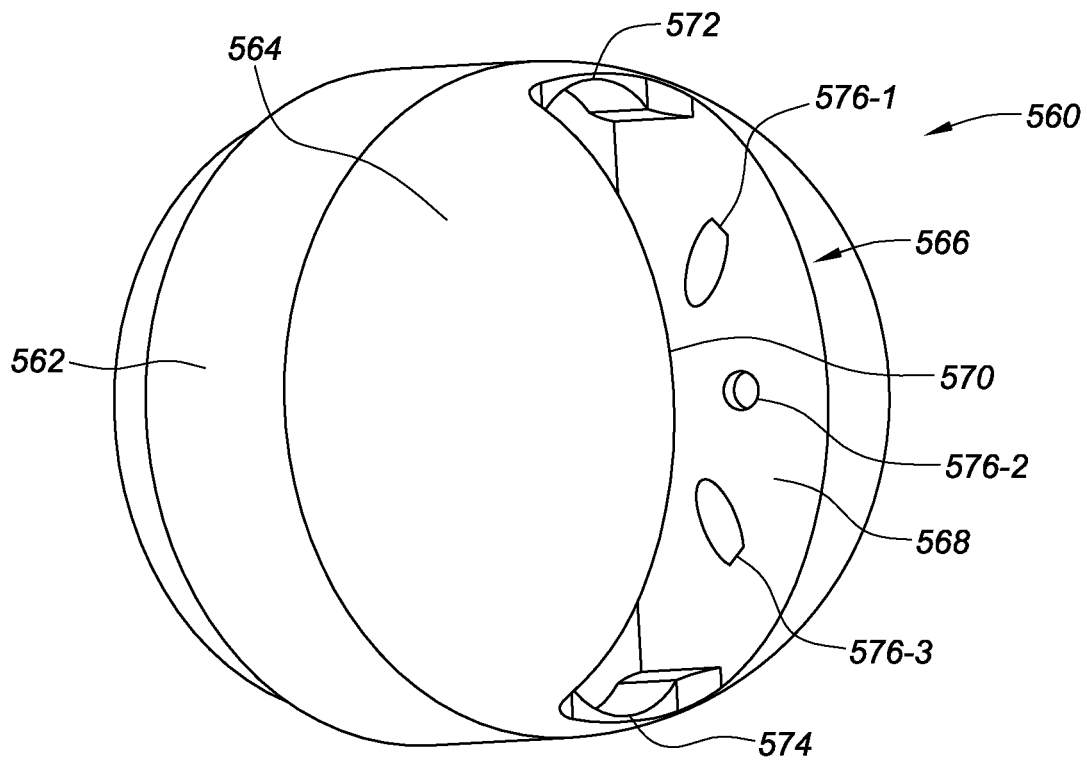
FIGS. 10A and 10B are isometric side and distal end views of an irrigated coupler, according to embodiments of the present disclosure.

FIG. 10A is an isometric side and distal end view of an irrigated coupler 560, according to embodiments of the present disclosure. In some embodiments, the irrigated coupler 560 can include a cylindrical body 562 that extends along a longitudinal axis. In some embodiments, the irrigated coupler 560 can include a proximal mounting feature 563 that proximally extends from the cylindrical body 562. A hemispherical head 564 can be connected to the cylindrical body 562. In some embodiments, a framework mounting slot 566 can be defined in the hemispherical head 564. In an example, a flexible framework can be disposed in the framework mounting slot 566 and can extend through the cylindrical body 562 and distally from the hemispherical head 564. The framework mounting slot 566 can be defined by a first planar slot wall 568 and a second planar slot wall 570. In some embodiments, the first planar slot wall 568 and/or the second planar slot wall 570 can be parallel with a longitudinal axis along which the irrigated coupler 560 extends. In some embodiments, the first planar slot wall 568 and the second planar slot wall 570 can be parallel with respect to one another. In some embodiments, the first planar slot wall 568 and the second planar slot wall 570 can be divergent with respect to one another. For example, the first planar slot wall 568 and the second planar slot wall 570 can extend away from one another in a proximal to distal direction. In some embodiments, this can allow for the flexible framework that distally extends from the irrigated coupler 560 to better flex in a direction perpendicular to the first planar slot wall 568 and/or second planar slot wall 570.

In some embodiments, the framework mounting slot 566 can be further defined by end slot walls 572, 574. In some embodiments, the end slot walls 572, 574 can include a curved interior face, which can be configured to accept the flexible framework. The end slot walls 572, 574 can extend distally from the cylindrical body 562, as depicted.

Figure 10B:
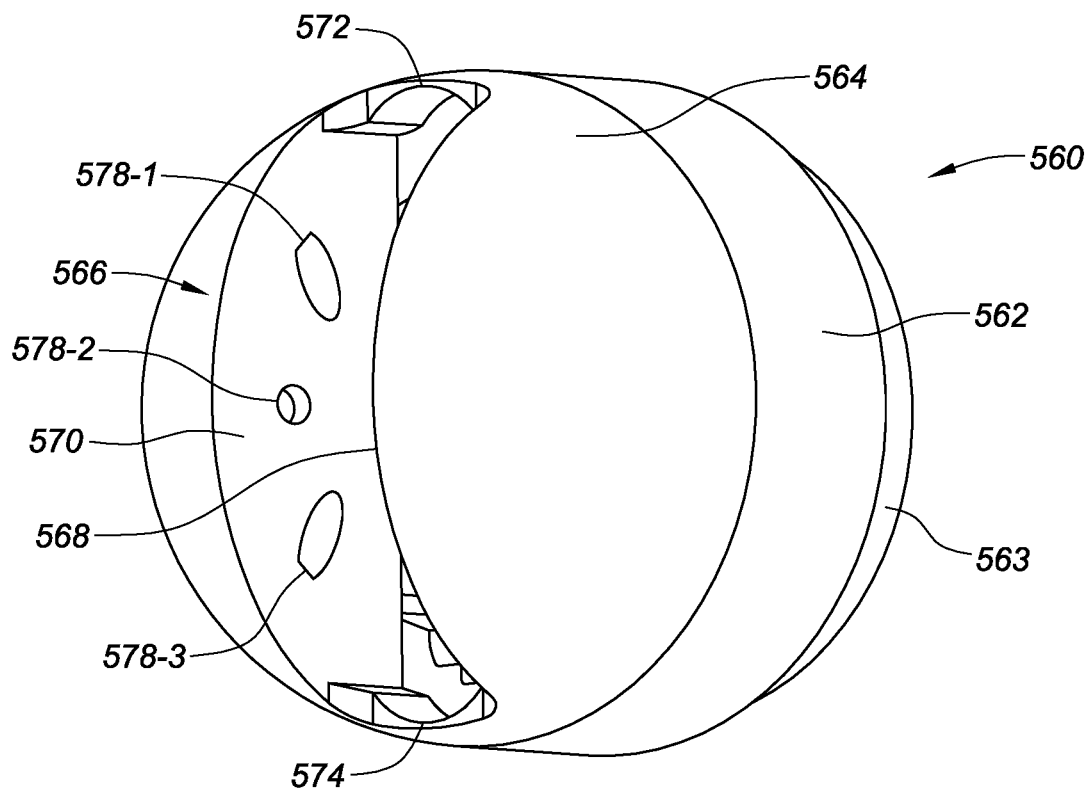
Figure 10C:
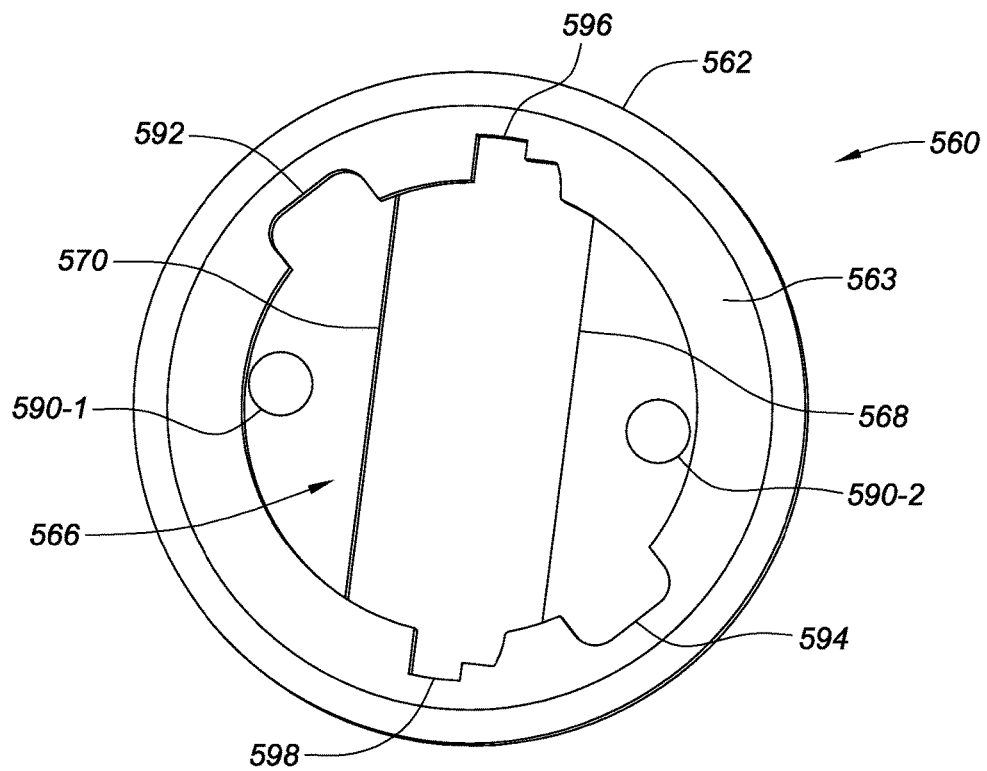
FIG. 10C is a rear view of the irrigated coupler depicted in FIGS. 10A and 10B, according to various embodiments of the present disclosure.

In some embodiments, a plurality of irrigation ports can be formed along each one of the planar slot walls 568, 570. As depicted, a first row of irrigation ports 576-1, 576-2, 576-3 can be defined in the first planar slot wall 568 and a second row of irrigation ports 578-1, 578-2, 578-3 can be defined in the second planar slot wall 570. In some embodiments, the first row of irrigation ports 576-1, 576-2, 576-3 can be fluidly coupled with a first irrigation lumen 590-1, depicted in FIG. 10C. In some embodiments, the second row of irrigation ports 578-1, 578-2, 578-3 can be fluidly coupled with a second irrigation lumen 590-2, as further depicted in FIG. 10C. FIG. 10C is a rear view of the irrigated coupler 560 depicted in FIGS. 10A and 10B, according to various embodiments of the present disclosure. Fluid can be provided to the first irrigation lumen 590-1 and the second irrigation lumen 590-2 and can be distributed to each one of the irrigation ports 576-1, 576-2, 576-3, 578-1, 578-2, 578-3 via the first irrigation lumen 590-1 and the second irrigation lumen 590-2, respectively.

In some embodiments, the proximal mounting feature can define first and/or second key slots 592, 594 in which stem keys can be disposed, as discussed herein. As further depicted, the irrigated coupler can define a pair of diametrically opposed slots 596, 598 in which a flexible framework can be disposed.

Figure 11A:
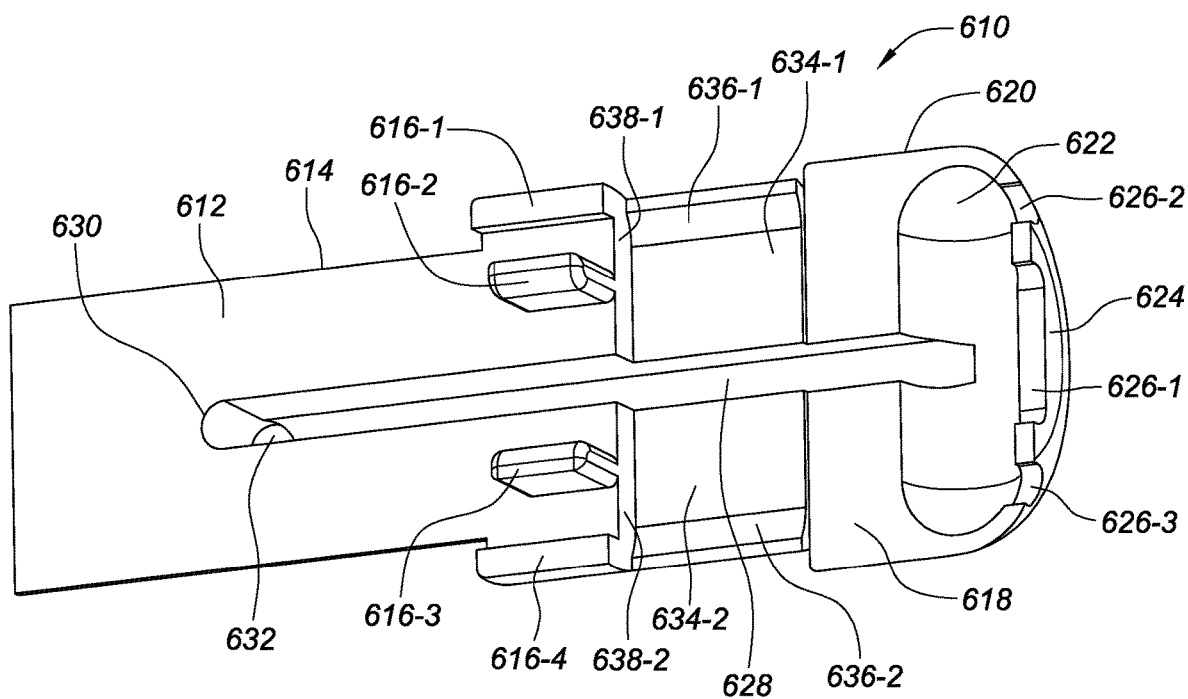
FIG. 11A depicts a bottom connective stem portion, according to embodiments of the present disclosure.

FIG. 11A depicts a bottom connective stem portion 610, according to embodiments of the present disclosure. In some embodiments, the bottom connective stem portion 610 can extend along a longitudinal axis and can be hemi cylindrical in shape. In an example, an exterior surface of the bottom connective stem portion 610 can be hemi cylindrical and an interior surface of the bottom connective stem portion 610 can be a planar surface. For example, a first interior surface 612 of a bottom body portion 614 can be a planar surface that is parallel with a longitudinal axis along which the bottom connective stem portion 610 extends. In some embodiments, one or more framework dividers 616-1, 616-2, 616-3, 616-4 (e.g., ridges) can extend perpendicular to the first interior planar surface 612. In some embodiments, the framework dividers 616-1, 616-2, 616-3, 616-4 can separate each member of a flexible framework that is held via the bottom connective stem portion 610.

In some embodiments, a distal portion of the first interior surface 612 located distally with respect to the framework dividers 616-1, 616-2, 616-3, 616-4 can be recessed, thus forming bottom recessed faces 634-1, 634-2. In an example, outer retention features 636-1, 636-2 can be disposed at the outer lateral edges of the bottom recessed faces 634-1, 634-2, respectively. In some embodiments, an understructure (e.g., flexible framework) can be disposed between the bottom connective stem portion 610 and a top connective stem portion 640, depicted in FIG. 11B. In some embodiments, a housing (e.g., tube, covering) can be disposed over the understructure, as discussed in relation to FIG. 8D. The housing can have a greater thickness in some embodiments than the understructure and can be disposed between the outer retention features 636-1, 636-2 and the bottom recessed faces 634-1, 634-2.

In some embodiments, the bottom connective stem portion 610 can include an irrigated head 620 that extends distally from a distal end of the bottom body portion 614. In some embodiments, the bottom connective stem portion 610 can include a second interior surface 618. For example, the irrigated head can include the second interior surface 618, which can be a planar surface. In some embodiments, a recessed bottom manifold 622 can be defined in the second interior face 618. The irrigated head 620 can include a distal face in which one or more irrigation ports can be defined. As depicted in FIG. 11A, the distal face 624 includes a first elongated irrigation port 626-1 and a second irrigation port 626-2 and third irrigation port 626-3 defined in the distal face 624 on either side of the first elongated irrigation port 626-1.

In some embodiments, the recessed bottom manifold 622 and the irrigation ports 626-1, 626-2, 626-3 can be in fluid communication with an irrigation channel 628. The irrigation channel 628 can be defined in an interior surface of the bottom connective stem portion 610. For example, the irrigation channel 628 can axially and distally extend from a proximal channel wall 630 to the recessed bottom manifold 622.

Figure 11B:
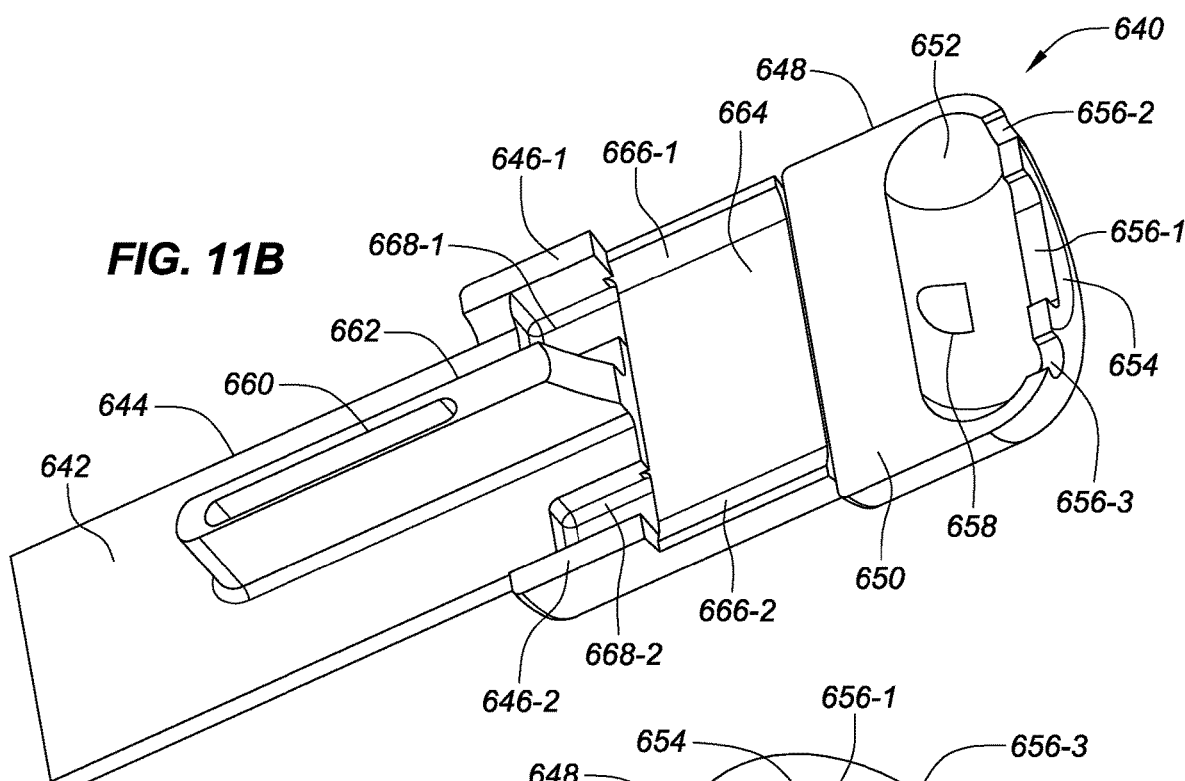
FIG. 11B depicts a top connective stem portion, according to embodiments of the present disclosure.

FIG. 11B depicts a top connective stem portion 640, according to embodiments of the present disclosure. In some embodiments, the top connective stem portion 640 can extend along a longitudinal axis and can be hemi cylindrical in shape. In an example, an exterior surface of the top connective stem portion 640 can be hemi cylindrical and an interior surface of the bottom connective stem portion 610 can be a planar surface. For example, a first interior surface 642 of a top body portion 644 can be a planar surface that is parallel with a longitudinal axis along which the top connective stem portion 640 extends. In some embodiments, one or more framework dividers 646-1, 646-2 (e.g., ridges) can extend perpendicular to the first interior planar surface. In some embodiments, the framework dividers 646-1, 646-2 can separate each member of a flexible framework that is held via the top connective stem portion 640. In some embodiments, divider recesses 668-1, 668-2 can be defined in a distal portion of the first interior surface 642. In an example, the divider recesses 668-1, 668-2 can be configured to accept the framework dividers 616-2, 616-3 when the bottom connective stem portion 610 and the top connective stem portion 640 are assembled.

In some embodiments, a distal portion of the interior surface 642 located distally with respect to the framework dividers 646-1, 646-2 can be recessed, thus forming a top recessed face 664. In an example, outer retention features 666-1, 666-2 can be disposed at the outer lateral edges of the recessed face 664, respectively. In some embodiments, an understructure (e.g., flexible framework) can be disposed between the top connective stem portion 640 and the bottom connective stem portion 610, depicted in FIG. 11A. In some embodiments, a housing (e.g., tube, covering) can be disposed over the understructure, as discussed in relation to FIG. 8D. The housing can have a greater thickness in some embodiments than the understructure and can be disposed between the outer retention features 666-1, 666-2 and the top recessed face 664. As further depicted in FIGS. 11C and 11D, the top connective stem portion 640 and the bottom connective stem portion 610 can be connected. Thus, the understructure and housing covering the understructure can be disposed between the bottom recessed faces 634-1, 634-2 and the top recessed face 664 and can be prevented from moving laterally via the outer retention features 636-1, 636-2, 666-1, 666-2.

In some embodiments, the top connective stem portion 640 can include an irrigated head 648 that extends distally from a distal end of the top body portion 644. In some embodiments, the top connective stem portion 640 can include a second interior surface 650. For example, the irrigated head 648 can include the second interior surface 650, which can be a planar surface. In some embodiments, a recessed top manifold 652 can be defined in the second interior face 650. The irrigated head 648 can include a distal face 654 in which one or more irrigation ports can be defined. As depicted in FIG. 11B, the distal face 654 includes a first elongated irrigation port 656-1 and can further define a second irrigation port 656-2 and third irrigation port 656-3 in the distal face 654 on either side of the first elongated irrigation port 656-1.

In some embodiments, the recessed top manifold 652 and the irrigation ports 656-1, 656-2, 656-3 can be in fluid communication with a top irrigation lumen 658. The top irrigation lumen 658 can extend proximally to a proximal end of the top connective stem portion 640. In some embodiments, the top irrigation lumen 658 can be in fluid communication with an elongate cross-over lumen 660 defined in a cross-over manifold 662. As further depicted herein, the cross-over manifold can be configured to fit within the irrigation channel 632 of the bottom connective stem portion 610. In an example, an irrigation fluid can be provided from a proximal end of the top connective stem portion 640 and can travel through the top irrigation lumen 658 and into the recessed top manifold 652 and out the irrigation ports 656-1, 656-2, 656-3. Additionally, the irrigation fluid can travel into the elongate cross-over lumen 660, which is in fluid communication with the top irrigation lumen 658. The irrigation fluid can then flow from the elongate cross-over lumen 660 and into the irrigation channel 628 and along the irrigation channel 628 into the recessed bottom manifold 622 and through the irrigation ports 626-1, 626-2, 626-3.

Figure 11C:
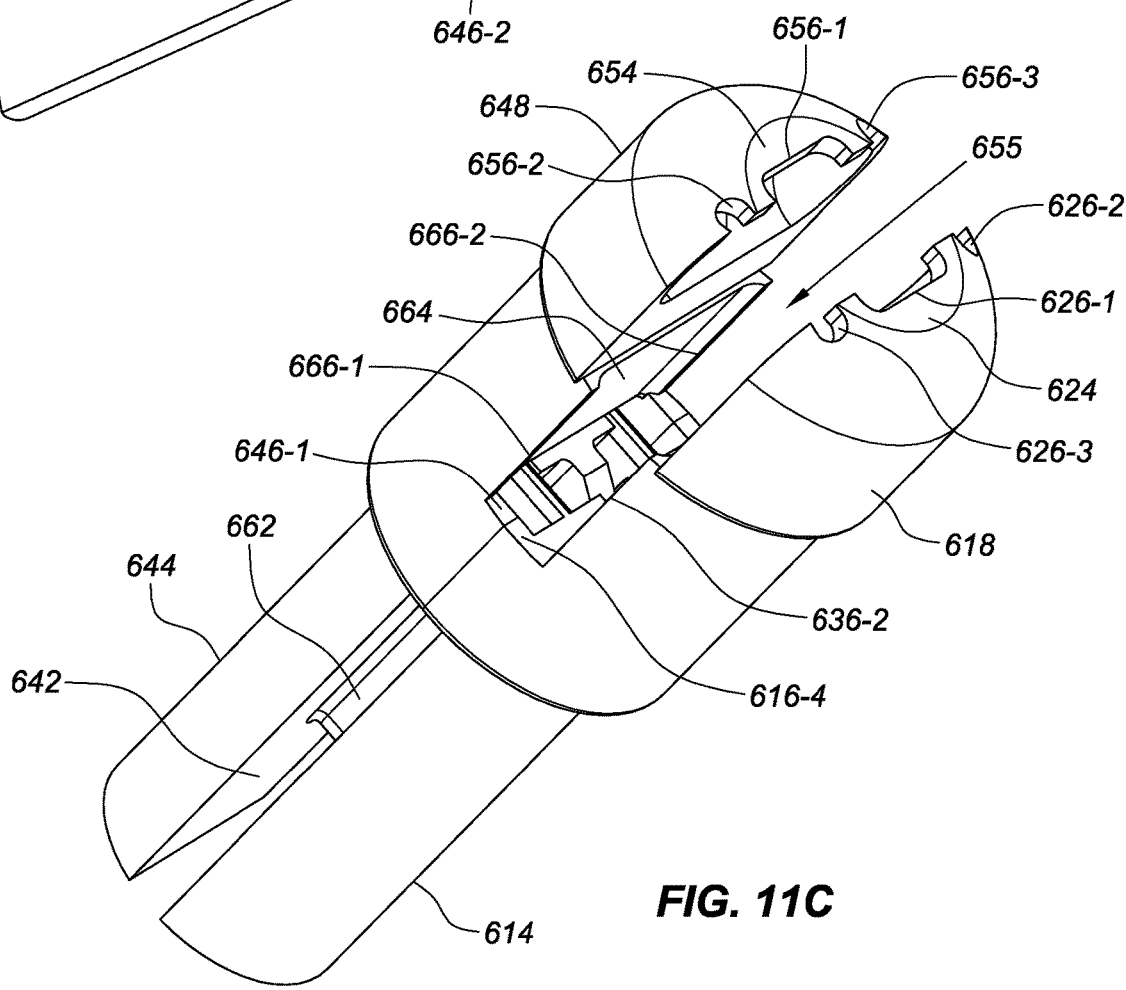
FIG. 11C depicts the bottom connective stem portion and the top connective stem portion depicted in FIGS. 11A and 11B upon assembly, according to various embodiments of the present disclosure.

FIG. 11C depicts the bottom connective stem portion 610 and the top connective stem portion 640 in FIGS. 11A and 11B upon assembly, according to various embodiments of the present disclosure. As depicted, a slot 655 can be defined via the top recessed face 664 and the outer retention features 666-1, 666-2 and the bottom recessed faces 634-1, 634-2 and outer retention features 636-1, 636-2. In some embodiments, a housing that covers the understructure can be positioned within the slot 655, such as that discussed in relation to FIG. 8D.

Figure 11D:
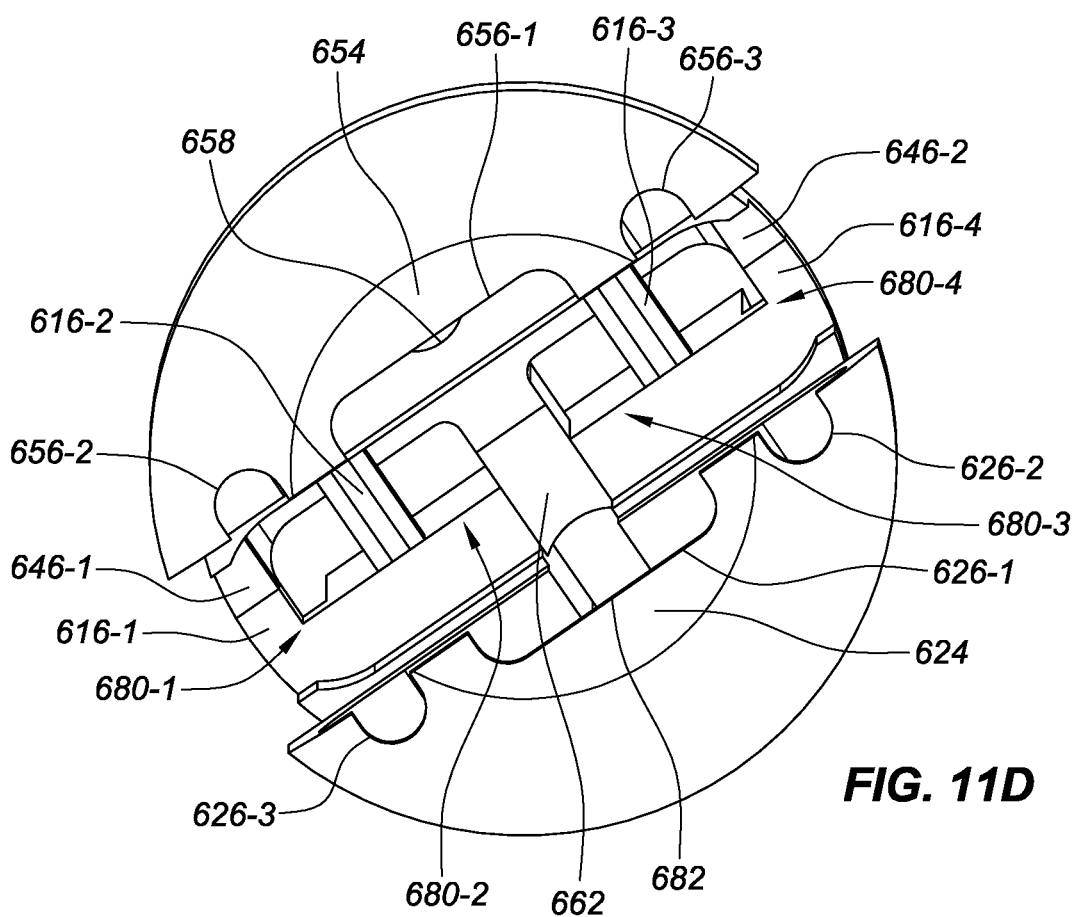
FIG. 11D is a distal end view of the bottom connective stem portion and the top connective stem portion as depicted in FIGS. 11A to 11C upon assembly, according to various embodiments of the present disclosure.

FIG. 11D is a distal end view of the bottom connective stem portion 610 and the top connective stem portion 640 upon assembly, according to various embodiments of the present disclosure. As depicted, the framework dividers 616-1, 616-2, 616-3, 616-4, 646-1, 646-2, and the cross-over manifold 662 can define framework passages 680-1, 680-2, 680-3, 680-4. A framework associated with an understructure can be disposed in the framework passages 680-1, 680-2, 680-3, 680-4, and the framework can be fixedly held in place with respect to the bottom connective stem portion 610 and the top connective stem portion 640.

Also depicted in FIG. 11D is a bottom irrigation lumen 682. The bottom irrigation lumen can provide an irrigation fluid to the recessed bottom manifold 622 and through the irrigation ports 626-1, 626-2, 626-3. In some embodiments, the bottom irrigation lumen 682 can be formed when the cross-over manifold 662 is disposed within the irrigation channel 628. In an example, a supply of irrigation fluid can be provided via a source lumen 692 (FIG. 11E) that longitudinally extends through the top connective stem portion 640, as further depicted in FIG. 11E. The top irrigation lumen 658 and the cross-over lumen 660 can be fluidly coupled with the longitudinally extending lumen. Accordingly some of the irrigation fluid can flow into the recessed top manifold 652 and through the irrigation ports 656-1, 656-2, 656-3; and some of the irrigation fluid can flow out of the cross-over lumen 660 and into the bottom irrigation lumen 682 formed by the cross-over manifold 662 and the irrigation channel 628. The irrigation fluid can flow distally through the bottom irrigation lumen 682 and into the recessed bottom manifold 622 and through the irrigation ports 626-1, 626-2, 626-3.

Figure 11E:
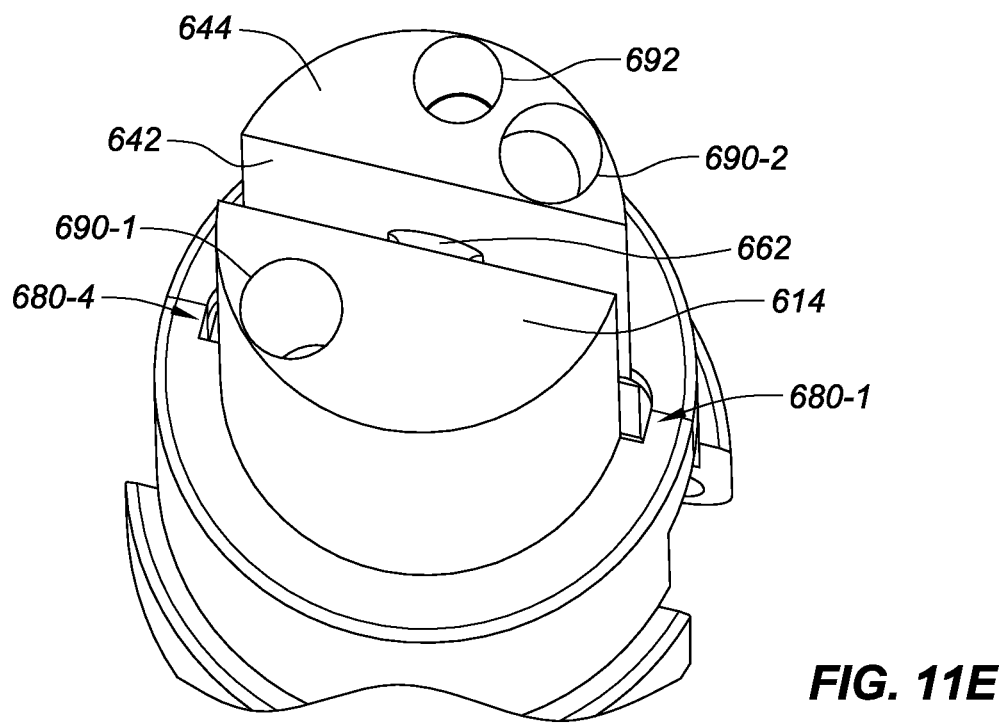
FIG. 11E is an isometric distal end view of the bottom connective stem portion and the top connective stem portion previously depicted in FIGS. 11A to 11D upon assembly, according to various embodiments of the present disclosure.

FIG. 11E is an isometric distal end view of the bottom connective stem portion 610 and the top connective stem portion 640 upon assembly, according to various embodiments of the present disclosure. As depicted, the top connective stem portion 640 can define a source lumen 692 that longitudinally extends therethrough. In some embodiments, an irrigation fluid can flow through the source lumen 692 and can be provided to the cross-over lumen 660 and to the top irrigation lumen 658. As further depicted, the bottom connective stem portion 610 and the top connective stem portion 640 can each define sensor lumens 690-1, 690-2. The sensor lumens 690-1, 690-2 can each extend longitudinally through the bottom connective stem portion 610 and the top connective stem portion 640. In some embodiments, the sensor lumens 690-1, 690-2 can be disposed at an angle with respect to one another, as previously discussed herein, for example in relation to FIGS. 9A and 9B. As depicted, the sensor lumens 690-1, 690-2 are disposed internally within the bottom connective stem portion 610 and the top connective stem portion 640. In some embodiments, the sensor lumens 690-1, 690-2 can be blind lumens. For example, the sensor lumens 690-1, 690-2 can be formed in a distal end of the bottom connective stem portion 610 and the top connective stem portion 640 and can extend distally into each one of the bottom connective stem portion 610 and the top connective stem portion 640.

Figure 12A:
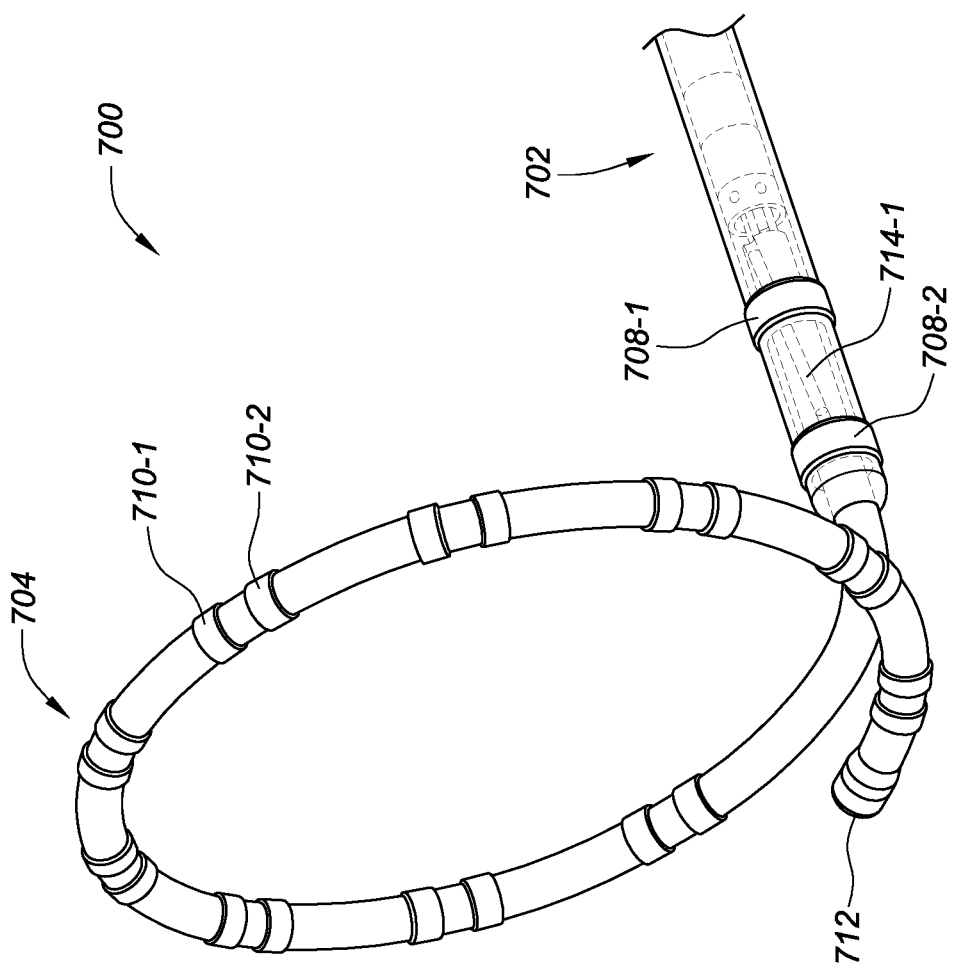
FIG. 12A is an isometric side and end view of a medical device that includes an elongate shaft and a looped distal end, according to various embodiments of the present disclosure.

FIG. 12A is an isometric side and end view of a medical device that includes an elongate shaft 702 and a looped distal end 704, according to various embodiments of the present disclosure. In some embodiments, the elongate shaft 702 can be a steerable shaft that is flexible. For example, a number of pull wires can extend through one or more portions of the elongate shaft 702 and can be actuated to cause the elongate shaft 702 to deflect in one or more directions. In some embodiments, one or more electrodes 708-1, 708-2 can be disposed about the elongate shaft 702. In some embodiments, the electrodes 708-1, 708-2 can be diagnostic electrodes (e.g., sensing) and/or therapeutic electrodes (e.g., configured to deliver energy to a tissue).

In some embodiments, the looped distal end 704 can be connected to a distal end of the elongate shaft 702 and can have a distal tip 712. The looped distal end 704 can be formed from a flexible material. In some embodiments, the looped distal end 704 can be configured to alter its shape via one or more pull wires that extend through the looped distal end 704. For example, in some embodiments, a diameter of looped distal end 704 can be increased and/or decreased in some embodiments via actuation of one or more pull wires that extend through the looped distal end 704. The looped distal end 704 can include one or more electrodes in some embodiments. For example, one or more electrodes 710-1, 710-2 can be disposed about the looped distal end 704.

In some embodiments, a pair of magnetic position sensors can be disposed within the elongate shaft 702. As depicted in FIG. 12A, a first magnetic position sensor 714-1 is disposed within the elongate shaft 702. As previously discussed herein, the pair of magnetic position sensors can be disposed at an angle with respect to one another. Each one of the magnetic position sensors can be a 5 DOF sensor, but because the sensors are disposed at an angle with respect to one another, signals generated by each one of the two 5 DOF sensors can be analyzed to determine a position of the pair of sensors with 6 DOF.

Figure 12B:
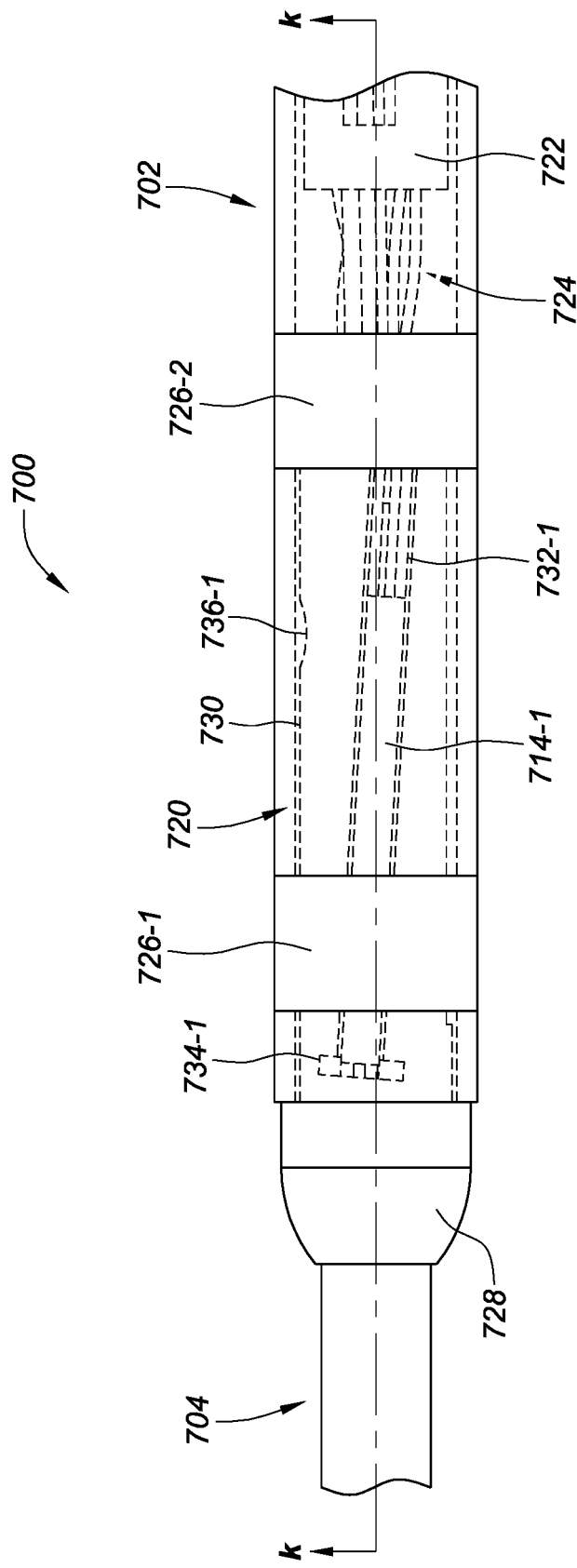
FIG. 12B is a side view of the medical device in FIG. 12A that includes a coupler disposed in a distal end of the elongate shaft that is coupled to a proximal end of the looped distal end, according to various embodiments of the present disclosure.

FIG. 12B is a side view of the medical device 700 in FIG. 12A that includes a coupler 720 disposed in a distal end of the elongate shaft 702 that is coupled to a proximal end of the looped distal end 704, according to various embodiments of the present disclosure. The elongate shaft 702 can define an elongate shaft longitudinal axis in some embodiments and the coupler 720 can define a coupler longitudinal axis, which in some embodiments can share the same axis as the elongate shaft longitudinal axis. As depicted, the elongate shaft 702 can include a pull ring 722, to which pull wires can be connected. As previously discussed, upon actuation of the pull wires, the elongate shaft 702 can be deflected in some embodiments. A plurality of wires and/or tubes 724 can extend through a center of the pull ring 722. In an example, the wires can be electrically coupled with one or more sensors and/or electrodes (e.g., ring electrodes 726-1, 726-2) in some embodiments and the tubes can be configured to provide an irrigation fluid to a distal end of the medical device 700.

The coupler 720, in some embodiments, can couple the looped distal end 704 to the distal end of the elongate shaft 702. The coupler 720 can have a proximal end 742 (FIG. 12C) and a distal tip 728 and can axially extend along a longitudinal axis. In an example, a body portion 730 can be inserted into a distal end of the elongate shaft 702. In some embodiments, the distal end 704 can have a diameter that is greater than the body portion 730 and greater than an inner diameter of the elongate shaft 702, such that the distal end 704 prevents the coupler from being inserted too far into the elongate shaft 702.

In some embodiments, the coupler 720 can define a first sensor groove 732-1 and a second sensor groove 732-2 (FIG. 12C) in which a first sensor 714-1 and a second sensor 714-2 (FIG. 12C) can be disposed. As discussed herein, the first sensor groove 732-1 and the second sensor groove 732-2 can be formed at angles with respect to one another and the first sensor 714-1 and the second sensor 714-2 can be disposed within the first sensor groove 732-1 and the second sensor groove 732-2, such that the first sensor 714-1 and the second sensor 714-2 are disposed at angles with respect to one another.

Figure 12C:
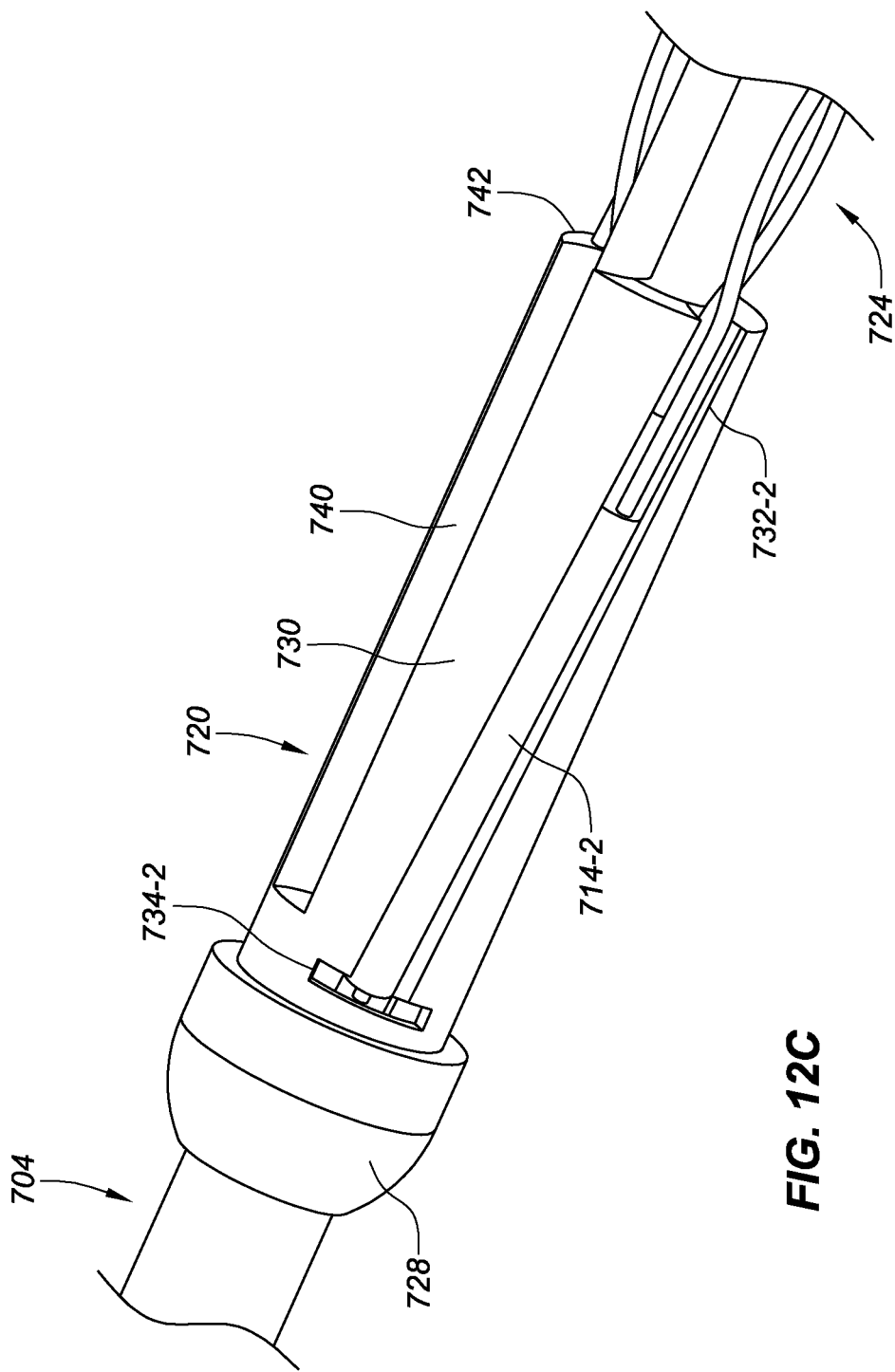
FIG. 12C is an isometric side and rear view of the coupler depicted in FIG. 12B, according to embodiments of the present disclosure.

As depicted, placement slots (e.g., first placement slot 734-1, second placement slot 734-2 depicted in FIG. 12C) can be defined in an outer surface of the body portion 730 of the coupler 720. A placement slot can be located at the distal end of each sensor groove. For example, with respect to the first sensor groove 732-1, the first placement slot 734-1 can be located at the distal end of the first sensor groove 732-1. In some embodiments, as depicted, the first placement slot 734-1 can be a cross-longitudinal slot defined in the exterior surface of the body portion 730. In an example, the placement slots can extend perpendicular to each one of the sensor grooves. For instance, as depicted with respect to the first placement slot 734-1, the first placement slot 734-1 can extend perpendicular to the first sensor groove 732-1.

In some embodiments, the first placement slot 734-1 can provide an indication of whether the first sensor 714-1 has been correctly placed within the first sensor groove 732-1. In an example, an accurate determination of a position of the medical device can be dependent on a placement of the first sensor 714-1 with respect to one or more of the ring electrodes 726-1, 726-2. For instance, an axial placement of the sensor with respect to the one or more of the ring electrodes 726-1, 726-2 should be consistent. Accordingly, the first placement slot 734-1 allows for a visual inspection for correct placement of the first sensor 714-1. For example, as further discussed herein, the first sensor 714-1 can be disposed within the first sensor groove 732-1 such that a distal end of the first sensor 714-1 is disposed within the first placement slot 734-1. Upon a visual inspection, the placement of the distal end of the first sensor 714-1 in the first placement slot 734-1 can be verified, thus confirming a correct placement of the first sensor 714-1.

In some embodiments, the body portion 730 can define a plurality of holes (e.g., first hole 736-1) in the body portion 730. A second hole 736-2 (FIG. 12E) is defined in the body portion, but is hidden from view in FIG. 12B by the ring electrode 726-1. As further discussed in relation to 12E, the holes 736-1, 736-2 can provide passageways in which an adhesive can be introduced to a longitudinally extending slot formed in the body portion 730, as further discussed below.

FIG. 12C is an isometric side and rear view of the coupler 720 depicted in FIG. 12B, according to embodiments of the present disclosure. As depicted, a plurality of wires and/or tubes 724 can extend from a distal end of the coupler 720. As discussed, the wires can be electrically coupled with one or more sensors and/or electrodes (e.g., ring electrodes 726-1, 726-2) in some embodiments and the tubes can be configured to provide an irrigation fluid to a distal end of the medical device 700.

The coupler 720 can have a proximal end (FIG. 12C) and a distal tip 728 and can axially extend along a longitudinal axis. In some embodiments, the coupler 720 can define a first sensor groove 732-1 (FIG. 12B) and a second sensor groove 732-2 in which a first sensor 714-1 and a second sensor 714-2 (FIG. 12C) can be disposed. As discussed herein, the first sensor groove 732-1 and the second sensor groove 732-2 can be formed at angles with respect to one another and the first sensor 714-1 and the second sensor 714-2 can be disposed within the first sensor groove 732-1 and the second sensor groove 732-2, such that the first sensor 714-1 and the second sensor 714-2 are disposed at angles with respect to one another.

As depicted, placement slots (e.g., first placement slot 734-1 depicted in FIG. 12B, second placement slot 734-2) can be defined in an outer surface of the body portion 730 of the coupler 720. A placement slot can be located at the distal end of each sensor groove. For example, with respect to the second sensor groove 732-2, the second placement slot 734-2 can be located at the distal end of the second sensor groove 732-2. In some embodiments, as depicted, the second placement slot 734-2 can be a cross-longitudinal slot defined in the exterior surface of the body portion 730. In an example, the placement slots can extend perpendicular to each one of the respective sensor grooves, although not required. For instance, as depicted with respect to the second placement slot 734-2, the second placement slot 734-2 can extend perpendicular to the second sensor groove 732-2.

In some embodiments, the second placement slot 734-2 can provide an indication of whether the second sensor 714-2 has been correctly placed within the second sensor groove 732-2. For example, in some embodiments, an accurate determination of a position of the medical device can be dependent on a placement of the second sensor 714-2 with respect to one or more of the ring electrodes 726-1, 726-2. For instance, an axial placement of the sensor with respect to the one or more of the ring electrodes 726-1, 726-2 should be consistent. Accordingly, the second placement slot 734-2 allows for a visual inspection for correct placement of the second sensor 714-2.

In some embodiments, the coupler 720 can include a longitudinally extending channel 740. The longitudinally extending channel 740 can extend along the body portion 730 of the coupler 720. For example, the longitudinally extending channel 740 can be defined in an outer surface of the body portion of the coupler 720. In some embodiments, the plurality of wires and/or tubes 724 can be disposed within the longitudinally extending channel 740. In some embodiments, a flex circuit can be disposed within the longitudinally extending channel 740, which can allow for the flex circuit to be aligned with the first sensor 714-1 and second sensor 714-2.

Figure 12D:
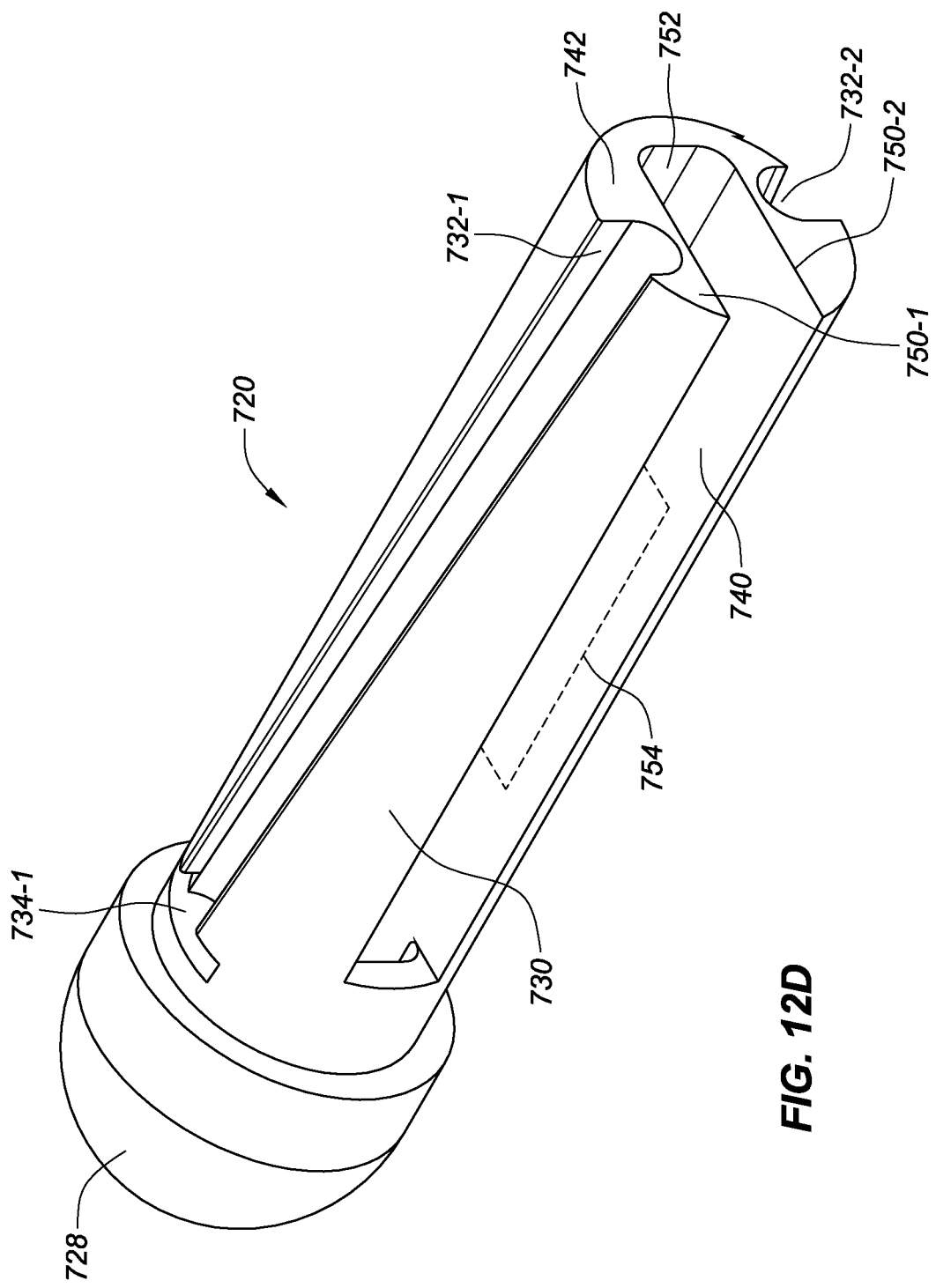
FIG. 12D is an isometric bottom and rear view of the coupler depicted in FIGS. 12B and 12C, according to embodiments of the present disclosure.

FIG. 12D is an isometric bottom and rear view of the coupler 720 depicted in FIGS. 12B and 12C, according to embodiments of the present disclosure. As previously discussed, the coupler 720 can include a distal tip 728 and a proximal end 742. A body portion 730 can be coupled to a proximal end of the distal tip 728 and in some embodiments can have a diameter that is less than the distal tip 728. However, in some embodiments, the diameter of the body 730 can be equal to or greater than that of the distal tip 728. The body portion 730 can define a first sensor groove 732-1 and a second sensor groove 732-2 in an exterior surface of the body portion 730. Alternatively, sensor grooves can be blind holes that extend from a proximal end 742 of the coupler 720. A first and second placement slot 734-1, 734-2 can be defined at a distal end of each one of the sensor grooves 732-1, 732-2, as previously discussed herein.

In some embodiments, a longitudinally extending channel 740 can extend through a portion of the body portion 730. In an example, as depicted, the longitudinally extending channel 740 can be defined by a pair of inner side walls 750-1, 750-2 and an inner top wall 752. As depicted, the pair of inner side walls 750-1, 750-2 can be parallel in some embodiments, although not required. For example, the pair of inner sidewalls 750-1, 750-2 can be divergent in some embodiments, forming a flared channel where a distance between the pair of inner sidewalls 750-1, 750-2 narrows towards the inner top wall 752 and/or forming a contracted channel where a distance between the pair of inner sidewalls 750-1, 750-2 increases towards the inner top wall 752.

In some embodiments, a flex circuit can be disposed within the longitudinally extending channel 740. In an example, the flex circuit can be disposed on one or more of the pair of inner sidewalls 750-1, 750-2 and inner top wall 752. For instance, the flex circuit can be disposed on the second inner sidewall 750-2 in the region 754 identified by the dotted line. However, the flex circuit can be disposed in other locations in the longitudinally extending channel 740. In some embodiments, the flex circuit can protrude from the proximal end 742 to allow for an electrical connection between the flex circuit to a set of wires and/or an additional circuit.

In some embodiments, the coupler 720 can include an ultrasound transducer. For example, in place of or in addition to the flexible tip portion 110 of FIG. 1A and/or the looped distal end 704 of FIG. 12A, the coupler 720 can include an ultrasound transducer. In an example, the ultrasound transducer can be electrically coupled and/or mechanically fixed to a flex circuit. For instance, the ultrasound transducer can be electrically coupled and/or mechanically fixed to the flex circuit disposed within the region 754.

Figure 12E:
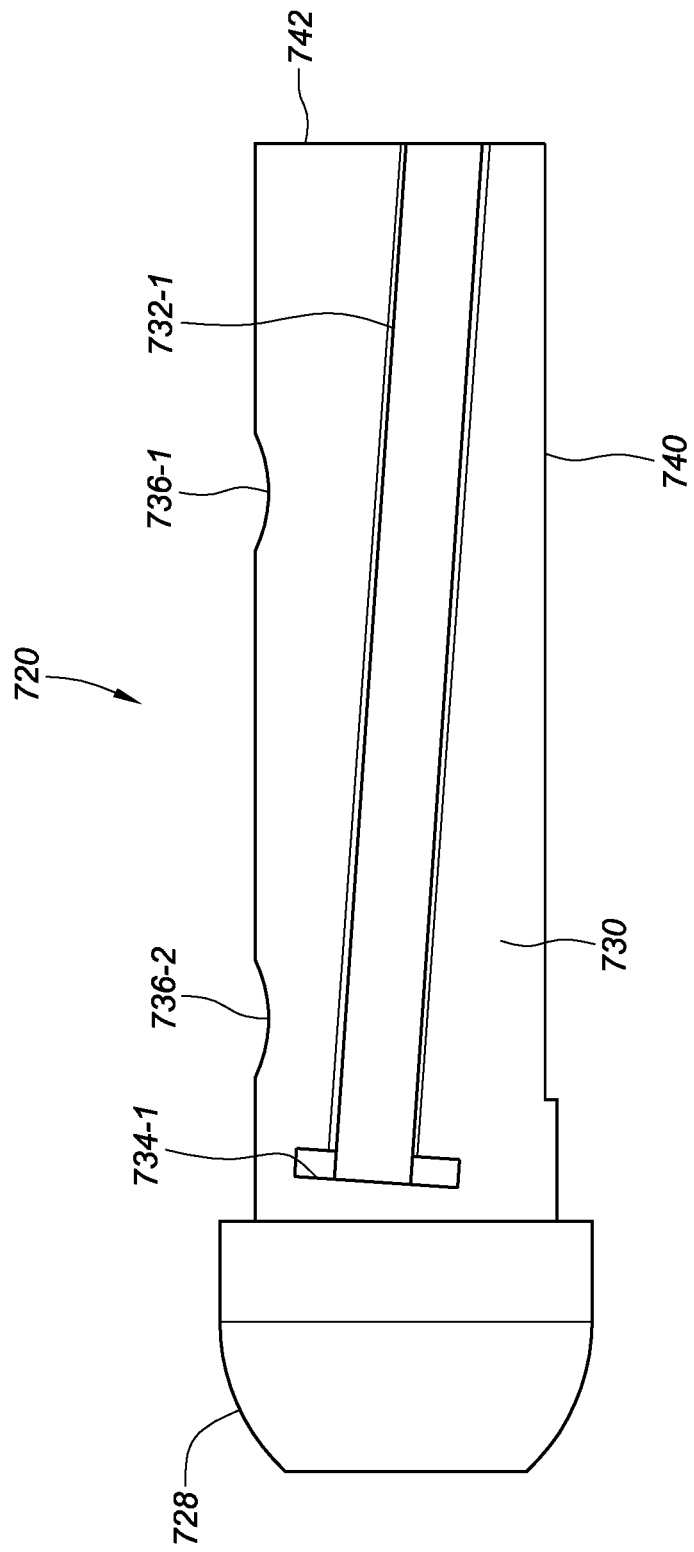
FIG. 12E is a side view of the coupler depicted in FIGS. 12B and 12D, according to embodiments of the present disclosure.

FIG. 12E is a side view of the coupler 720 depicted in FIGS. 12B and 12D, according to embodiments of the present disclosure. As previously discussed, the coupler 720 can include a distal tip 728 and a body portion 730 that includes a proximal end 742 and a distal end, the distal end of which is connected to the distal tip 738. As depicted, the body portion 730 can define a first sensor groove 732-1 and a first placement slot 734-1 located at a distal end of the first sensor groove 732-1.

In some embodiments, a first hole 736-1 and a second hole 736-2 can be formed along a side of the body portion. In some embodiments, the first and second hole 736-1, 736-2 can be axially aligned with a longitudinal axis of the coupler 720. In an example, the first hole and second hole 736-1, 736-2 can be defined in the inner top wall 752 (FIG. 12D) and can extend through an external surface of the body portion 730, thus providing access to the longitudinally extending channel 740. In some embodiments, the first and second holes 736-1, 736-2 can act as fill holes, allowing access to the longitudinally extending channel 740 for the placement of additional adhesive in the longitudinally extending channel, especially in a center area of the longitudinally extending channel 740. In some embodiments that do not include the first and second holes 736-1, 736-2, it can be difficult to ensure that every portion of the longitudinally extending channel 740 is potted with an adhesive. Accordingly, an adhesive can be introduced to the longitudinally extending channel 740 via the first and second holes to ensure that the longitudinally extending channel 740 is filled with adhesive.

Figure 12F:
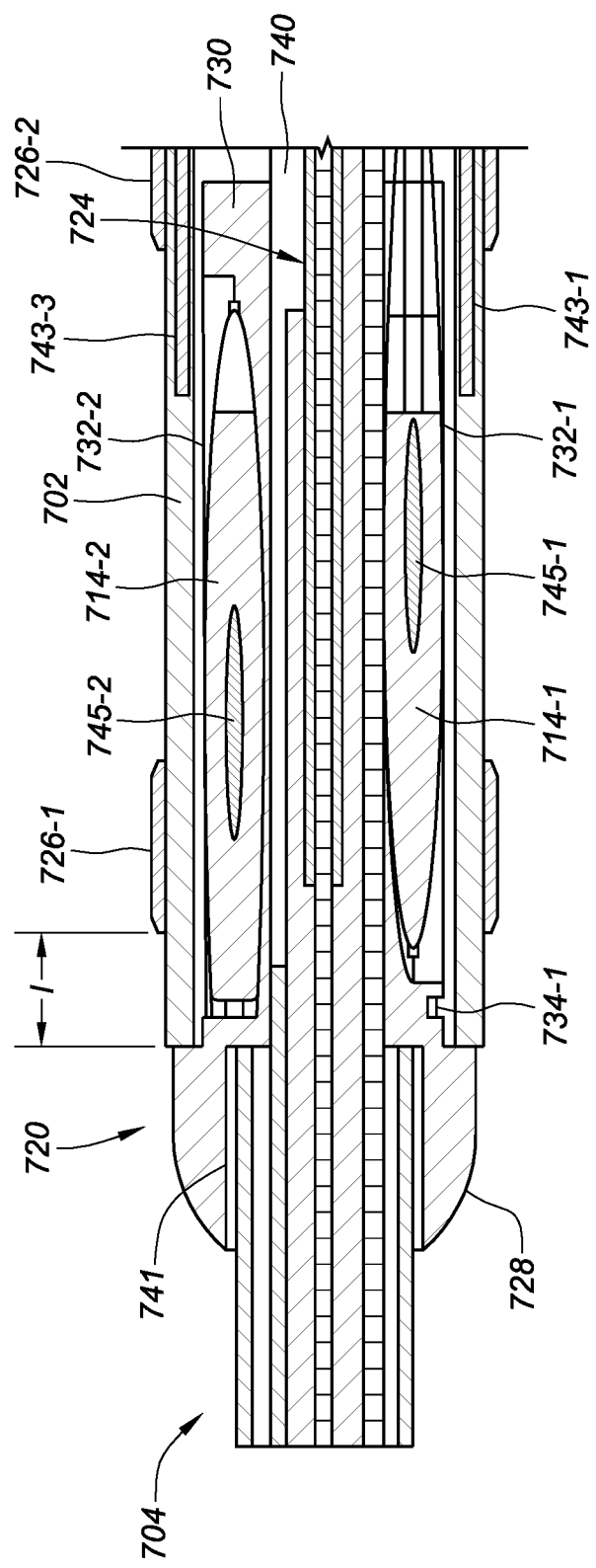
FIG. 12F is a cross-sectional schematic view of FIG. 12B in the direction of line kk, according to embodiments of the present disclosure.

FIG. 12F is a cross-sectional schematic view of FIG. 12B in the direction of line kk, according to embodiments of the present disclosure. As depicted, the coupler 720 can be disposed in a lumen defined by a distal end of an elongate shaft 702, which can include pullwires 743-1, 743-2 that extend through a sidewall of the elongate shaft 702 and can be configured to steer/deflect the elongate shaft 702. The distal tip 728 can extend distally from the distal end of the elongate shaft 702 and can include a distal tip lumen 741 in which a shaft associated with a looped distal end 704 or other type of device (e.g., flexible tip portion 110) can be inserted. The coupler 720 can define a longitudinally extending channel 740 in which a plurality of wires and/or tubes 724 can extend. In some embodiments, the wires and/or tubes 724 can extend through the longitudinally extending channel 740, through the distal tip lumen 741 and into the distal end 704.

As depicted, a first sensor 714-1 and second sensor 714-2 can be disposed in first and second sensor grooves 732-1, 732-2, respectively, which are each defined in an exterior surface of a body portion 730 of the coupler 720. As depicted, the cross-sections of the first sensor 714-1 and second sensor 714-2 are angular cross-sections, since each sensor 714-1, 714-2 is disposed at an angle with respect to a longitudinal axis along which the coupler 720 extends. As depicted, in some embodiments, the sensors 714-1, 714-2 can each be formed from tubes and can include a first sensor lumen 745-1 and a second sensor lumen 745-2.

As further depicted in FIG. 12F, a first placement slot 734-1 can be defined at a distal end of the first sensor groove 732-1. In some embodiments, first and second placement slots 734-1, 734-2 can be defined at the distal end of each one of the sensor grooves 732-1, 732-2. In some embodiments, the first and second sensors 714-1, 714-2 can be disposed within the first and second sensor grooves 732-1, 732-2 such that a distal end of each one of the first and second sensors 714-1, 714-2 is disposed within a respective one of the first and second placement slots 734-1, 734-2. In an example, the placement slots 734-1, 734-2 can ensure that the sensors will be disposed in a consistent location along the coupler 720 and will be disposed within a requisite distance of other features, such as ring electrode 726-1 and/or ring electrode 726-2. Although the electrodes 726-1, 726-2 are depicted as ring electrodes, the electrodes 726-1, 726-2 can be other types of electrodes (e.g., spot electrodes).

In some embodiments, a center of each sensor 714-1, 714-2 can be disposed at a certain distance, within a certain tolerance, from one of the electrodes on the deflectable elongate shaft 702 (e.g., first electrode 726-1). In some embodiments, a distal end of the first electrode 726-1, can be located a particular distance from a proximal end of the distal tip 728, defined by line 11. In an example, this distance can be in a range from 0.0285 to 0.0495 inches; although the distance can be less than 0.0285 inches or greater than 0.0495 inches.

In an example where the coupler 720 did not include placement slots 734-1, 734-2, a stack up may need to be created that includes multiple measurements to ensure that the sensors are properly aligned. In an example, an important measurement with regard to the stack up can be where the distal edge of the sensors 714-1, 714-2 is relative to the coupler 720 after the sensors 714-1, 714-2 have been seated into respective sensor grooves 732-1, 732-2. In an example, the placement slots 734-1, 734-2 enable the inspection of the relative placement of the sensors 714-1, 714-2 with respect to the coupler 720. For instance, if the distal edge of each sensor is disposed within the slot (e.g., window) of the placement slots 734-1, 734-2, a particular specification with regard to the placement of the sensors 714-1, 714-2 and the coupler 720 can be met.

Figure 13A:
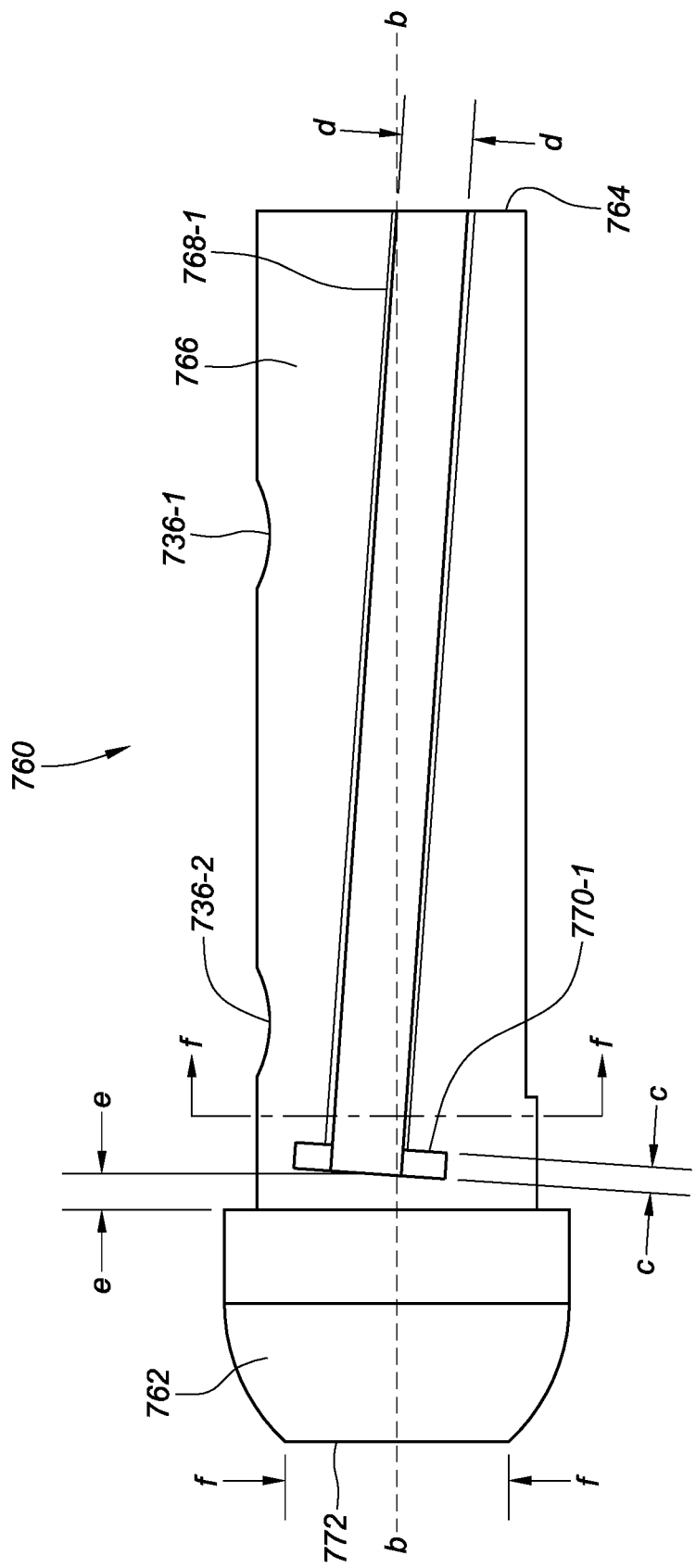
FIG. 13A is a schematic side view of a coupler, according to embodiments of the present disclosure.

FIG. 13A is a schematic side view of a coupler 760, according to embodiments of the present disclosure. As previously discussed, the coupler 760 can include a distal tip 762 and a proximal end 764 and can extend along a longitudinal axis bb. A body portion 766 can be coupled to a proximal end of the distal tip 762 and in some embodiments can have a diameter that is less than the distal tip 762. A pair of sensor grooves 768-1, 768-2 (FIG. 13B) can be defined in an exterior surface of the body portion 766. As depicted, the first sensor groove 768-1 can be disposed at a particular angle with respect to the longitudinal axis bb. Accordingly, upon placement of a sensor in the first sensor groove 768-1 and/or the second sensor groove 768-2, the sensors can be disposed at the particular angle with respect to the longitudinal axis bb. For example, in some embodiments, the first sensor groove 768-1 and the second sensor groove 768-2 can each be disposed at an angle in a range from 4.0±0.5 degrees with respect to the longitudinal axis bb. However, in some embodiments, as previously discussed herein, the angle at which the first sensor groove 768-1 and the second sensor groove 768-2 are disposed at with respect to the longitudinal axis bb can be greater than or less than 4.0 degrees. In some embodiments, a magnetic sensor (e.g., wrapped coil) can perform best when the longitudinal axis that extends through the magnetic sensor is disposed at an angle of 90 degrees with respect to the longitudinal axis bb, however, constraints on space associated with the coupler 760 can prevent the magnetic sensors from being disposed at such an angle with respect to the longitudinal axis bb.

In some embodiments, the first sensor groove 768-1 and the second sensor groove 768-2 can be disposed at equal, but opposite angles with respect to one another. In an example, the first sensor groove 768-1 can be disposed at an angle of 4 degrees with respect to the longitudinal axis bb and the second sensor groove 768-2 can be disposed at an angle of −4 degrees with respect to the longitudinal axis bb. Thus, the first sensor groove 768-1 and the second sensor groove 768-2 can be disposed at 8 degrees with respect to one another. Accordingly, magnetic sensors disposed in each one of the first sensor grooves 768-1, 768-2 can be disposed at 8 degrees with respect to one another. However, as discussed herein, the first sensor groove 768-1 and second sensor groove 768-2 can be disposed at other angles with respect to each other.

As depicted, a first placement slot 770-1 can be defined at a distal end of the first sensor groove 768-1 and a second placement slot (not depicted) can be defined at a distal end of the second sensor groove (not depicted). In some embodiments, an axial length of the placement slot grooves, defined by line cc can be approximately 0.007±0.001 inches in some embodiments. However, the axial length of the sensor placement slot can be less than or greater than 0.007±0.001 inches. In some embodiments, a diameter of the sensor grooves, defined by line dd can be approximately 0.019±0.001 inches, however, the diameter of the sensor grooves can be less than or greater than 0.019 inches. In some embodiments, an axial length of the body portion 766 can be approximately 0.266 inches, however, the axial length can be less than or greater than 0.266 inches. In some embodiments, a combined axial length of the sensor groove 768-1 and the first placement slot 770-1 can be 0.256 inches, however, the combined axial length can be less than or greater than 0.256 inches. In some embodiments, a distal wall that defines the sensor placement slot 770-1 can be disposed a distance of 0.0096±0.001 inches from a proximal end of the distal tip 762, as indicated by line ee, however, the distance can be can be greater than or less than 0.0096 inches. In some embodiments, the distal tip 762 can define an opening in which the looped distal end 704 or another device (e.g., flexible tip portion 110) can be inserted. In an example, an inner diameter of the opening 772 can be approximately 0.059±0.001 inches in some embodiments, although the diameter of the opening 772 can be larger or smaller than 0.059 inches.

Figure 13B:
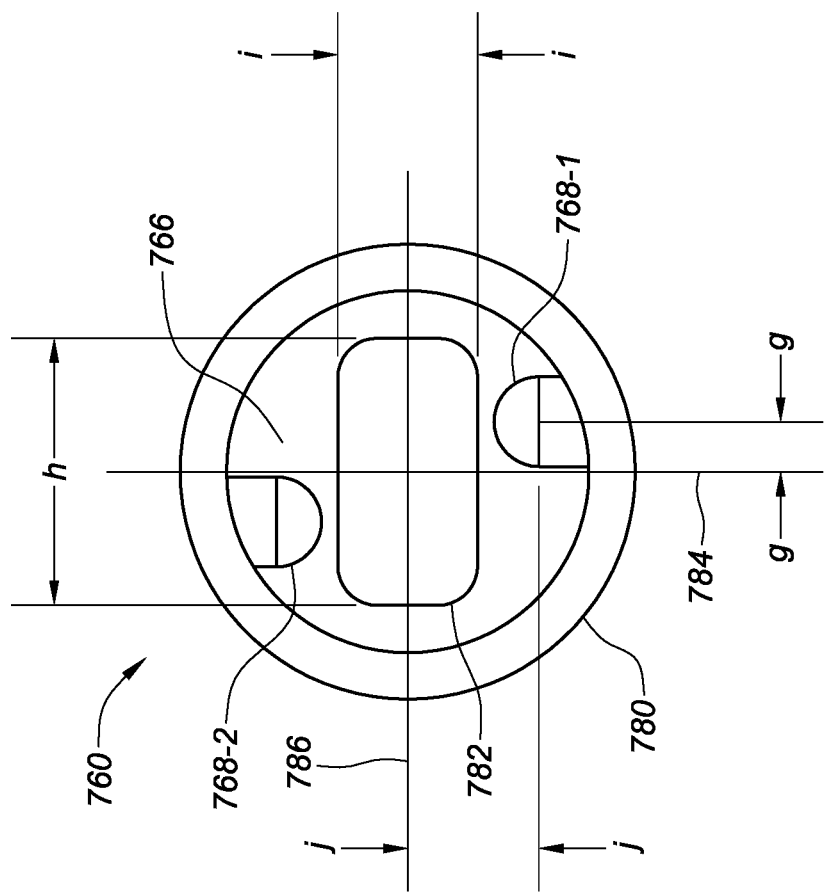
FIG. 13B depicts a schematic cross-sectional end view of the coupler in FIG. 13A upon insertion into a distal end of a shaft, according to embodiments of the present disclosure.

FIG. 13B depicts a schematic cross-sectional end view of the coupler 760 in FIG. 13A upon insertion into a distal end of a shaft 780, according to embodiments of the present disclosure. In some embodiments, the shaft 780 can have an outer diameter of 0.092±0.003 inches and the body portion 766 can be inserted into an inner lumen of the shaft 780. In some embodiments, the body portion 766 can have an outer diameter of 0.74±0.001 inches. As depicted, the shaft 780 can cover first and second sensor grooves 768-1, 768-2. Accordingly, sensors disposed in the first and second sensor grooves 768-1, 768-2 can be concealed underneath the shaft 780. The first and second sensor grooves 768-1, 768-2 can be located on either side of a vertical plane 784 that longitudinally extends through a middle of the body portion 766. In some embodiments, a distance from the vertical plane to a center of the first sensor groove 768-1 and/or the second sensor groove 768-2 can be define by line gg and can be approximately 0.010±0.001, although the distance can be greater than or less than 0.010.

As previously discussed herein, the coupler 760 can define a longitudinally extending channel 782, which can extend through the body portion 766 of the coupler 760. As depicted, a horizontal plane 786 can longitudinally extend through the middle of the body portion 766 and can be transverse to the vertical plane 784. The longitudinally extending channel 782 can have a width, defined by line hh of 0.054±0.001, although the width of the longitudinally extending channel 782 can be greater than or less than 0.054. In some embodiments, the longitudinally extending channel 782 can have a height, defined by line ii of 0.029±0.001, although the height of the longitudinally extending channel 782 can be greater than or less than 0.029. In some embodiments, a distance from the horizontal plane to each one of the sensor grooves 768-1, 768-2, defined by line jj can be 0.027±0.001, although the distance can be greater than or less than 0.027.

Figure 14:
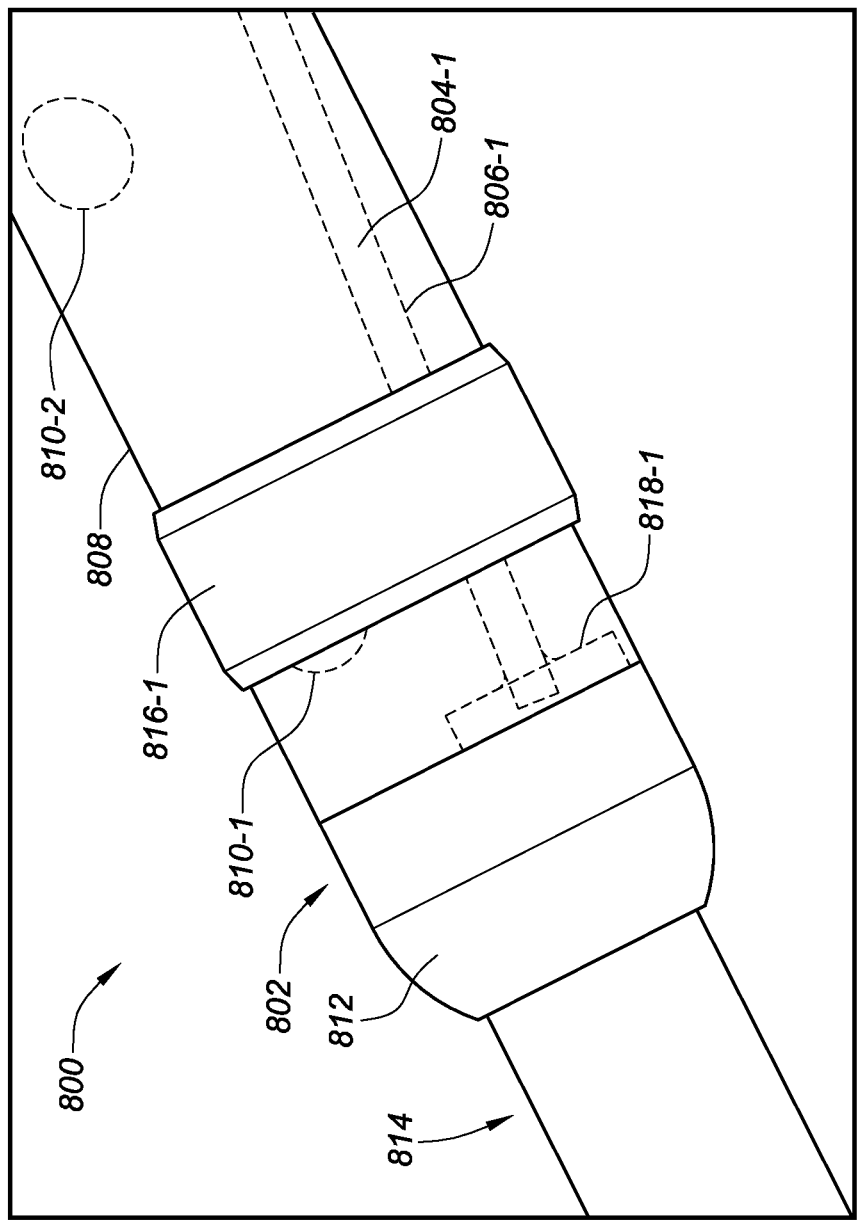
FIG. 14 is a side view of a medical device that includes a coupler and a magnetic position sensor disposed in a sensor groove, according to embodiments of the present disclosure.

FIG. 14 is a side view of a medical device 800 that includes a coupler 802 and a magnetic position sensor 804-1 disposed in a sensor groove 806-1, according to embodiments of the present disclosure. As previously discussed, the coupler 802 can have a distal tip 812 and can be disposed within a lumen defined by a distal end of an elongate shaft 808. A looped distal end 814 can be attached to the distal tip 812. The coupler 802 can define a first hole 810-1 and a second hole 810-2, which can allow for an adhesive to be introduced into a longitudinally extending channel 740 defined by the coupler 802. In some embodiments, the coupler 802 can define a first sensor groove 806-1 and a second sensor groove (not shown), in which a first sensor 804-1 and a second sensor (not shown) can be disposed, respectively. As previously discussed, it can be important for the sensors (e.g., first sensor 804-1) to have a particular placement with respect to the coupler 802 and electrodes (e.g., electrode 816-1) disposed on the medical device 800.

In some embodiments, as discussed herein, a placement slot 818-1 can be defined in an exterior surface of the coupler at a distal end of each one of the first sensor groove 806-1 and the second sensor groove. In an example, with respect to the first sensor, the first sensor 804-1 can be disposed in the first sensor slot 806-1, such that a distal end of the first sensor 804-1 can be disposed within the placement slot 818-1. Accordingly, since the distal end of the first sensor 804-1 is disposed within the placement slot 818-1, a visual verification can be made that establishes that the distal end of the first sensor 804-1 is disposed within the placement slot 818-1. Thus, a confirmation that the first sensor 804-1 is properly located on the coupler 802 can be made through the placement slot 818-1. A similar verification can be made with a second placement slot and second sensor, although not depicted in FIG. 14.

In some embodiments, upon assembly of the medical device 800, the coupler 802 can be strung over wires and/or tubes that are associated with looped distal end 814 or another device (e.g., flexible tip portion 110). In some embodiments, a verification can be made that a distal end of the first sensor 804-1 is disposed in the placement slot 818-1. Accordingly, the rest of the device can be assembled upon verification that the distal ends of the first sensor 804-1 and second sensor are disposed within the placement slots, thus ensuring that the sensors have been correctly disposed within the sensor grooves 806-1. If the coupler 802 did not include the placement slots, the sensors could be disposed within the sensor grooves incorrectly and thus upon final testing of the device after it had been constructed, the device may not pass the inspection, resulting in scrapping of the device at that point or resulting in the use of a new coupler 802 with new sensors. As such, through use of the placement slots, less scrap can be produced as a result of verifying that the sensors are properly placed within the grooves via the placement slots.

In some embodiments, the coupler 802 can be a molded component formed from a polymer (e.g., plastic). In an example, various features of the coupler 802 can be formed via the mold and/or can be machined. In some embodiments, the placement slot 818-1 can have an axial length of approximately 0.007 inches, although the axial length of the placement slot 818-1 can be less than 0.007 inches or greater than 0.007 inches. In an example, the axial length of the placement slot 818-1 was determined to allow for a visual inspection of the device to determine that the distal end of the sensor 804-1 is disposed within the placement slot 818-1. For instance, if the placement slot 818-1 had an axial length of less than 0.007 inches, it may be difficult to visually verify that the distal end of the sensor 804-1 was disposed within the placement slot 818-1. As mentioned, the side of the placement slot 818-1 can be varied, however a tolerance stack up related to the assembly of the coupler 801 and/or medical device 800 may need to be reassessed.

One advantage of the placement slots is that sensor placement can be inspected before the deflectable shaft is strung onto the device 800, reducing crap. For example, if the sensors are not in the correct place, then just the two sensors and coupler can be taken off and a new coupler can be strung on. If this feature were not inspected, the whole device would have to be scrapped. This is also advantageous to any dimension that cannot be measured directly and must be measured in a stack up of measurements.

Figure 15A:
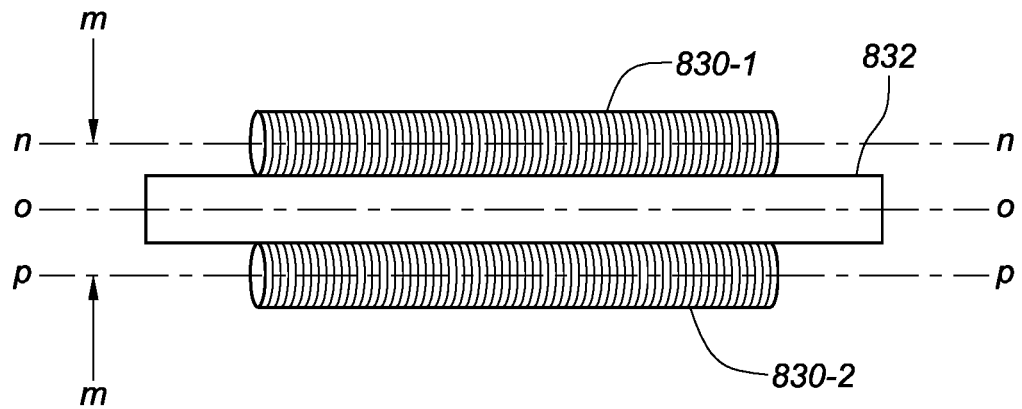
FIG. 15A is a side view of a magnetic sensor pair disposed on either side of a lumen, according to embodiments of the present disclosure.

FIG. 15A is a side view of a magnetic sensor pair 830-1, 830-2 disposed on either side of a lumen 832, according to embodiments of the present disclosure. As depicted, each of the magnetic sensors 830-1, 830-2 can be disposed along a longitudinal axis defined by lines nn and pp. For example, the first magnetic sensor 830-1 can be disposed along the axis nn and the second magnetic sensor 830-2 can be disposed along the axis pp. In some embodiments, the first magnetic sensor 830-1 and the second magnetic sensor 830-2 can be disposed on either side of a lumen 832, which extends along an axis defined by line oo. In an example, the lumen can be a tube and/or passageway in which wires and/or a fluid (e.g., irrigation fluid) passes. As depicted, each magnetic sensor 830-1, 830-2 can include a wire wrapped around an elongate cylindrical sensor core. In some embodiments, the sensor core can be formed from a magnetically permeable material, such as mu-metal. A center of each magnetic sensor 830-1, 830-2 can be disposed a particular distance from one another, which is defined by line mm.

In an example, each magnetic sensor 830-1, 830-2 can be a five degree of freedom sensor. The signals produced from each magnetic sensor 830-1, 830-2 can be analyzed together to determine a position and/or orientation of the pair of magnetic sensors 830-1, 830-2 with six degrees of freedom. Some six degree of freedom sensors can be constructed as two coils, each disposed at a small angle with respect to one another. The two coils can be adhered to a printed circuit board and calibrated individually. This can be both expensive and can result in a sensor package size that would not fit in some catheters. Consequently, embodiments of the present disclosure provide a more cost effective means of arranging two five degree of freedom sensors in a way that will fit in most catheters to create a single six degree of freedom sensor.

Figure 15B:
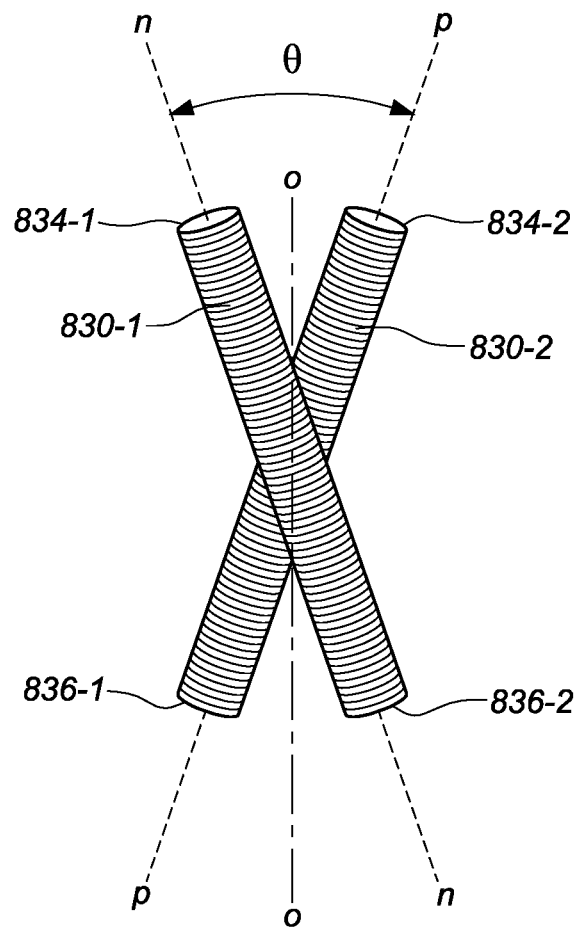
FIG. 15B is a top view of the magnetic sensor pair depicted in FIG. 15A, according to embodiments of the present disclosure.

FIG. 15B is a top view of the magnetic sensor pair 830-1, 830-2 depicted in FIG. 15A, according to embodiments of the present disclosure. As depicted, the magnetic sensor pair 830-1, 830-2 can be disposed at an angle Θ with respect to one another. For example, the longitudinal axis nn, along which the first magnetic sensor 830-1 extends can be disposed at the angle Θ with respect to the second magnetic sensor 830-2. In some embodiments, the angle Θ at which the magnetic sensor pair 830-1, 830-2 is disposed with respect to one another can be in a range from 1 degree to 20 degrees, 5 degrees to 15 degrees, and preferably from 10 degrees to 12 degrees. However, the angle Θ can be less than 1 degree or over 20 degrees, in some embodiments.

In some embodiments, depending on a size of a medical device (e.g., catheter) shaft, the angle between the magnetic sensors 830-1, 830-2 can be up to about 16 degrees. In an example, as the angle between the sensors 830-1, 830-2 increases, a distance between distal ends 834-1, 834-2 of the sensors 830-1, 830-2 and/or a distance between the proximal ends 836-1, 836-2 of the sensors 830-1, 830-2 can increase to a size where the distal ends 834-1, 834-2 and/or the proximal ends 836-1, 836-2 protrude through an outer surface of a catheter shaft in which they are exposed. Generally, as the angle between the magnetic sensors 830-1, 830-2 increases, an accuracy of a determined location of the magnetic sensor pair 830-1, 830-2 can increase. For example, a maximum accuracy can be obtained when the angle Θ between the magnetic sensors 830-1, 830-2 is at 90 degrees. However, a significant amount of space can be occupied by the magnetic sensors 830-1, 830-2, preventing the magnetic sensors 830-1, 830-2 from being positioned within an elongate shaft (e.g., catheter shaft).

Figure 16:
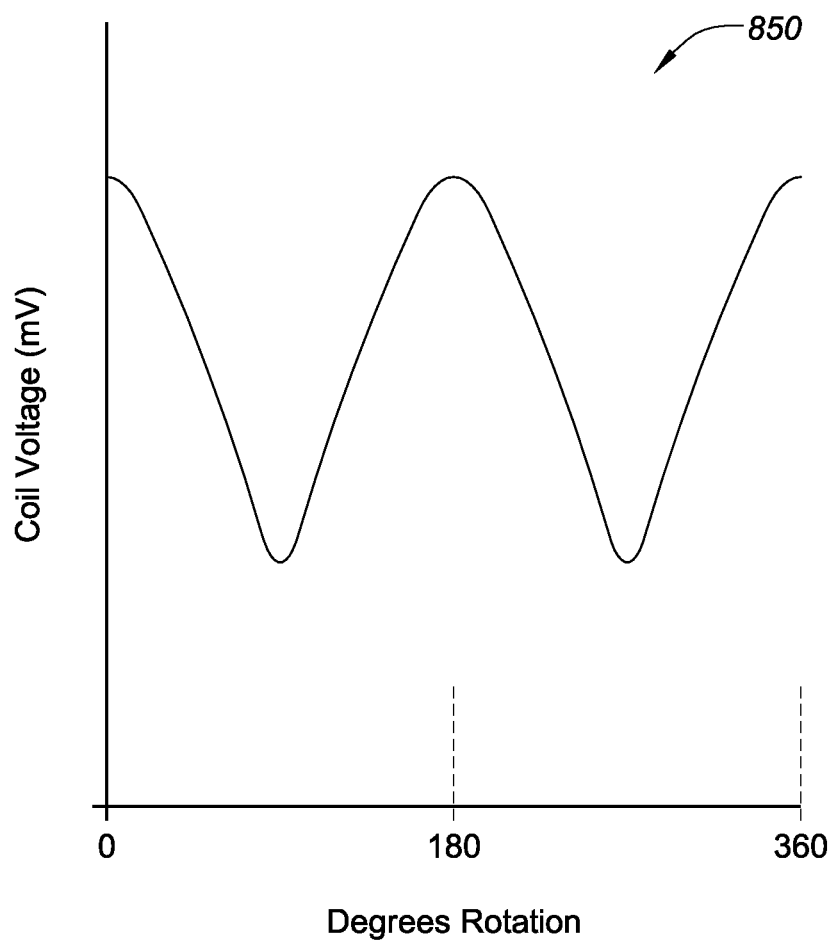
FIG. 16 is a model representative of a rotation of a five degree of freedom magnetic position sensor, according to embodiments of the present disclosure.

FIG. 16 is a model 850 representative of a rotation of a five degree of freedom magnetic position sensor, according to embodiments of the present disclosure. The model 850 represents a degree of rotation of the five degree of freedom magnetic position sensor versus a coil voltage produced by the five degree of freedom magnetic position sensor in millivolts (mV). In an example, as a five degree of freedom position sensor is rotated, a strength of a signal produced by the five degree of freedom position sensor can change as the sensor is rotated. For example, with reference to FIG. 16, peaks at 0 degrees, 180 degrees, and 360 degrees can correspond with an alignment of the five degree of freedom magnetic position sensor with an axis of a magnetic field in which the magnetic position sensor is disposed. Therefore, if two five degree of freedom sensors are included in a device (e.g., elongate shaft of a medical device) at a slight angle with respect to one another, they will be at different rotational angles with respect to the axis of the magnetic field. Thus, as the two five degree of freedom magnetic position sensors rotate, a difference in voltage and also their vectors can be picked up and consequently a six degree of freedom sensor can be created.

Figure 17A:
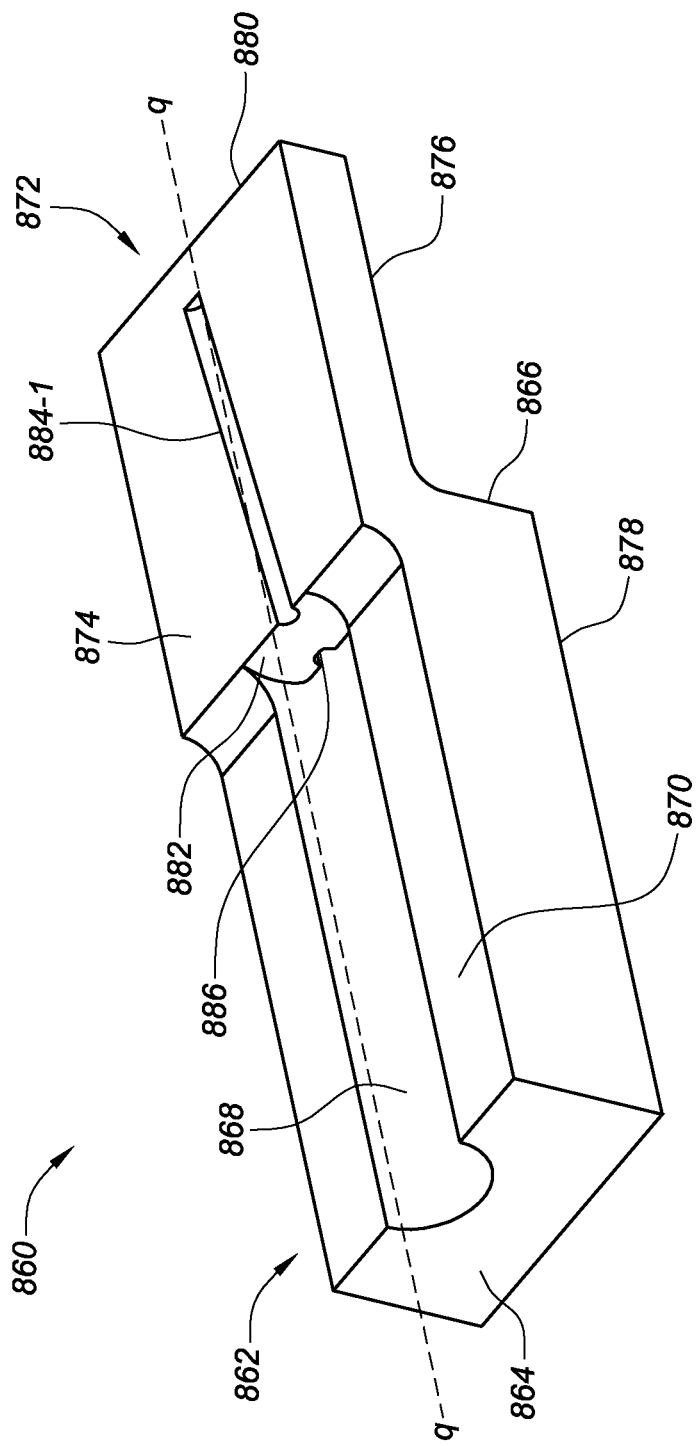
FIG. 17A is an isometric side, top, and rear view of a fixture for testing a pair of position sensors, according to embodiments of the present disclosure.

FIG. 17A is an isometric side, top, and rear view of a fixture 860 for testing a pair of position sensors, according to embodiments of the present disclosure. In some embodiments, the fixture 860 can include a body portion 862. The body portion 862 can include a proximal end 864 and a distal end 866. As depicted, the body portion 862 can have a rectangular cross-section, although the cross-section of the body portion 862 can be of another shape. In some embodiments, a hemi cylindrical channel 868 can be defined in a top surface 870 of the body portion 862. The hemi cylindrical channel 868 can extend along a longitudinal axis qq, as depicted in FIG. 17A. In some embodiments, a stepped portion 872 can extend distally from the distal end 866 of the body portion and can include a stepped distal end 880. In an example, the stepped portion 872 can include a top stepped surface 874 and a bottom stepped surface 876. In an example, the top stepped surface 874 can distally extend above the top surface 870 of the body portion 862 and the bottom stepped surface 876 can distally extend above a bottom surface 878 of the body portion 862.

In some embodiments, the hemi cylindrical channel 868 can be configured to accept an elongate shaft. In an example, the elongate shaft can be disposed within the hemi cylindrical channel 868 and a distal end of the elongate shaft can abut a distal channel face 882 at an interface between the body portion 862 and the stepped portion 872. In some embodiments, the top stepped surface 874 of the stepped portion 872 can define a first sensor groove 884-1. In some embodiments, the first sensor groove 884-1 can be disposed at an angle with respect to the longitudinal axis qq. For example, the first sensor groove 884-1 can extend through the longitudinal axis qq, as depicted in FIG. 17A.

Figure 17B:
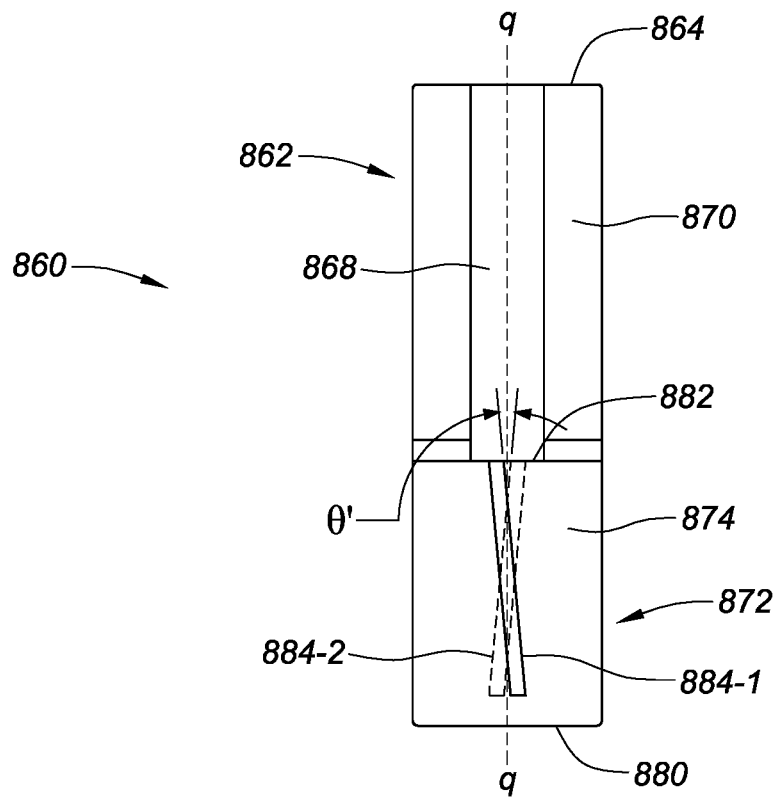
FIG. 17B is a top view of the fixture depicted in FIG. 17A for testing a pair of position sensors, according to embodiments of the present disclosure.

Additionally, the bottom stepped surface 876 can define a second sensor groove 884-2 (depicted in phantom in FIG. 17B). As depicted in FIG. 17A, the distal channel face 882 can define an opening 886, which can be in communication with the second sensor groove 884-2 to allow wires, etc. to pass through the distal channel face 882. The second sensor groove 884-2 can also extend through the longitudinal axis qq and can be disposed at an angle with respect to the longitudinal axis qq. In some embodiments, the angle at which the first sensor groove 884-1 is disposed at with respect to the longitudinal axis qq can be equal to, but opposite, of the angle at which the second sensor groove 884-2 is disposed at with respect to the longitudinal axis qq. For example, if the first sensor groove 884-1 is disposed at a five degree angle with respect to the longitudinal axis qq, then the second sensor groove 884-2 can be disposed at a negative five degree angle with respect to the longitudinal axis qq. In some embodiments, magnetic position sensors can be disposed in each one of the sensor grooves 884-1, 884-2 and the fixture 860 can be rotated about the longitudinal axis qq. Based on the rotation of the fixture about the longitudinal axis qq, the magnetic position sensors can produce varying signals indicative of the amount that the fixture has been rotated in a magnetic field.

FIG. 17B is a top view of the fixture 860 depicted in FIG. 17A for testing a pair of position sensors, according to embodiments of the present disclosure. In some embodiments, the fixture 860 can include a body portion 862. The body portion 862 can include a proximal end 864. In some embodiments, a hemi cylindrical channel 868 can be defined in a top surface 870 of the body portion 862. The hemi cylindrical channel 868 can extend along a longitudinal axis qq. In some embodiments, a stepped portion 872 can extend distally from the distal end 866 (FIG. 17A) of the body portion and can include a stepped distal end 880. In an example, the stepped portion 872 can include a top stepped surface 874.

In some embodiments, the hemi cylindrical channel 868 can be configured to accept an elongate shaft. The hemi cylindrical channel 868 can have a lateral width that is equivalent to a lateral width of an elongate shaft (e.g., catheter, sheath) that is disposed in the hemi cylindrical channel 868. For example, the lateral width of the hemi cylindrical channel 868 can be approximately 0.1 inches in some embodiments, although the lateral width of the channel 868 can be greater than or less than 0.1 inches. In an example, the elongate shaft can be disposed within the hemi cylindrical channel 868 and a distal end of the elongate shaft can abut a distal channel face 882 at an interface between the body portion 862 and the stepped portion 872. In some embodiments, the top stepped surface 874 of the stepped portion 872 can define a first sensor groove 884-1.

In some embodiments, the first sensor groove 884-1 can be disposed at an angle with respect to the longitudinal axis qq. For example, the first sensor groove 884-1 can extend through the longitudinal axis qq, as depicted in FIG. 17B. Additionally, the bottom stepped surface 876 (FIG. 17B) can define a second sensor groove 884-2 (depicted in phantom). The second sensor groove 884-2 can also extend through the longitudinal axis qq and can be disposed at an angle with respect to the longitudinal axis qq, resulting in the first sensor groove 884-1 being disposed at an angle Θ' with respect to the second sensor groove. In some embodiments, the angle at which the first sensor groove 884-1 is disposed at with respect to the longitudinal axis qq can be equal to, but opposite, of the angle at which the second sensor groove 884-2 is disposed at with respect to the longitudinal axis qq. For example, if the first sensor groove 884-1 is disposed at a five degree angle with respect to the longitudinal axis qq, then the second sensor groove 884-2 can be disposed at a negative five degree angle with respect to the longitudinal axis qq. In some embodiments, magnetic position sensors can be disposed in each one of the sensor grooves 884-1, 884-2 and the fixture 860 can be rotated about the longitudinal axis qq. Based on the rotation of the fixture about the longitudinal axis qq, the magnetic position sensors can produce varying signals indicative of the amount that the fixture has been rotated in a magnetic field.

Figure 17C:
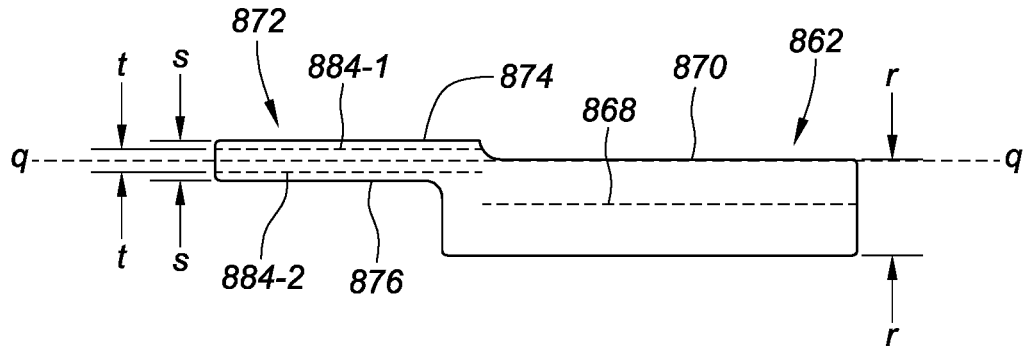
FIG. 17C is a side view of the fixture depicted in FIGS. 17A and 17B for testing a pair of position sensors, according to embodiments of the present disclosure.

FIG. 17C is a side view of the fixture 860 depicted in FIGS. 17A and 17B for testing a pair of position sensors, according to embodiments of the present disclosure. The body portion 862 can have a thickness, represented by line rr, of approximately 0.125 inches, although the thickness can be greater than or less than 0.125 inches. As depicted, the hemi cylindrical channel 868 can be defined in the top surface 870. In some embodiments, the top stepped surface 874 of the stepped portion 872 can define the first sensor groove 884-1 and the bottom stepped surface 876 can define the second sensor groove 884-2. In some embodiments, the stepped portion 872 can have a thickness, represented by line ss, of approximately 0.055 inches, although the thickness can be greater or less than 0.055 inches. In an example, a distance, represented by line tt, of approximately 0.037 inches can separate the first sensor groove 884-1 from the second sensor groove 884-2, although the distance can be greater or less than 0.037 inches.

Figure 17D:
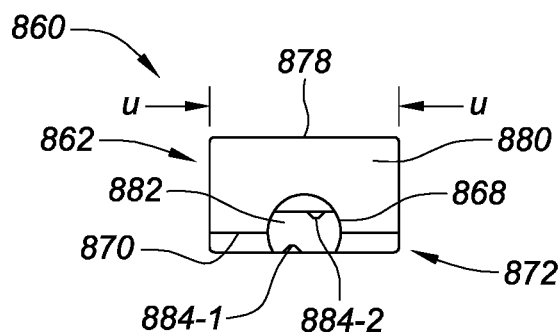
FIG. 17D is a proximal end view of the fixture depicted in FIGS. 17A to 17C for testing a pair of position sensors, according to embodiments of the present disclosure.

FIG. 17D is a proximal end view of the fixture 860 depicted in FIGS. 17A to 17C for testing a pair of position sensors, according to embodiments of the present disclosure. The body portion 862 can include a top surface 870 and a bottom surface 878. The body portion 862 can define a hemi cylindrical channel 868 in a top surface of the body portion 862. As depicted, a first sensor groove 884-1 and a second sensor groove 884-1 can extend through a distal channel face 882 and can be formed in the stepped portion 872, as previously described herein. In some embodiments, the fixture 860 can have a width of approximately 0.250 inches, although the width can be greater than or less than 0.250 inches in some embodiments.

In some embodiments, as previously discussed, an elongate shaft can be disposed in the hemi cylindrical channel 868 and connected to the fixture 860. Additionally, a first magnetic sensor can be disposed in the first sensor groove 884-1 and a second magnetic sensor can be disposed in the second sensor groove 884-2. The elongate shaft can be turned in some embodiments, causing the fixture 860 to revolve around the axis qq. As the fixture and the magnetic sensors revolve around the axis qq, the a signal produced by each one of the magnetic sensors can vary. Accordingly, the signals can be analyzed and a determination of a degree of rotation of the fixture and the sensors can be determined.

In some embodiments, the fixture 860 can be used to measure an effect of an angle at which the first magnetic sensor is disposed with respect to the second magnetic sensor. For example, as previously discussed herein, as an angle at which the first magnetic sensor is disposed with respect to the second magnetic sensor increases, an accuracy at which the location of the first and second magnetic sensor can be determined increases. Accordingly, an angle at which the first magnetic sensor is disposed with respect to the second magnetic sensor can be optimized using the fixture 860 in terms of accuracy versus a size of the sensor. For instance, as previously discussed, increasing an angle at which the first magnetic sensor is disposed with respect to the second magnetic sensor can result in a larger size of the sensor pair (e.g., a distance between respective proximal and distal ends of the sensor pair). Disposing the first magnetic sensor at a larger angle with respect to the second magnetic sensor on the fixture and/or a device as previously described herein, can result in any slight manufacturing difference between sensor placement not having as drastic of an effect on a signal output produced by the first and second magnetic sensors. As a result, calibration of a device that includes the first magnetic sensor and the second magnetic sensor may not be as significant of a problem since any slight manufacturing difference between sensor placement may not have as drastic of an effect on signal output. Furthermore, by disposing the first magnetic sensor and the second magnetic sensor in the fixture and/or a device that includes the first and second sensor grooves, calibration can be more easily performed. For example, upon construction of a device and/or fixture 860 that includes the sensor grooves 884-1, 884-2, magnetic sensors can be accurately placed in the sensor grooves 884-1, 884-2, resulting in less of a variance between placement of the sensors from one device to another.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it may be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for an irrigated high density electrode catheter has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and may include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed:

1. An irrigated high density electrode catheter, comprising:
   a catheter shaft including a proximal end and a distal end, the catheter shaft defining a catheter shaft longitudinal axis;
   a flexible tip portion located adjacent to the distal end of the catheter shaft and comprising a plurality of microelectrodes;

an irrigated coupler disposed on the distal end of the catheter shaft and configured to discharge fluid over the flexible tip portion;

a six degree of freedom sensor assembly; and a connective stem comprising a top connective stem member and a bottom connective stem member, wherein the top connective stem member and the bottom connective stem member are separate components that are configured to be assembled together with a proximal end portion of the flexible tip portion to house the proximal end portion of the flexible tip portion, wherein the connective stem is configured to be inserted into the distal end of the catheter shaft and connects the proximal end portion of the flexible tip portion to the catheter shaft, wherein the connective stem houses the six degree of freedom sensor assembly, and wherein the connective stem and the irrigated coupler are separate components that are configured to accommodate coupling of the irrigated coupler to the connective stem after insertion of the connective stem into the distal end of the catheter shaft.

2. The irrigated high density electrode catheter of claim 1, wherein the irrigated coupler is configured to connect the flexible tip portion with the catheter shaft.

3. The irrigated high density electrode catheter of claim 1, wherein the irrigated coupler is configured to discharge fluid towards targeted portions of the flexible tip portion.

4. The irrigated high density electrode catheter of claim 1, wherein:
the six degree of freedom sensor assembly includes a pair of five degree of freedom magnetic position sensors;
a first one of the pair of five degree of freedom magnetic position sensors includes a first coil wound about a first sensor longitudinal axis; and
a second one of the pair of five degree of freedom magnetic position sensors includes a second coil wound about a second sensor longitudinal axis.

5. The irrigated high density electrode catheter of claim 4, wherein:
the first sensor longitudinal axis is divergent with the second sensor longitudinal axis and with the catheter shaft longitudinal axis; and
the second sensor longitudinal axis is divergent with the first sensor longitudinal axis and with the catheter shaft longitudinal axis.

6. The irrigated high density electrode catheter of claim 5, wherein:
the first sensor longitudinal axis is disposed at an angle with respect to the second sensor longitudinal axis; and
the angle is in a range from 1 to 20 degrees.

7. The irrigated high density electrode catheter of claim 6, wherein the angle is in a range from 5 to 15 degrees.

8. The irrigated high density electrode catheter of claim 6, wherein the angle is in a range from 10 to 12 degrees.

9. The irrigated high density electrode catheter of claim 4, wherein:
the first one of the pair of five degree of freedom magnetic position sensors is disposed in the top connective stem member; and
the second one of the pair of five degree of freedom magnetic position sensors is disposed in the bottom connective stem member.

10. The irrigated high density electrode catheter of claim 9, wherein:
the top connective stem member defines a first sensor groove in an exterior surface of the top connective stem member, the first one of the pair of five degree of freedom magnetic position sensors being disposed within the first sensor groove; and
the bottom connective stem member defines a second sensor groove in an exterior surface of the bottom connective stem member, the second one of the pair of five degree of freedom magnetic position sensors being disposed within the second sensor groove.

11. The irrigated high density electrode catheter of claim 9, wherein:
the top connective stem member defines a first sensor lumen therein, the first one of the pair of five degree of freedom magnetic position sensors being disposed within the first sensor lumen; and
the bottom connective stem member defines a second sensor lumen therein, the second one of the pair of five degree of freedom magnetic position sensors being disposed within the second sensor lumen.

12. The irrigated high density electrode catheter of claim 1, further comprising:
a fluid inlet defined in the top connective stem member; and
an irrigation cross-over defined by the top connective stem member and the bottom connective stem member, wherein the irrigation cross-over is configured to transfer fluid from the top connective stem member to the bottom connective stem member.

13. The irrigated high density electrode catheter of claim 12, wherein the top connective stem member and the bottom connective stem member are configured to discharge fluid into the irrigated coupler.

14. A catheter, comprising:
an elongate shaft including a proximal end and a distal end, the elongate shaft defining a shaft longitudinal axis;
an electrode assembly comprising a plurality of microelectrodes;
a coupler assembly comprising a coupler and a connective stem, wherein the connective stem extends within a distal end of the elongate shaft, wherein the connective stem defines a first sensor groove and a second sensor groove in an exterior surface of the connective stem, wherein the connective stem comprises a top connective stem member in which the first sensor groove is defined and a bottom connective stem member in which the second sensor groove is defined, wherein the top connective stem member and the bottom connective stem member are separate components that are configured to be assembled together with a proximal end portion of the electrode assembly to house the proximal end portion of the electrode assembly, wherein the top connective stem member is configured to interlock with the bottom connective stem member via longitudinally extending grooves, wherein the connective stem is configured to be inserted into the distal end of the elongate shaft, and wherein the connective stem and the coupler are separate components that are configured to accommodate coupling of the coupler to the connective stem after insertion of the connective stem into the distal end of the elongate shaft;
a first five degree of freedom magnetic position sensor disposed in the first sensor groove and elongated along a first sensor longitudinal axis that is non-parallel to the shaft longitudinal axis; and
a second five degree of freedom magnetic position sensor disposed in the second sensor groove and elongated along a second sensor longitudinal axis that is not parallel to each of the shaft longitudinal axis and the first sensor longitudinal axis.

15. The catheter of claim 14, wherein the connective stem defines a first placement slot at a distal end of the first sensor groove and a second placement slot at a distal end of the second sensor groove.

16. The catheter of claim 15, wherein each of the first placement slot and the second placement slot are cross-longitudinal slots defined in the exterior surface of the connective stem.

17. The catheter of claim 16, wherein:
a distal end of the first five degree of freedom magnetic position sensor is disposed within the first placement slot; and
a distal end of the second five degree of freedom magnetic position sensor is disposed within the second placement slot.

18. A medical device, comprising:
an elongate shaft including a proximal end and a distal end, the elongate shaft defining a shaft longitudinal axis;
a flexible tip mount that extends within the distal end of the elongate shaft, wherein the flexible tip mount includes a connective stem and an irrigated coupler, wherein the connective stem comprises a top connective stem member and a bottom connective stem member, wherein the top connective stem member and the bottom connective stem member are separate components that are configured to be assembled together to form the connective stem, wherein the connective stem is configured to be inserted into the distal end of the elongate shaft, wherein the top connective stem member and the bottom connective stem member comprise opposing complementary surfaces, wherein the top connective stem member defines a first sensor groove in an exterior surface of the top connective stem member, wherein the bottom connective stem member defines a second sensor groove in an exterior surface of the bottom connective stem member, and wherein the connective stem and the irrigated coupler are separate components that are configured to accommodate coupling of the irrigated coupler to the connective stem after insertion of the connective stem into the distal end of the elongate shaft;
a flexible tip assembly comprising a proximal mounting portion and a distal flexible portion, wherein the proximal mounting portion is disposed between the opposing complementary surfaces of the top connective stem member and the bottom connective stem member, wherein the opposing complementary surfaces are configured to interlock with one another via longitudinally extending ridges with the proximal mounting portion disposed between the opposing complementary surfaces;
a first five degree of freedom magnetic position sensor disposed in the first sensor groove; and
a second five degree of freedom magnetic position sensor disposed in the second sensor groove.

19. The medical device of claim 18, wherein:
the first sensor groove is aligned with a first sensor longitudinal axis;
the second sensor groove is aligned with a second sensor longitudinal axis;
the first sensor longitudinal axis is divergent with respect to the second sensor longitudinal axis; and
the shaft longitudinal axis and the second sensor longitudinal axis is divergent with respect to the first sensor longitudinal axis and the shaft longitudinal axis.

\* \* \* \* \*